US009089565B2

(12) United States Patent
Takei

(10) Patent No.: US 9,089,565 B2
(45) Date of Patent: Jul. 28, 2015

(54) COMPOSITIONS AND METHODS FOR CAUSING NEURITE OUTGROWTH

(75) Inventor: Yoshinori Takei, Kyoto (JP)

(73) Assignee: MEDICAL RESEARCH COUNCIL, Swindon (GB)

( * ) Notice: Subject to any disclaimer, the term of this patent is extended or adjusted under 35 U.S.C. 154(b) by 0 days.

(21) Appl. No.: 13/254,081

(22) PCT Filed: Mar. 5, 2010

(86) PCT No.: PCT/GB2010/000391
§ 371 (c)(1),
(2), (4) Date: Aug. 31, 2011

(87) PCT Pub. No.: WO2010/100428
PCT Pub. Date: Sep. 10, 2010

(65) Prior Publication Data
US 2011/0318326 A1    Dec. 29, 2011

(30) Foreign Application Priority Data

Mar. 6, 2009   (GB) .................................. 0903913.2

(51) Int. Cl.
| C12N 9/12 | (2006.01) |
| C12N 5/0793 | (2010.01) |
| A61P 25/00 | (2006.01) |
| A61K 38/45 | (2006.01) |
| C12N 9/10 | (2006.01) |
| C12N 9/00 | (2006.01) |

(52) U.S. Cl.
CPC . A61K 38/45 (2013.01); C12N 9/00 (2013.01); C12N 9/10 (2013.01); C12N 9/1211 (2013.01)

(58) Field of Classification Search
None
See application file for complete search history.

(56) References Cited

U.S. PATENT DOCUMENTS

| 2004/0248251 A1* | 12/2004 | Lal et al. ...................... 435/69.1 |
| 2005/0214288 A1 | 9/2005 | Bell et al. |
| 2008/0274077 A1* | 11/2008 | Benowitz et al. ............ 424/85.2 |

FOREIGN PATENT DOCUMENTS

| EP | 1431308 | 9/2002 |
| JP | 2002510490 A | 4/2002 |
| WO | 2005000114 | 1/2005 |
| WO | 2005/059515 | 6/2005 |
| WO | 2006017673 | 2/2006 |
| WO | 2008/116032 | 3/2008 |

OTHER PUBLICATIONS

Filbin, Marie T.; "Myelin_Associated Inhibitors of Axonal Regeneration in the Adult Mammalian CNS" Neuroscience, 4, 1-11, 2003.*
Díaz-Nido, Javier; et al; "Journal of NeurochemistryPhosphorylation of Microtubule Proteins in Rat Brain at Different Developmental Stages: Comparison with That Found in Neuronal Cultures," 54, 211-222, 1990.*

(Continued)

*Primary Examiner* — Blaine Lankford
*Assistant Examiner* — David Berke-Schlessel
(74) *Attorney, Agent, or Firm* — Kenealy Vaidya LLP

(57) ABSTRACT

The invention relates to a method for alleviating the inhibition of neurite outgrowth from a neurone, wherein said neurone comprises a Nogo receptor, said method comprising contacting said neurone with a composition capable of causing phosphorylation of a Nogo receptor, wherein said composition comprises protein kinase A or casein kinase.

13 Claims, 10 Drawing Sheets

(56) References Cited

OTHER PUBLICATIONS

Taniuchi, Megumi; et al; "Phosphorylation of Nerve Growth Factor Receptor Proteins Sympathetic Neurons andP C12 Cells" The Journal of Biological Chemistry, 261, 13342-13349, 1986.*

Arevalo, Maria-Angeles; et al; "Activation of Casein Kinase II and Inhibition of Phosphatase and Tensin Homologue Deleted on Chromosome 10 Phosphatase by Nerve Growth Factor/p75NTR Inhibit Glycogen Synthase Kinase-3 and Stimulate Axonal Growth" Molecular Biology of the Cell, 17, 3369-3377, 2006.*

Audesirk, Geral; et al; "Modulation of neurite branching by protein phosphorylation in cultured rat hippocampal neurons" Developmental Brain Research, 102, 247-260, 1997.*

He, Zhigang; Koprivica, Vuk; "The Nogo Signaling Pathway for Regeneration Block" Annual Review of Neuroscience, 27, 341-368, 2004.*

Nelson, David L; Cox, Michael M; Principles of Biochemistry: Fourth Edition, New York, 2005.*

Van Lint, Johanl; et al; "Tumor Necrosis Factor Stimulates Multiple Serine/Threonine Protein Kinases in Swiss 3T3 and L929 Cells" The Journal of Biological Chemistry, 267, 25916-25921, 1992.*

Chen, Chien-Hsing; et al; "Role of PKA in the Anti-Thy-1 Antibody-Induced Neurite Outgrowth of Dorsal Root Ganglionic Neurons" Journal of Cellular Biochemistry, 101, 556-575, 2007.*

Domeniconi, Marco; Filbin, Marie T; "Overcoming inhibitors in myelin to promote axonal regeneration" Journal of the Neurological Sciences, 233, 43-47, 2005.*

Lee, Daniel HS; et al; "Targeting the Nogo Receptor to Treat Central Nervous System Injuries" Nature Reviews, 2, 1-7, 2003.*

Schweigreiter, Rudiger; Bandtlow, Christine E; "Nogo in the Injured Spinal Cord" Journal of Neurotrauma, 23, 384-396, 2004.*

Barton et al., "Structure and axon outgrowth inhibitor binding of the Nogo-66 receptor and related proteins," EMBO J., 22:3291-3302 (2003).

Chivatakarn et al., "The Nogo-66 receptor NgR1 is required only for the acute growth cone-callapsing but not the chronic growth-inhibitory actions of myelin inhibitors," J. Neurosci., 27:7117-7124 (2007).

Hannila et al., "The role of cyclic AMP signaling in promoting axonal regeneration after spinal cord injury," Exp. Neurol., 209:321-332 (2008).

International Search Report in PCT/GB2010/000391, dated Aug. 20, 2010.

Mehta et al., "Gangliosides and Nogo receptors independently mediate myelin-associated glycoprotein inhibition of neurite outgrowth in different nerve cells," J. Biol. Chem., 282:27875-27886 (2007).

Mingorance et al., "Regeneration of lesioned entorhino-hippocampal axons in vitro by combined degradation of inhibitory proteoglycans and blockage of Nogo-66/NgR signaling," FASEB J., 20:491-493 (2006).

Niederost et al., "Nogo-A and myelin-associated glycoprotein mediate neurite growth inhibition by antagonistic regulation of RhoA and Rac1," J. Neursci., 22(23):10368-10376 (2002) XP002590031.

Oertle et al., "Nogo-A inhibitis neurite outgrowth and cell spreading with three discrete regions," J. Neurosci., 23(13):5393-5406 (2003) XP002973436.

Park et al., "Alzheimer precursor protein interaction with the Nogo-66 receptor reduces amyloid-beta plaque deposition," J. Neurosci., 26:1386-1395 (2006).

Schwab et al., "Oligodendrocytes and CNS myelin are nonpermissive substrates for neurite growth and fibroblast spreading in vitro," J. Neurosci., 8:2381-2393 (1988).

Schwiebert, "Extracellular ATP-mediated propogation of Ca(2+) waves. Focus on "mechanical strain-induced Ca(2+) waves are propagated via ATP release and purinergic receptor activation"," Am. J. Physiol. Cell Physiol., 279:C281-C283 (2000).

Su et al., "Nogo enhances the adhesion of olfactory ensheathing cells and inhibits their migration," J. Cell Sci., 120(Pt 11):1877-1887 (2007).

Ulloa et al., "Depletion of casein kinase II by antisense oligonucleotide prevents neuritogenesis in neuroblastoma cells," EMBO J., 12:1633-1640 (1993).

Venkatesh et al., "The Nogo-66 receptor homolog NgR2 is a sialic acid-dependent receptor selective for myelin-associated glycoprotein," J. Neurosci., 25:808-822 (2005).

Walmsley et al., "Zinc metalloproteinase-mediated cleavage of the human Nogo-66 receptor," J. Cell Sci., 117(Pt 19):4591-4602 (2004).

Walter et al., "Ectodomain phosphorylation of beta-amyloid precursor protein at two distinct cellular locations," J. Biol. Chem., 272:1896-1903 (1997).

Walter et al., Phosphorylation of the beta-amyloid precursor protein at the cell surface by ectocasein kinases 1 and 2, J. Biol. Chem., 275:23523-23529 (2000).

Wang et al., "Nogo-66 promotes the differentiation of neural progenitors into astroglial lineage cells through mTOR-STAT3 pathway," PLoS One, 3:e1856 (2008).

Yamauchi et al., "Phosphorylation of neuroglycan C, a brain-specific transmembrane chondroitin sulfate proteoglycan, and its localization in the lipid rafts," J. Biol. Chem., 277:20583-20590 (2002).

Zimina et al., "Extracellular phosphorylation of collagen XVII by ecto-casein kinase 2 inhibits ectodomain shedding," J. Biol. Chem., 282:22737-22746 (2007).

Aglah et al., "cAMP promotes neurite outgrowth and extension through protein kinase A but independently of ERK activation in cultured rat motoneurons," Neuropharmacology, 55(1):8-17 (2008) XP022779076.

Grandpre et al., "Nogo-66 receptor antagonist peptide promotes axonal regeneration," Nature, 417:547-551 (2002).

Great Britain Search Report in GB 0903913.2, dated Jul. 13, 2009.

He Zhigang et al., "The Nogo signaling pathway for regeneration block," Annu. Rev. Neurosci., 27:341-368 (2004) XP002590029.

International Search Report and Written Opinion in PCT/GB2010/000391, dated Aug. 20, 2010.

Lee et al., "Targeting the Nogo receptor to treat central nervous system injuries," Nat. Rev. Drug Discov., 2(11):872-878 (2003) XP002590030.

Oertle et al., "Nogo-A inhibits neurite outgrowth and cell spreading with three discrete regions," J. Neurosci., 23 (13):5393-5406 (2003) XP00297343.

Takei Yoshinori, "Phosphorylation of Nogo receptors suppresses Nogo signaling, allowing neurite regeneration," Sci. Signal., 2(64):ra14 (2009) XP009135691.

Ulloa et al., "Depletion of casein kinase II by antisense oligonucleotide prevents neuritogenesis in neuroblastoma cells," The EMBO J., 12:1633-1640 (1993).

Aloy et al., "Synaptic destabilization by neuronal Nogo-A," Brain Cell Biol., 35:137-156 (2006).

Atwal et al., "PirB is a functional receptor for myelin inhibitors of axonal regeneration," Science, 322(5903):967-970 (2008).

Blanquet et al., "Neurotrophin-induced activation of casein kinase 2 in rate hippocampal slices," Neuroscience, 86:739-749 (1998).

Bregman et al., "Neurotrophic factors increase axonal growth after spinal cord injury and transplantation in the adult rat," Exp. Neurol., 148:475-494 (1997).

Cai et al., "Prior exposure to neurotrophins blocks inhibition of axonal regeneration by MAG and myelin via a cAMP-dependent mechanism," Neuron., 22:89-101 (1999).

Dinocourt et al., "Injury-induced axonal sprouting in the hippocampus is initiated by activation of trkB receptors," Eur. J. Neurosci., 24:1857-1866 (2006).

Encinas et al., "Sequential treatment of Sh-SY5Y cells with retinoic acid and brain-derived neurotrophic factor gives rise to fully differentiated, neurotrophic factor-dependent, human neuron-like cells," J. Neurochem., 75:991-1003 (2000).

Fryer et al., "Truncated trkB receptors on nonneuronal cells inhibit BDNF-induced neurite outgrowth in vitro," Exp. Neurol., 148:616-627 (1997).

Gil et al., "Nogo-A expression in the human hippocampus in normal aging and in Alzheimer disease," J. Neuropathol. Exp. Neurol., 65:433-444 (2006).

(56) References Cited

OTHER PUBLICATIONS

Gonzenbach et al., "Disinhibition of neurite growth to repair the injured adult DNA: focusing on Nogo," Cell Mol. Life Sci., 65:161-176 (2008).

He et al., "Structure of the Nogo receptor ectodomain: a recognition module implicated in myelin inhibition," Neuron., 38:177-185 (2003).

Jakeman et al., "Brain-derived neurotrophic factor stimulates hindlimb stepping and sprouting of cholinergic fibers after spinal cord injury," Exp. Neurol., 154:170-184 (1998).

Jin et al., "Transplants of fibroblasts genetically modified to express BDNF promote axonal regeneration from supraspinal neurons following chronic spinal cord injury," Exp. Neurol., 177:265-275 (2002).

Kluge et al., "Tracing of the entorhinal-hippocampal pathway in vitro," Hippocampus, 8:57-68 (1998).

Lu et al., "Neurotrophism without neurotropism: BDNF promotes survival but not growth of lesioned corticospinal neurons," J. Comp. Neurol., 436:456-470 (2001).

McGee et al., "The Nogo-66 receptor: focusing myelin inhibition of axon regeneration," Trends Neurosci., 26:193-198 (2003).

Pahlman et al., "Retinoic acid-induced differentiation of cultured human neuroblastoma cells: a comparison with phorbolester-induced differentiation," Cell Differ., 14:135-144 (1984).

Pastrana et al., "BDNF production by olfactory ensheathing cells contributes to axonal regeneration of cultured adult CNS neurons," Neurochem. Int., 50:491-498 (2007).

Prang et al., "Regeneration of entorhinal fibers in mouse slice cultures is age dependent and can be stimulated by NT-4, GDNF, and modulators of G-proteins and protein kinase D," Exp. Neurol., 169:135-147 (2001).

Redegeld et al., "Ecto-protein kinases: ecto-domain phosphorylation as a novel target for pharmacological manipulation?" Trends Pharmacol. Sci., 20:453-459 (1999).

Salie et al., "IGF-1 and BDNF promote chick bulbospinal neurite outgrowth in vitro," Int. J. Dev. Neurosci., 23:587-598 (2005).

Sawynok et al., "Adenosine in the spinal cord and periphery: release and regulation of pain," Prog. Neurobiol., 69:313-340 (2003).

Schwab et al., "The Nogo receptor complex: confining molecules to molecular mechanisms," Trends Mol. Med., 12:293-297 (2006).

Schwab, "Repairing the injured spinal cord," Science, 295:1029-1031 (2002).

Walmsley et al., "Ectodomain shedding of human Nogo-66 receptor homologue-1 by zinc metalloproteinases," Biochem., Biophys. Res. Commun., 327:112-116 (2005).

Wang et al., "The interaction of Nogo-66 receptor with Nogo-p4 inhibits the neuronal differentiation of neural stem cells," Neuroscience, 151:74-81 (2008).

Zhu et al., "Increased expression of the Nogo receptor in the hippocampus and its relation to the neuropathology in Alzheimer's disease," Hum. Pathol., 38:426-434 (2007).

Chen et al., "Role of PKA in the Anti-Thy-1 Antibody-Induced Neurite Outgrowth of Dorsal Root Ganglionic Neurons," J. Cell. Biochem., 101:566-575 (2007).

\* cited by examiner

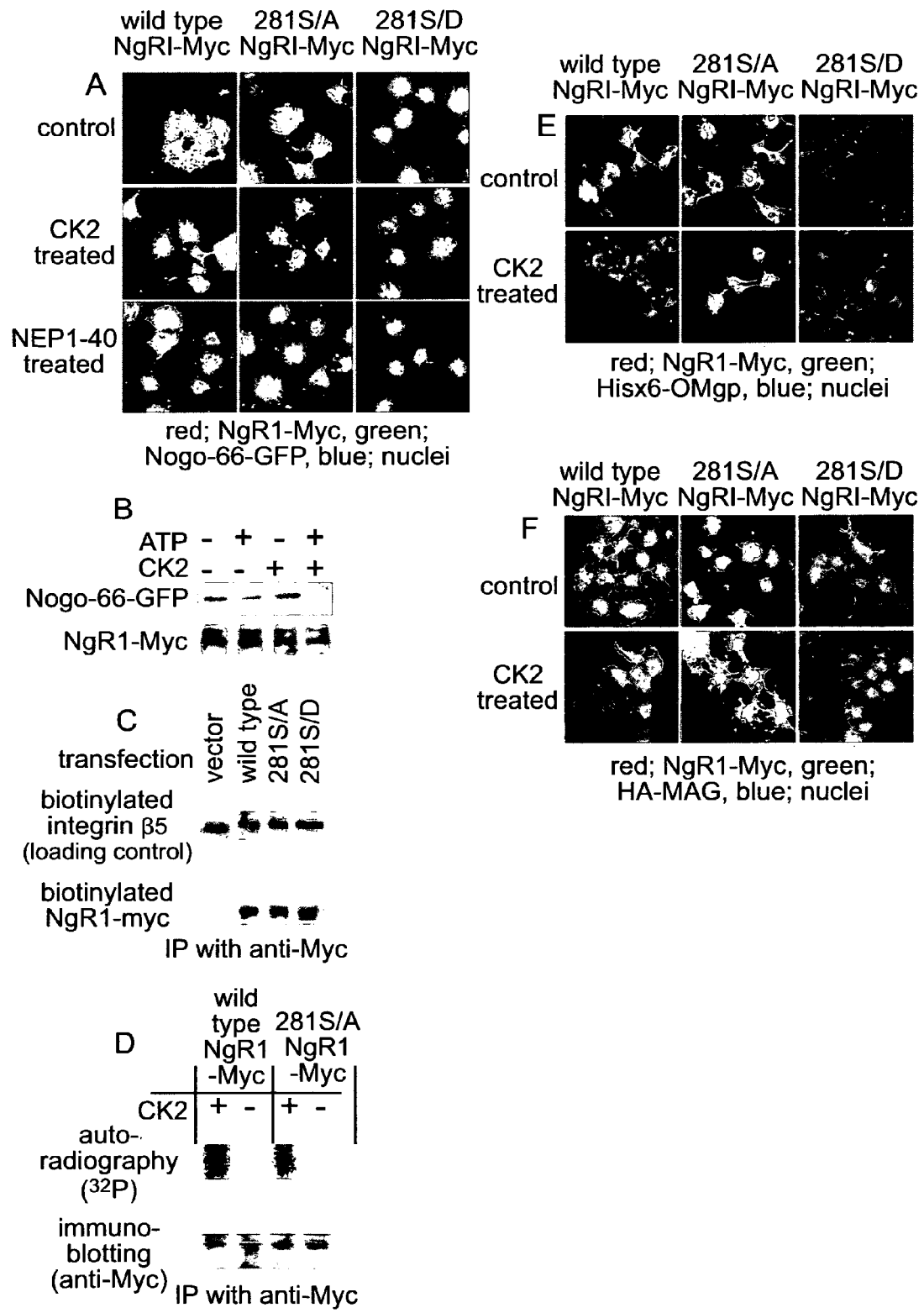

Figure 4

A
C-terminal flanking region of the leucine-rich repeats in NgR1

```
                    281
                     ▼
human    253 QYLRLNDNPWVCDCRARPLWAWLQKFRGSSSEVPCSLPQRLAGRDLKRLAANDLQGCAVATGP
mouse    253 QYLRLNDNPWVCDCRARPLWAWLQKFRGSSSEVPCNLPQRLADRDLKRLAASDLEGCAVASGP
rat      253 QYLRLNDNPWVCDCRARPLWAWLQKFRGSSSEVPCNLPQRLAGRDLKRLAASDLEGCAVASGP
danio    253 QYLRLNGNQWICDCRARPLWDWFKRFKGSSSDLECHLPASLNGKDLKRLKSDDLEGC-VDSPS
chicken  603 QYLRLNGNQWICDCQARSLWNWFKQFKGSSSELECHLPPHLAGRDLKRLQSSDLEGC-IDSFN
                                    PKA
                                    site         ☐ CK2 site
```

B
C-terminal flanking region of the leucine-rich repeats in NgR1, NgR2 and NgR3

```
                    281
                     ▼
hNgR1 253 QYLRLNDNPWVCDCRARPLWAWLQKFRGSSSEVPCSLPQRLAGRDLKRLAANDLQGCAVATGP
mNgR1 253 QYLRLNDNPWVCDCRARPLWAWLQKFRGSSSEVPCNLPQRLADRDLKRLAASDLEGCAVASGP
hNgR2 254 EFLRLNANPWACDCRARPLWAWFQRARVSSSDVTCATPPERQGRDLRALREADFQACP-PAAP
mNgR2 254 EFLRLNANPWACDCRARPLWAWFQRARVSSSDVTCATPPERQGRDLRALRDSDFQACP-PPTP
hNgR3 249 EFLRLNGNPWDCGCRARSLWEWLQRFRGSSSAVPCVSPGLRHGQDLKLLRAEDFRNCTGPASP
mNgR3 249 EFLRLNGNAWDCGCRARSLWEWLQRFRGSSSAVPCATPELRQGQDLKLLRVEDFRNCTGPVSP
                              PKA
                              site         ☐ CK2 site
```

C
CK2   - +
auto-
radiography
($^{32}$P)

immuno-
blotting
(NgR2-Myc)

D
control    CK2 treated

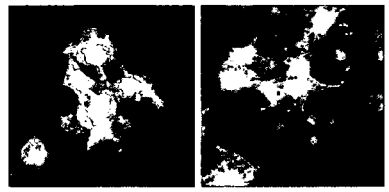

red; NgR2-Myc, green; HA-MAG, blue nuclei

E
phospho-peptide detected by mass spectrometry
human NgR2 281   VSSSDVTCATPPE

Figure 6

```
                    NF
human    1   MKRASAGGSRLLAWVLWLQAWQVAAPCPGACVCYNEPKVTTSCPQQGLQAVPVGIPAAS
mouse    1   MKRASSGGSRLLAWVLWLQAWRVATPCPGACVCYNEPKVTTSCPQQGLQAVPTGIPASS
rat      1   MKRASSGGSRLPTWVLWLQAWRVATPCPGACVCYNEPKVTTSCPQQGLQAVPTGIPASS
danio    1   MKTLIVEGGRLLCLMFWLNLVPVINSCPAKCVCYSEPKATVACQQQGLFSIPTEIPVRS
chicken  351 SARSLPEGSKLLILVLCLNIQSEVESCPGACVCYSEPKITISCQQQGLTAIPTEIPIQS
                  LRR1                 LRR2                 LRR3
human    60  QRIFLHGNRISHVPAASFRACRNLTILWLHSNVLARIDAAAFTGLALLEQLDLSDNAQL
mouse    60  QRIFLHGNRISHVPAASFQSCRNLTILWLHSNALARIDAAAFTGLTLLEQLDLSDNAQL
rat      60  QRIFLHGNRISYVPAASFQSCRNLTILWLHSNALAGIDAAAFTGLTLLEQLDLSDNAQL
danio    60  QRIFLQSNKLTVVRSTSFSSVHNLTVLWMYSNNISHIEAGAFYGLERLEELDIGDNSNL
chicken  410 QRIFLHNNKITLVRSTSFTSCRNMTILWIHSNNISLIEPGAFYGLNKLEELDLSDNTNL
                  LRR3                 LRR2                 LRR5
human    119 RSVDPATFHGLGRLHTLHLDRCGLQELGPGLFRGLAALQYLYLQDNALQALPDDTFRDL
mouse    119 HVVDPTTFHGLGHLHTLHLDRCGLRELGPGLFRGLAALQYLYLQDNNLQALPDNTFRDL
rat      116 RVVDPTTFRGLGHLHTLHLDRCGLQELGPGLFRGLAALQYLYLQDNNLQALPDNTFRDL
danio    119 RIISPTAFRGLTKLHTLHLHRCGLSELPVGVFRGLFSLQYLYLQDNNLLALHEDTFLDL
chicken  469 KSINPVTFRGLVHLHTLHLDRCGLMELSTGLFRGLFSLQYLYLQDNNLQNLLDDTFIDL
                  LRR5      LRR6                 LRR7                 LRR8
human    178 GNLTHLFLHGNRISSVPERAFRGLHSLDRLLLHQNRVAHVHPHAFRDLGRLMTLYLFAN
mouse    178 GNLTHLFLHGNRIPSVPEHAFRGLHSLDRLLLHQNHVARVHPFAFRDLGRLMTLYLFAN
rat      178 GNLTHLFLHGNRIPSVPEHAFRGLHSLDRLLLHQNHVARVHPHAFRDLGRLMTLYLFAN
danio    178 ANLTYLFLHNNKIKVVTDHMLRGLVNLDRLLLHQNRIVHVQQQAFNDLSKLTTLFLFFN
chicken  528 ANLTYLFLHGNKIKSLSENVFRGLINLDRLLLHQNRVSLVHRRSFHDLGKVMTLYLFNN
                  LRR8                            CF
human    237 NLSALPTEALAPLRALQYLRLNDNPWVCDCRARPLWAWLQKFRGSSSEVPCSLPQRLAG
mouse    237 NLSMLPAEVLMPLRSLQYLRLNDNPWVCDCRARPLWAWLQKFRGSSSEVPCNLPQRLAD
rat      237 NLSMLPAEVLVPLRSLQYLRLNDNPWVCDCRARPLWAWLQKFRGSSSEVPCNLPQRLAG
danio    237 NLTMLTGESMNPLVSLQYLRLNGNQWICDCRARPLWDWFKRFKGSSSDLECHLPASLNG
chicken  587 NLTVLTGETMAPLVSLQYLRLNGNQWICDCQARSLWNWFKQFKGSSSELECHLPPHLAG
                        CF
human    296 RDLKRLAANDLQGCAVATGPYHPIWTGR--------ATDEEPL----GLPKCCQPDAAD
mouse    296 RDLKRLAASDLEGCAVASGPFRPIQTSQ--------LTDEELL----SLPKCCQPDAAD
rat      296 RDLKRLAASDLEGCAVASGPFRPFQTNQ--------LTDEELL----GLPKCCQPDAAD
danio    296 KDLKRLKSDDLEGC-VDSPSQVQTSIFNSKVHSGKFLSLDDPL--VESIPRCCLSD-ND
chicken  646 RDLKRLQSSDLEGC-IDSFNQIRTSVFSTKTRSGKLATGSPPLSSHDGSMKCCQPE-MD
human    343 KASVLEPGRPASAGNALKGRVPPGDSPPGNGSGPRHINDSPFGTLPGSAEPPLTAVRPE
mouse    343 KASVLEPGRPASAGNALKGRVPPGDTPPGNGSGPRHINDSPFGTLPSSAEPPLTALRPG
rat      343 KASVLEPGRPASVGNALKGRVPPGDTPPGNGSGPRHINDSPFGTLPGSAEPPLTALRPG
danio    351 KSSIISSKSIPDPSSYNSRQITNNPLKEKENISKTKFREVERTKNETRNKQSLNDGPLG
chicken  703 KSFIYEAKGKAGPSSHSSRPSSNNPLKDKENMSKTKYVETDPSKNG-SNKQ-INDSPFG
human    402 GSEPPGF--------------PTSGP-RRRPGCSRKNRTRSHCRLGQAGSGGGGTGDS
mouse    402 GSEPPGL--------------PTTGP-RRRPGCSRKNRTRSHCRLGQAGSGASGTGDA
rat      402 GSEPPGL--------------PTTGP-RRRPGCSRKNRTRSHCRLGQAGSGSSGTGDA
danio    410 TMSNNLDQSLDRIDPELLGNLEPSTAPTKKKKKCSKKPKSDQNCLKG------------
chicken  764 FPIVDPPLTKLR--PEFLEPIEPSTVPTKKRQGCSKKNKSKAQCRLTQQG---------
human    445 EGSGALPSLTCSLTPLGLALVLWTVLGPC
mouse    445 EGSGALPALACSLAPLGLALVLWTVLGPC
rat      445 EGSGALPALACSLAPLGLALVLWTVLGPC      □ CK2 target site (T/S X X D/E)
danio    457 HGST-IQVLA----VIFLPLF-WLSLALS
chicken  810 NSST-LQLSLTSL-LISPPLV-WSLLLLC
``` rat: AF 462390, human; NM 023004, mouse; NM 022982,
danio; NM 203478, chicken; XM 415292

Figure 8

```
NgR1    1    MKRAS----AGGSRLLAWVLWLQAWQVAAPCPGACVCYNEPKVTTSCPQQGLQAVPVGIP
NgR2    1    MLPGLRRLLQAPASACLLLMLLALPLAAPSCPMLCTCYSSP-PTVSCQANNFSSVPLSLP
Ngr3    1    MLR------KGCCVELLLLLVAAELPLGGGCPRDCVCYPAP-MTVSCQAHNFAAIPEGIP

NgR1   57    AASQRIFLHGNRISHVPAASFRACRNLTILWLHSNVLARIDAAAFTGLALLEQLDLSDNA
NgR2   60    PSTQRLFLQNNLIRTLRPGTFG--SNLLTLWLFSNNLSTIYPGTFRHLQALEELDLGDNR
Ngr3   54    VDSERVFLQNNRIGLLQPGHFS--PAMVTLWIYSNNITYIHPSTFEGFVHLEELDLGDNR

NgR1  117    QLRSVDPATFHGLGRLHTLHLDRCGLQELGPGLFRGLAALQYLYLQDNALQALPDDTFRD
NgR2  118    HLRSLEPDTFQGLERLQSLHLYRCQLSSLPGNIFRGLVSLQYLYLQENSLLHLQDDLFAD
Ngr3  112    QLRTLAPETFQGLVKLHALYLYKCGLSALPAGVFGGLHSLQYLYLQDNHIEYLQDDIFVD

NgR1  177    LGNLTHLFLHGNRISSVPERAFRGLHSLDRLLLHQNRVAHVHPHAFRDLGRLMTLYLFAN
NgR2  178    LANLSHLFLHGNRLRLLTEHVFRGLGSLDRLLLHGNRLQGVHRAAFRGLSRLTILYLFNN
Ngr3  172    LVNLSHLFLHGNKLWSLGPGTFRGLVNLDRLLLHENQLQWVHHKAFHDLRRLTTLFLFNN

NgR1  237    NLSALPTEALAPLRALQYLRLNDNPWVCDCRARPLWAWLQKFRGSSSEVPCSLPQRLAGR
NgR2  238    SLASLPGEALADLPSLEFLRLNANPWACDCRARPLWAWFQRARVSSSDVTCATPPERQGR
Ngr3  232    SLSELQGECLAPLGALEFLRLNGNPWDCGCRARSLWEWLQRFRGSSSAVPCVSPGLRHGQ

NgR1  297    DLKRLAANDLQGCAVATGPYHPIWTGRATDEEPLGLPKCCQPDAADKASVLEPGRPASAG
NgR2  298    DLRALREADFQACP-PAAPTR-PGSRARGNSS------SNHLYGVAEA----GAPPADPS
Ngr3  292    DLKLLRAEDFRNCTGPASPHQ-IKSHTLTTTDRAARKEHHSPHGPTRS----KGHPHGPR

NgR1  357    NALKGRVPPGDSPPGNGSGPRHINDSPFGTLPGSAEPPLTAVRPEGSEPPGFPTSGPRRR
NgR2  346    TLYR------DLPAEDSRGRQ-------GGDAPTEDDYWGGYG-----------GEDQRG
Ngr3  347    PGHR----KPGKNCTNPRNRNQISKAGAGKQAPELPDYAPDYQHKFSFDI-MPTARPKRK

NgR1  417    PGCSRKNRTRSHCRLGQAGSGGGGTGDSEGSALPSLTCSLTPLGLALVLWTVLGPC
NgR2  382    EQMCPGAACQAPPDSRGP---------ALSAGLPSPLLCLLLLVPHHL
Ngr3  402    GKCARRTPIRAPSGVQQA---------SSASSLGASLLAWTLGLAVTLR
```

☐ CK2 target site (T/S X X D/E)

A

B

| | | | |
|---|---|---|---|
| mPirB | 418 | SGLSKKPSLLTHQGHILDPGMTLTLQCF | NM011095 |
| hLILRB1 | 220 | LGVSKKPSLSVQPGPIVAPEETLTLQCG | NM000669 |
| hLILRB2 | 219 | PGVSKKPSLSVQPGPVVAPGESLTLQCV | NM005874 |
| hLILRB3 | 219 | SGVSRKPSLLTLQGPVLAPGQSLTLQCG | NM001081450 |
| hLILRB5 | 219 | PGVSRKPSLLIPQGSVVARGGSLTLQCR | NM001081442 |
| rPirB | 417 | SGPSRKPSLLSHQGHILEPGMSLTLQCY | NM001037357 |

COMPOSITIONS AND METHODS FOR CAUSING NEURITE OUTGROWTH

The present application is filed pursuant to 35 U.S.C. 371 as a U.S. National Phase application of International Patent Application No. PCT/GB2010/000391, which was filed Mar. 5, 2010, claiming the benefit of priority to British Patent Application No. GB 0903913.2, which was filed on Mar. 6, 2009. The entire text of the aforementioned applications is incorporated herein by reference in its entirety.

FIELD OF THE INVENTION

The invention relates to the field of neurological injury or disease, in particular the invention relates to the alleviation of inhibition of neuronal regeneration, such as neurite outgrowth.

BACKGROUND TO THE INVENTION

Neurons extend neurites to communicate with other neurons or with their target tissues. This neuronal network in the adult central nervous system (CNS) regenerates only poorly after injury. This is a problem in the art, leading to poor patient outcomes following injury to the neuronal network.

Failure of the adult mammalian CNS to regenerate is due partly to the neurite outgrowth inhibitors associated with damaged myelin. Myelin-associated glycoprotein (MAG), Nogo-A (also known as Reticulon 4A) and oligodendrocyte myelin glycoprotein (OMgp) are myelin-associated inhibitors of neurite outgrowth that can bind to Nogo receptor 1 (NgR1). These myelin-associated proteins, Nogo-A, MAG and OMgp, transmit signals from oligodendrocytes into neurons through binding Nogo receptors. This Nogo signalling has critical roles in development and maintenance of the central nervous system (CNS). It can inhibit differentiation, migration, and neurite outgrowth of neurons, causing poor recovery of the adult CNS from damage.

Nogo-A binds to NgR1 through a domain called Nogo-66. The Nogo-66 domain is composed of 66 amino acids and the Nogo-66 domain alone, without other regions of Nogo-A, is sufficient to inhibit neurite outgrowth. MAG, but neither Nogo-A nor OMgp, can inhibit neurite outgrowth not only through NgR1 but also through NgR2, an NgR1 homologous protein (6).

NgR1 makes signalling complexes containing LINGO-1 and either $p75^{NTR}$ or TAJ/TROY (McGee, and Strittmatter *Trends Neurosci* 26, 193-198 (2003); Schwab et al. *Trends Mol Med* 12, 293-297 (2006)). Both $p75^{NTR}$ and TAJ/TROY belong to the TNFalpha receptor family and they are proposed to be the major components initiating intracellular signals for inhibition of neurite outgrowth. It is uncertain whether NgR2 makes complexes containing LINGO-1 and either $p75^{NTR}$ or TAJ/TROY.

While information on the roles of Nogo signalling is expanding, information on the mechanisms controlling this signalling is limited. This is a problem in the art. Increased intracellular levels of cAMP are known to overcome the inhibitory effects of Nogo signalling on neurite outgrowth (16). However, the detailed mechanism by which cAMP overcomes the effects of Nogo signalling is unknown.

BDNF, a member of the neurotrophin nerve growth factor family, not only stimulates neurite outgrowth of several types of neural cells in vitro (17-19, 20), but also partially promotes the recovery from spinal cord injury (21-24). Pre-treatment with BDNF increases the levels of intracellular cAMP in cultured neurons, allowing neurons to extend neurites even in the presence of the myelin-associated inhibitors (25). Furthermore, BDNF is implicated in injury-induced neurite sprouting in the hippocampus (26). These reports suggest that BDNF could potentially help regeneration of neuronal networks in the CNS even in the presence of the myelin-associated inhibitors of neurite outgrowth. However, the effect is limited and is not enough for complete regeneration of the neural networks.

A human neuroblastoma cell line SH-SY5Y shows BDNF-dependent neurite outgrowth after 5 days treatment with retinoic acid (RA) (18). SH-SY5Y cells initiate differentiation into neuron-like cells and start expression of neuron-specific proteins in response to RA. However, the neural cells differentiated from SH-SY5Y cells by RA show only limited morphological changes. BDNF treatment is required for efficient neurite outgrowth of the SH-SY5Y-derived neural cells, otherwise longer treatment with RA is required (27). Caesin kinase II (CK2) has been studied in the context of neurones. Caesin kinase II has been implicated in the phosphorylation of two different surface proteins in neurones. Neither protein is related to Nogo receptors. Furthermore, the studies in this area have been entirely dependent on the use of inhibitors of caesin kinase II. Thus, the function of intra-cellular CK2 has been studied in the art. Intra-cellular CK2 activity is known to be required for neurite outgrowth itself. Extra-cellular CK2 is known to exist. However, information on extra-cellular CK2 is largely unknown as noted above. In more detail, there are indications that amyloid beta precursor protein and neuroglican C can be phosphorylated at the surfaces of neurones by endogenous extra-cellular CK2. However, the effects of these phosphorylation(s) on neurite outgrowth (if any) are unknown.

Caesin kinase II has been used to treat collagen/laminin in certain in vitro preparations. These treatments have never involved cells. These treatments have only ever involved in vitro preparations of matrix proteins such as collagen or laminin.

No caesin kinase II treatment of cells is known in the prior art. Application of exogenous caesin kinase II to cells is not known in the prior art.

Ulloa et al (1993 EMBO vol 12 pp 1633-1640) inhibited CK2 activity in N2A mouse neuroblastoma cell line with antisense oligos and with a specific inhibitor. N2A cells extend neurites with neither retinoic acid (RA) nor BDNF. Using an N2A cell line, they found that neurite outgrowth from N2A cells is inhibited by depletion of CK2, and that phosphorylation of a microtuble-associated protein, MAP1B, is changed by the depletion. MAP is required for rearrangement of cytoskeleton, which is required for neurite outgrowth. Thus, they concluded that the change of MAP1B phosphorylation causes inhibition of neurite outgrowth by CK2 depletion. MAP1B phosphorylation is intra-cellular. Other proteins associated with rearrangement of cytoskeleton have been known to be phosphorylated by CK2, intra-cellularly. These intra-cellular phosphorylation events are required for neurite outgrowth itself. Since normal neurones, as well as N2A cells, can extend neurites without any stimulation, the inference is that these intra-cellular phosphorylation events are catalysed by a basal level of intro-cellular CK2 in neurones. The paper is not related to Nogo signaling.

No relationship between phosphorylation and Nogo signaling is known to date. The mechanism controlling Nogo signalling is unknown to date.

The present invention seeks to overcome problem(s) associated with the prior art.

SUMMARY OF THE INVENTION

It is a problem that adult nervous tissue regenerates only poorly, or not at all. This is a particular problem following damage caused by factors such as injury or disease. Various mechanisms governing inhibition of regeneration have been identified. One such mechanism is inhibition of neurite outgrowth by signalling through the Nogo receptors. Although various ligands and receptors in this pathway are well characterised, there has been no reliable way of alleviating this inhibition disclosed in the prior art.

The present inventors have addressed these problems. Through detailed studies of Nogo signalling, the inventors have identified ways in which said signalling can be inhibited. Moreover, the inventors have identified a specific molecular target within the Nogo receptor which is key to the regulation of Nogo signalling. This target is serine 281 of the Nogo receptor. Phosphorylation of this residue abolishes binding of inhibitors of neurite outgrowth to the receptor, thereby alleviating the inhibition of neuroregeneration. Furthermore, the inventors teach and demonstrate effective ways in which this may be accomplished, such as by treatment with protein kinase A and/or caesin kinase II. The invention is based upon these surprising findings.

Thus, in one aspect the invention provides a method for alleviating the inhibition of neurite outgrowth from a neurone,
wherein said neurone comprises a Nogo receptor,
said method comprising contacting said neurone with a composition capable of causing phosphorylation of a Nogo receptor, wherein said composition comprises protein kinase A or casein kinase II.

Suitably said composition comprises protein kinase A and casein kinase II.

Suitably said phosphorylation is phosphorylation of an amino acid residue corresponding to serine 281 of said Nogo receptor.

Suitably said Nogo receptor is human NgR1.

In another aspect, the invention relates to use of a protein kinase A polypeptide for the manufacture of a medicament for spinal cord injury.

In another aspect, the invention relates to protein kinase A polypeptide for use in the treatment of spinal cord injury.

In another aspect, the invention relates to use of a caesin kinase II polypeptide for the manufacture of a medicament for spinal cord injury.

In another aspect, the invention relates to caesin kinase II polypeptide for use in the treatment of spinal cord injury.

In another aspect, the invention relates to a composition comprising protein kinase A and casein kinase II, for use as a medicament.

In another aspect, the invention relates to use of a composition as described above for the manufacture of a medicament for spinal cord injury.

In another aspect, the invention relates to a composition as described above for use in the treatment of spinal cord injury.

In another aspect, the invention relates to use of a protein kinase A polypeptide or a caesin kinase II polypeptide for the manufacture of a medicament for causing neurite outgrowth.

In another aspect, the invention relates to a protein kinase A polypeptide or a caesin kinase II polypeptide for use in causing neurite outgrowth.

In another aspect, the invention relates to a method of treating spinal cord injury in a subject, said method comprising administering to said subject an effective amount of a composition capable of causing phosphorylation of a Nogo receptor, wherein said composition comprises protein kinase A or casein kinase II. Suitably said administration is localised to the site of the injury.

DETAILED DESCRIPTION OF THE INVENTION

Nogo signalling can inhibit neurite outgrowth (3, 4), differentiation (9, 10), migration (12) and synapse formation (11) of neurons in the CNS. Thus, Nogo signalling has been identified as a major inhibitor of the regeneration of the CNS, which does not occur under physiological condition.

We disclose that phosphorylation of Nogo receptors, e.g. by casein kinase II (CK2), inhibits binding of the myelin-associated proteins which inhibit neuronal regeneration such as neurite outgrowth. We demonstrate that brain-derived neurotrophic factor (BDNF) may optionally be used to induce the phosphorylation of Nogo receptor, which suppresses Nogo-dependent inhibition of neurite outgrowth from neuroblastoma-derived neurons. In further embodiments, extra-cellular CK2 treatment overcomes inhibition of neurite outgrowth by the myelin-associated proteins. This is demonstrated for example in rat adult neurons. Thus the invention provides new strategies to control Nogo signalling and hence neuronal regeneration.

We disclose for the first time a relationship between phosphorylation and Nogo signalling. We disclose for the first time the effect of ecto-domain phosphorylation on Nogo-dependent inhibition of neurite outgrowth. Phosphorylation of Nogo receptors may not be required for neurite outgrowth itself, but it is required for overcoming inhibition of neurite outgrowth. The inhibition of neurite outgrowth occurs under in vivo conditions, eg. after traumatic injury of the central nervous system.

Moreover, we show that Nogo signalling inhibits neurite outgrowth from mammalian cells such as SH-SY5Y-derived neural cells, and that the inhibition is suppressed by extra-cellular treatment with CK2 without BDNF. CK2 treatment inhibits binding of Nogo-66, MAG and OMgp to their receptors, allowing neurite outgrowth in the presence of these neurite outgrowth inhibitors. Thus we advantageously show BDNF-independent effects of the invention. Suitably BDNF is not used in the methods of the invention. Suitably BDNF is specifically omitted from the methods of the invention. Suitably the compositions of the invention do not comprise BDNF.

DEFINITIONS

The term 'comprises' (comprise, comprising) should be understood to have its normal meaning in the art, i.e. that the stated feature or group of features is included, but that the term does not exclude any other stated feature or group of features from also being present.

Nogo Receptors

In a broad sense, "Nogo Receptors" may refer to any protein mediating Nogo-dependent inhibition of neurite outgrowth, and need not specifically refer only to receptors (NgRs) in the classic membrane-localised sense, but may also refer to any Nogo-binding protein mediating the Nogo signalling e.g. via proteins other than NgR family members; indeed, our results with normal neurones show that CK2 treatment can block such NgR-independent Nogo signalling as well as NgR-dependent signalling. However, suitably the term "Nogo Receptors" may be given its conventional meaning in the art herein unless the context indicates otherwise.

NgR1 and its homologous proteins, NgR2 and NgR3, belong to a family of glycosylphosphatidylinositol (GPI)-linked proteins with eight leucine-rich repeat regions, which do not have intracellular domains. While NgR1 can interact with Nogo-A, MAG and OMgp, NgR2 interacts with only MAG in a sialic acid-dependent manner. This interaction can inhibit neurite outgrowth, too. The ligand for NgR3 is unknown.

NgR1 makes a complex involving LINGO-1 and neurotrophin receptor $p75^{NTR}$. Alternatively, TAJ/TROY, an orphan tumour necrosis factor receptor family member broadly expressed in neurones, is involved in the complex, instead of p75$^{NTR}$. It is unknown whether NgR2 can make a complex with LINGO-1, p75$^{NTR}$ or TAJ/TROY, as seen for NgR1.

Thus, Nogo signalling can be initiated by at least three ligands in oligodendrocytes, and it can transduce signals into neurones through at least two receptors. Relative contributions of specific ligand-receptor systems in Nogo signalling to inhibition of neurite outgrowth may vary among different neuronal cell types.

The present invention is concerned with Nogo receptors present on the cell surface. Indeed, it is a specific teaching of the invention that exogenous substances are used to provoke phosphorylation of Nogo receptors on the cell surface of the target cell. Thus, the term "Nogo receptor" as used herein suitably refers to a Nogo receptor protein present at the cell surface of a target cell. Suitably the target cell is a vertebrate target cell, more suitably a mammalian target cell, most suitably a human target cell. In some embodiments the target cell is most suitably a human cell comprised by the subject to be treated, such as a human neurone, such as an adult human neurone.

In a broad aspect, the term "Nogo receptor" may refer to the polypeptide of any of the known Nogo receptors, such as NgR1, NgR2 or NgR3. Moreover, in targeting the Nogo receptor, it may be that more than one type of Nogo receptor is phosphorylated. This may bring advantages to the invention, such as alleviation of inhibition of neurite outgrowth independent of the particular Nogo receptor type or types which happen to be expressed on the particular target cell of choice. Moreover, it may be that by targeting a multiplicity of Nogo receptor proteins, that a stronger and/or faster effect is achieved.

It is important to note that each of the Nogo receptors possesses the conserved serine at amino acid residue 281. Thus, references to Nogo receptor mutants according to the invention may equally embrace any of the known NgR polypeptides, provided of course they have the specific mutation or substitution being discussed.

Suitably, a Nogo receptor according to the invention is one or more of NgR1, NgR2 or NgR3 or NgR3. More suitably, a Nogo receptor according to the invention is one or more of NgR1 or NgR2. An advantage of this is that these Nogo receptors are better characterised, and are therefore amenable to the production of more specific or defined effects in vivo. Most preferably, a Nogo receptor according to the present invention is NgR1. This has numerous advantages, some of which are set out in the examples section.

The invention is primarily concerned with vertebrate, such as mammalian applications. Therefore, suitably the Nogo receptor of the invention is a vertebrate, such as mammalian Nogo receptor. Most suitably, the Nogo receptor of the invention is a human Nogo receptor. A human Nogo receptor has a polypeptide sequence corresponding to the human Nogo receptor amino acid sequence. Naturally, a Nogo receptor polypeptide according to the invention may be produced by any suitable means, such as recombinant production from a non-human host cell. However, for ease of understanding, a Nogo receptor polypeptide produced from a non-human cell will be regarded as a human Nogo receptor if the amino acid sequence corresponds to the human amino acid sequence.

Nogo receptor mutants are disclosed and discussed herein. It will be appreciated from the above discussion that such mutants may comprise one of a number of individual Nogo receptor subtypes such as NgR1, NgR2, NgR3, etc. For ease of understanding, particular amino acids or particular mutations are discussed in the context of a Nogo receptor reference sequence.

Reference Sequence

It will be appreciated that particular amino acid residues will be discussed using their numeric address on the polypeptide, as is conventional in the art. When particular amino acid residues are referred to using numeric addresses, the numbering is taken using the amino acid sequence of human NgR1 as the reference sequence. Most suitably, the Nogo receptor reference sequence is human NgR1 amino acid sequence of NM023004:

```
MKRASAGGSRLLAWVLWLQAWQVAAPCPGACVCYNEPKVTTSCPQQGLQ

AVPVGIPAASQRIFLHGNRISHVPAASFRACRNLTILWLHSNVLARIDA

AAFTGLALLEQLDLSDNAQLRSVDPATFHGLGRLHTLHLDRCGLQELGP

GLFRGLAALQYLYLQDNALQALPDDTFRDLGNLTHLFLHGNRISSVPER

AFRGLHSLDRLLLHQNRVAHVHPHAFRDLGRLMTLYLFANNLSALPTEA

LAPLRALQYLRLNDNPWVCDCRARPLWAWLQKFRGSSSEVPCSLPQRLA

GRDLKRLAANDLQGCAVATGPYHPIWTGRATDEEPLGLPKCCQPDAADK

ASVLEPGRPASAGNALKGRVPPGDSPPGNGSGPRHINDSPFGTLPGSAE

PPLTAVRPEGSEPPGFPTSGPRRRPGCSRKNRTRSHCRLGQAGSGGGGT

GDSEGSGALPSLTCSLTPLGLALVLWTVLGPC
```

This is to be used as is well understood in the art to locate the residue of interest. This is not always a strict counting exercise—attention must be paid to the context. For example, if the protein of interest such as human EHD2 is of a slightly different length, then location of the correct residue in the human sequence corresponding to (for example) S281 may require the sequences to be aligned and the equivalent or corresponding residue picked, rather than simply taking the 281st residue of the sequence of interest. This is well within the ambit of the skilled reader. Exemplary alignments are provided in the accompanying figures.

It will be apparent to the skilled reader that the invention is exemplified predominantly by reference to NgR1. It should be noted that NgR1 exhibits high sequence homology with other NgR family polypeptides. Thus, in some aspects the invention relates to the use of NgR1 in the development of therapeutics for application to other NgR family proteins.

In some aspects of the invention, it may be desirable to employ a functional test as to whether or not a particular polypeptide is to be considered an NgR family polypeptide. In addition to, or instead of, the sequence based criteria set out above, the following functional criterion may also be used: binding to ligands such as those noted herein. Moreover, capacity to function in a neurite outgrowth assay may also be used, such as by overexpression in SH-SY5Y cells with RA treatment as described in the examples. Thus, in order to determine whether or not a particular polypeptide is indeed to be considered an NgR family polypeptide, it may be tested whether or not that polypeptide functions in a neurite outgrowth assay. If the NgR protein supports Nogo signalling in this context, the polypeptide may be regarded as a Nogo receptor (NgR family polypeptide). Of course the aim of the invention is to alleviate inhibition of neurite outgrowth and this should be borne in mind when assessing NgR protein(s)—it is the wild-type proteins which inhibit neurite outgrowth in this assay, in particular when not treated with kinase according to the invention.

Nogo Receptor Mutants of the Invention

The invention relates to Nogo receptor polypeptides characterised in that serine 281 is substituted for any other amino acid other than serine. Suitably S281 is substituted for a non-phosphoacceptor amino acid, so that suitably S281 is not S, T, or Y.

Suitably the invention provides a NogoR having S281A. This has the advantage of being unphosphorylatable at this site. This means that the receptor has the biological property of being resistant to CKII/PKA inhibition of ligand binding. In other words, such a mutant possesses the novel function of signalling in response to Nogo ligand(s) even in the presence of CKII/PKA.

Suitably the invention provides a NogoR having S281D. This has the advantage of simulating phosphorylation at S281. This means that the receptor has the biological property of being permanently switched 'off' so that the inhibition of neurite outgrowth is permanently alleviated using this receptor. More specifically, this receptor does not bind Nogo ligand(s). In other words, such a mutant possesses the novel function of NOT binding (or signalling) in response to Nogo ligand(s), regardless of the presence of CKII/PKA.

Suitably the Nogo receptor polypeptides (NogoR's) of the invention comprise the sequence of NMO23004 except where indicated, e.g. at the residue corresponding to S281.

The invention also relates to NogoR's having at least 60% identity to NMO23004, suitably at least 70% identity to NMO23004, suitably at least 75% identity to NMO23004, suitably at least 80% identity to NMO23004, suitably at least 85% identity to NMO23004, suitably at least 90% identity to NMO23004, suitably at least 95% identity to NMO23004, suitably at least 97% identity to NMO23004, suitably at least 98% identity to NMO23004, suitably at least 99% identity to NMO23004, always with the feature that residue S281 is other than serine.

Truncated forms suitably correspond to this sequence across the length of such a truncated form. Suitably a NogoR polypeptide according to the present invention comprises at least 30 amino acids, suitably at least 80 amino acids, suitably at least 130 amino acids, suitably at least 180 amino acids, suitably at least 230 amino acids, suitably at least 280 amino acids, suitably at least 330 amino acids, suitably at least 380 amino acids, suitably at least 382 amino acids (e.g. full length NgR2), suitably at least 402 amino acids (e.g. full length NgR3), suitably at least 417 amino acids (e.g. NgR1).

Polypeptides and Mutants

Nogo receptor sequences may be modified for use in the present invention. Typically, modifications are made that maintain the region of the sequence comprising serine 281 (or the substitution at said address). Amino acid substitutions may be made, for example from 1, 2 or 3 to 10, 20 or 30 substitutions provided that the modified sequence retains the required S281 residue. Amino acid substitutions may include the use of non-naturally occurring analogues, for example to increase half-life of a therapeutically administered polypeptide. The same applied to PKA or CKII polypeptides of the invention, in which case it is always required that the PKA/CKII kinase activity is retained following any mutants or substitutions introduced.

Conservative substitutions may be made, for example according to the Table below. Amino acids in the same block in the second column and preferably in the same line in the third column may be substituted for each other:

| ALIPHATIC | Non-polar | G A P |
| --- | --- | --- |
|  |  | I L V |
|  | Polar - uncharged | C S T M |
|  |  | N Q |
|  | Polar - charged | D E |
|  |  | K R |
| AROMATIC |  | H F W Y |

Proteins of the invention are typically made by recombinant means, for example as described below. However they may also be made by synthetic means using techniques well known to skilled persons such as solid phase synthesis. Proteins of the invention may also be produced as fusion proteins, for example to aid in extraction and purification. Examples of fusion protein partners include glutathione-S-transferase (GST), 6×His, GAL4 (DNA binding and/or transcriptional activation domains) and β-galactosidase. It may also be convenient to include a proteolytic cleavage site between the fusion protein partner and the protein sequence of interest to allow removal of fusion protein sequences.

Proteins of the invention may be in a substantially isolated form. It will be understood that the protein may be mixed with carriers or diluents which will not interfere with the intended purpose of the protein and still be regarded as substantially isolated. A protein of the invention may also be in a substantially purified form, in which case it will generally comprise the protein in a preparation in which more than 90%, e.g. 95%, 98% or 99% of the protein in the preparation is a protein of the invention.

Applications of the Invention

It will be noted by the skilled reader that the invention relates to a novel method of inhibiting Nogo signalling. This novel method involves the phosphorylation of the Nogo receptor. Techniques disclosed herein also involve Nogo receptor mutants. Clearly, each of these slightly different technical variations is a part of the same common invention concerned with inhibition of Nogo signalling. For convenience and ease of understanding, the invention has been principally described in connection with alleviating or reducing the inhibition of neurite outgrowth. This finds particular application in fields such as spinal cord injury. However, broader aspects of the invention may involve manipulation of other properties of neurones such as their migration or differentiation. Indeed, in principle any process being controlled or affected by Nogo signalling (such as inhibition of neurite outgrowth, such as migration of neurones, or such as any other biological phenomenon influenced by Nogo signalling) may be modulated or controlled using techniques disclosed herein such as phosphorylation of the Nogo receptor.

Without wishing to be bound by theory, the precise biomechanics of neurite outgrowth are still a subject of active research. It may be that the Nogo signalling techniques disclosed herein are affecting the regulation of neurite outgrowth in the sense of affecting controlling signals, or it may be that they are affecting the neurite outgrowth machinery such as proteins involved in fibre formation which may be intimately involved in producing the effect of neurite outgrowth. The present invention does not concern itself with the precise biomechanics of neurite outgrowth. It is a key teaching of the invention that manipulation of the phosphorylation state of the Nogo receptor, or indeed the use of specific Nogo receptor mutants disclosed herein, are useful in modulation of neurite outgrowth. This teaching, and ways in which the invention is put into practice, are typically independent of the precise molecular mechanism which takes place at the point of physical neurite outgrowth itself.

A key application of the invention is in the treatment of spinal cord injury. In particular, the invention finds application in promotion of regeneration following spinal cord injury. Specifically, the invention is useful if alleviating or reducing the inhibition of neurite outgrowth which is caused by signalling via the Nogo receptor. By suppressing or reducing signalling via the Nogo receptor, inhibition of neurite outgrowth is usefully diminished. This provides conditions which are advantageously permissive of neurite outgrowth and therefore of regeneration.

Numerous examples presented herein involve canulation of the subject for application of the compositions of the invention. It should be noted that when the subject being treated is a human, canulation is advantageously avoided. Rather than canulation, a topical injection or series of injections of the compositions of the invention would be suitably employed.

In vivo applications are demonstrated in the examples section. In overview, the invention is generally applicable as follows:

add ng to μg of kinase such as CK2, optionally with 100 μM ATP, after injury eg. of the spinal cord In an experimental system, an injury may be made in the spinal cord and a canule put at the lesion. Through this canule, kinase such as CK2 may be applied on the area. It is also possible to apply kinase such as CK2 with injection, without canulation. This is preferred for human subjects. However, for experimental systems, canulation makes it easier to add kinase such as CK2 from time to time.

It may then be examined whether neurite sprouting is observed or not, for example with immunofluorescence of tissue section.

Following observation of sprouting, behaviour tests may be conducted to assess functional recovery.

Suitably CK2 alone may be used, or CK2 in combination with chondroitinase ABC, which can digest chondroitin sulphate, another inhibitor of CNS regeneration.

Suitably PKA may be used, or PKA in combination with chondroitinase ABC.

Suitably the methods of the invention may be in vitro.

Suitably the methods of the invention may be in vivo for example in treatment of a subject such as a human subject.

Phosphorylation of the Nogo Receptor

It is envisaged that the majority of practical applications or embodiments of the invention will affect signalling of the Nogo receptor via inducing its phosphorylation. Embodiments of the invention involving Nogo receptor mutants are discussed herein below. However, turning to the consideration of phosphorylation of the Nogo receptor, the inventors have surprisingly identified a particular site within the Nogo receptor which mediates the advantageous effects of the invention. This site is serine 281 of the Nogo receptor.

The inventors turned their attention to the study of serine 281 and the surrounding amino acid residues. A range of experimental techniques, including sequence analysis as well as direct experimentation as presented in the accompanying examples, were used in order to validate this surprising finding.

One of the key insights disclosed by the present inventors is that serine 281 of the Nogo receptor is of paramount importance as a target for the present invention. Moreover, the inventors have disclosed a number of ways in which serine 281 of the Nogo receptor can be targeted and phosphorylated. Two of the most suitable ways of accomplishing this are the use of protein kinase A and/or caesin kinase II to directly phosphorylate serine 281 of the Nogo receptor. Thus, although protein kinase A and caesin kinase II are not necessarily physically related to one another, in the context of the present invention they form a single cohesive technical group of alternative ways in which the invention can be implemented. In other words, caesin kinase II and protein kinase A represent two equally valid ways of implementing the same single invention. Thus, the presence of these two structurally distinct alternatives in the appended claims is entirely consistent with a single inventive concept. Moreover, these two enzymes share the same technical benefit in the context of the invention, which is namely to catalyse the phosphorylation of serine 281 of the Nogo receptor. For at least these reasons, the application can be clearly seen to relate to a single inventive concept. Diverse ways of achieving the technical benefits of the invention are described in order to assist understanding, and in order to ensure that the skilled reader has no difficulty in the practice of the invention.

Serine 281

As noted above, it is an important part of the core inventive concept that the different technical ways in which the invention may be implemented are in fact each directed at producing the same technical effect, ie, phosphorylation of serine 281 of the Nogo receptor. In the course of their studies, the inventors found that this residue is part of a predicted phosphate acceptor site for both CK2 and PKA. Furthermore, this key finding has been backed up by experimental research which demonstrates that both CK2 and PKA both catalyse the phosphorylation of this important residue, and therefore produce the alleviation of inhibition of neurite outgrowth.

Caesin Kinase II

Suitably caesin kinase II is vertebrate, more suitably mammalian caesin kinase II. More suitably, caesin kinase II is human caesin kinase II.

Caesin kinase II most commonly occurs as a hetero-tetramer. This hetero-tetramer typically comprises a catalytic sub-unit consisting of two alpha polypeptides, and a regulatory sub-unit consisting of two beta polypeptides. Such a complex is typically constitutively active in the sense of having kinase activity. Furthermore, the catalytic sub-unit on its own (ie, the homo-dimer of two alpha polypeptides) has catalytic activity even in the absence of the regulatory sub-unit.

Therefore, either the hetero-tetramer form of CK2 or the homo-dimer form of CK2 may be applied in the present invention, specifically the alpha-beta hetero-tetramer CK2 or alpha-homo dimer CK2.

Most suitably, CK2 is used in the form of a commercial preparation, such as from New England Bio Labs. This is suitably the holo enzyme form of CK2.

Most suitably the CK2 used is composed of two polypeptide chains, each polypeptide chain having the sequence of a human CK2 alpha subunit such as: gene name; CSNK2A1, accession number NM001895.3, NM177559.2, NM177560.2 (3 subtypes) gene name; CSNK2A2, accession number NM001896.2.

With regard to CSNK2A1, NM001895 and NM177559 can produce the same proteins, although they have different 5' non-coding regions. NM177560 encodes isoform b, which has shorter N terminal region. Most suitably protein sequence of NM001895 and NM177559 is used, which is isoform a:

MSGPVPSRARVYTDVNTHRPREYWDYESHVVEWGNQDDYQLVRKLGRGK

YSEVFEAINITNNEKVVVKILKPVKKKKIKREIKILENLRGGPNIITLA

DIVKDPVSRTPALVFEHVNNTDFKQLYQTLTDYDIRFYMYEILKALDYC

HSMGIMHRDVKPHNVMIDHEHRKLRLIDWGLAEFYHPGQEYNVRVASRY

-continued

```
FKGPELLVDYQMYDYSLDMWSLGCMLASMIFRKEPFFHGHDNYDQLVRI

AKVLGTEDLYDYIDKYNIELDPRFNDILGRHSRKRWERFVHSENQHLVS

PEALDFLDKLLRYDHQSRLTAREAMEHPYFYTVVKDQARMGSSSMPGGS

TPVSSANMMSGISSVPTPSPLGPLAGSPVIAAANPLGMPVPAAAGAQQ
```

With regard to CSNK2A2, most suitably the following sequence is used:

```
MPGPAAGSRARVYAEVNSLRSREYWDYEAHVPSWGNQDDYQLVRKLGRG

KYSEVFEAINITNNERVVVKILKPVKKKKIKREVKILENLRGGTNIIKL

IDTVKDPVSKTPALVFEYINNTDFKQLYQILTDFDIRFYMYELLKALDY

CHSKGIMHRDVKPHNVMIDHQQKKLRLIDWGLAEFYHPAQEYNVRVASR

YFKGPELLVDYQMYDYSLDMWSLGCMLASMIFRREPFFHGQDNYDQLVR

IAKVLGTEELYGYLKKYHIDLDPHFNDILGQHSRKRWENFIHSENRHLV

SPEALDLLDKLLRYDHQQRLTAKEAMEHPYFYPVVKEQSQPCADNAVLS

SGLTAAR
```

Protein Kinase A

Suitably, protein kinase A is vertebrate, more suitably mammalian protein kinase A. More suitably, protein kinase A is human protein kinase A.

The protein kinase A used may be composed of 2 alpha subunits and 2 beta subunits. The beta subunit homo-dimer is the inhibitory domain and cAMP is required for dissociation of the beta homo-dimer from alpha homo-dimer.

More suitably the protein kinase A used is composed of 2 alpha polypeptide chains having the sequence of a human PKA alpha subunit (i.e. a PKA alpha subunit homo-dimer): gene name PRKACA, accession number NM002730.3, NM207518.1 (2 subtypes). This has the advantage of avoiding use of the beta subunit (which requires cAMP to activate the PKA alpha-beta hetero-tetramer) and therefore has the further advantage of avoiding use of cAMP. With regard to PRKACA, NM 002730 encodes isoform 1, which is ubiquitously expressed. NM207518 encodes spermatogenic cell-specific PKA, isoform 2. Most suitably the isoform 1 sequence is used such as:

```
MGNAAAAKKGSEQESVKEFLAKAKEDFLKKWESPAQNTAHLDQFERIKT

LGTGSFGRVMLVKHKETGNHYAMKILDKQKVVKLKQIEHTLNEKRILQA

VNFPFLVKLEFSFKDNSNLYMVMEYVPGGEMFSHLRRIGRFSEPHARFY

AAQIVLTFEYLHSLDLIYRDLKPENLLIDQQGYIQVTDFGFAKRVKGRT

WTLCGTPEYLAPEIILSKGYNKAVDWWALGVLIYEMAAGYPPFFADQPI

QIYEKIVSGKVRFPSHFSSDLKDLLRNLLQVDLTKRFGNLKNGVNDIKN

HKWFATTDWIAIYQRKVEAPFIPKFKGPGDTSNFDDYEEEEIRVSINEK

CGKEFSEF
```

High specific activity PKA is available from New England Biolabs.

Suitably alpha-homodimer PKA is used.

Without wishing to be bound by theory, it appears that protein kinase A may not have a physiological role in neurite outgrowth. In other words, it may be that in vivo in a naturally occurring biological system, PKA may not come into contact with a Nogo receptor and/or may not phosphorylate it. However, it is clearly demonstrated herein that PKA does in fact catalyse this key phosphorylation event. For these reasons, it may be that treatment using PKA offers a further advantage in avoiding disturbance of any natural biological processes.

From a comparison of the enzymes which might be used to target serine 281, without wishing to be bound by theory, it appears that CK2 may be a more likely biological candidate for "natural" phosphorylation of the Nogo receptor. For this reason, it may be that using CK2 for the treatments of the invention might offer a further advantage over the use of other possible enzymes such as PKA, since there may be a greater biological fidelity or specificity achieved by use of the most likely natural or biological kinase-substrate pairing. Nevertheless, as demonstrated by the present inventors, CK2 is an effective catalyst for bringing about the phosphorylation of serine 281 of the Nogo receptor.

It should be noted that sub-units of the particular kinases of interest described herein may be equally applied in the present invention. A sub-unit may be a subset of the collection of proteins which typically make up the active enzyme in vivo, or a sub-unit may refer to a fragment or a truncated form of one of the polypeptides of the kinase of interest. In particular, it may be advantageous to use only the catalytic sub-unit of the enzyme of interest. This may provide advantages such as a more active form of the enzyme, and/or may avoid immunogenicity or other such complications which might arise from using larger molecules or complexes. Indeed, use of a polypeptide which happens to be truncated, or mutated, is intended to be within the scope of the invention. Mutations may be made for example to enhance activity or provide independence from known cofactors of the enzyme being used. If a skilled reader wishes to determine whether or not a particular fragment or truncation of an enzyme of interest falls within the scope of the invention, it is essential that the enzyme used retains its functional catalytic activity. More specifically, a kinase used in the present invention is of interest only if it is capable of catalysing incorporation of phosphate into the Nogo receptor, such as at residue 281 of the Nogo receptor. This may be easily tested, for example by combining the kinase or fragment of interest with Nogo receptor in conditions permissive of phosphorylation, and assaying the Nogo receptor thereafter in order to determine if phosphorylation did indeed take place. Moreover, the activity of the kinase of interest may be assessed functionally, for example by applying it to cells and testing its alleviation of the inhibition of neurite outgrowth. Clearly, only those enzymes or fragments capable of producing this functional alleviation of inhibition of neurite outgrowth are of interest or application in the invention. The exemplary ways in which this functional assay may be carried out are presented in the examples section.

Thus, unless the context suggests otherwise, then references to kinases of interest in the invention such as "protein kinase A" or "caesin kinase II" should be taken to include any sub-units, fragments, mutants or truncations of those kinases, always provided that they retain kinase catalytic activity for the Nogo receptor as explained above, most suitably in the functional assay for alleviation of inhibition of neurite outgrowth.

Suitably the protein kinase A or caesin kinase II used in the invention comprises full length polypeptide. More suitably the protein kinase A or caesin kinase II used in the invention comprises polypeptide corresponding to the human wild type enzyme/s. Most suitably the protein kinase A or caesin kinase II used in the invention is as disclosed in the examples section.

Suitably the protein kinase A or caesin kinase II used in the invention comprises E-coli expressed recombinant protein.

Suitably the protein kinase A or caesin kinase II used in the invention is exogenous i.e. is not made in the cells local to the site of administration but is rather supplied externally or exogenously such as in a composition of the invention.

Compositions

Compositions of the invention comprise one or more catalysts such as enzymes capable of bringing about phosphorylation of NogoR serine 281. Suitably such an enzyme is PKA. Suitably such an enzyme is CKII.

Compositions of the invention may comprise PKA and CKII.

CK2 is suitably present at 500-1200 U/ml CK2 final concentration, or an equivalent amount if the composition is dried/lyophilised or concentrated e.g. for storage.

In one embodiment the invention provides a composition comprising 10-100 μM ATP, 5-0.5 μg CK2, 1-10 mM MgCl2 or Mg-acetate and 10-50 mM KCl or K-acetate.

When the enzyme used is CK2 alpha subunit homo-dimer; K ion is optional (in fact K ion is not required); thus suitably compositions containing only CK2 alpha subunit homo-dimer as the enzyme comprise only Mg and ATP as further components.

Using a CK2 alpha and beta hetero-tetramer has the advantage that the beta subunit enhances substrate-specificity of CK2 phoshorylation and K ion promotes this effect of beta subunit. Thus, when using a CK2 alpha and beta hetero-tetramer as the enzyme, suitably K ion is included in order to obtain this advantage.

In one embodiment the invention provides a composition comprising 10-100 μM ATP, 5-0.05 μg PKA and 1-10 mM MgCl2 or Mg-acetate.

Polypeptides of the invention may preferably be combined with various components to produce compositions of the invention. Preferably the compositions are combined with a pharmaceutically acceptable carrier or diluent to produce a pharmaceutical composition (which may be for human or animal use). Suitable carriers and diluents include isotonic saline solutions, for example phosphate-buffered saline.

The composition of the invention may be administered by direct injection.

The composition may be formulated for administration to sites of nervous tissue, such as spinal cord, and may therefore be formulated to be compatible with cerebrospinal fluid or other such tissue.

Typically, each protein may be administered at a particular activity dose rather than a specific mg/kg body weight amount. Exemplary activity levels for administration are given in the examples section. By way of example regarding volumes, for mice, typically we inject around 2 μl in the CNS. Thus, for human, we typically inject 50-200 μl of kinase+ATP solution. Doses of active ingredients are as discussed herein.

Formulation/Administration

Suitably injection is used to deliver a composition of the invention such as CKII and/or PKA.

Compositions of the invention (eg. comprising kinase(s), ATP and/or ion(s)), may be administered topically eg. during spinal decompression surgery.

If surgery is not required, injection may be used as an alternative method for the administration.

After surgery, the compositions of the invention can be administered by periodic injection, over an effective period, such as up to 1 month or longer such as up to 3 months.

Matrix, such as matrigel (BD Bioscience), may advantageously be used to keep the reagent at the administered region. Instead of matrix, any slow release substances and/or devices could be used to control the dosage/release periods.

ATP

Since some neurones can secrete ATP, it may not be an essential element of the composition of the invention. Under in vitro conditions, we have demonstrated the effects of exogenous kinase such as CK2 without addition of ATP, since the culture medium contains ATP.

Suitably compositions of the invention comprise ATP. This has the advantage of supplying ATP to help promote phosphorylation of the Nogo receptor.

Suitably the composition comprises 0.1-1 mM ATP for compositions comprising either CK2 or PKA.

Magnesium

Suitably the composition comprises a source of 5 mM Mg2+ ion.

Mg2+ ion may be supplied as MgCl2, or MgAc (Magnesium acetate) such as (CH3COO)Mg2).

Potassium

When a composition of the invention comprises CK2, suitably said composition further comprises potassium ion. Potassium ion is not typically needed for compositions comprising PKA, but may optionally be included for example when the composition comprising PKA also comprises CKII.

Potassium ion is suitably supplied as 25-50 mM K ion, such as KCl or potassium acetate (CH3COOK).

Potassium ion such as KCl is not essential, but advantageously has promoting effects on kinase activity of alpha-beta hetero-tetramer CK2.

cAMP

Cyclic AMP (cAMP) may optionally be included in compositions of the invention, particularly when said compositions comprise PKA. Specifically, when only the alpha form of PKA is used, cAMP is optional. However, when the beta form of PKA is used, cAMP is desirable to include in the compositions of the invention and has the advantage of enhancing/enabling PKA activity.

cAMP is suitably supplied as di-butylic cAMP or as conventional cAMP. Either compound is available commercially such as via Sigma Inc. or Merck Inc. Use of di-butylic cAMP has the advantage of being cell permeable. Moreover, conventional cAMP does not penetrate plasma membranes. Since the compositions of the invention are suitably applied extracellularly, suitably conventional cAMP is used as cAMP according to the present invention since this offers the advantage of minimising or eliminating any side-effects on intracellular signalling, and offers the advantage of confining the cAMP added to the extracellular environment thereby helping to retain it localised with the enzyme(s) of compositions of the invention.

Advantages

It is an advantage of the invention that phosphorylation of Nogo receptors suppresses Nogo signalling, allowing neurite regeneration.

It is an advantage of the invention that phosphorylation of Nogo receptors blocks binding of their agonists.

The invention finds particular application in spinal cord injury.

It is an advantage of the invention that the Nogo receptor is targeted. This has the advantage of providing methods and compositions which act in a ligand-independent manner.

Combinations

It may be advantageous to combine the invention with inhibition of chondroitin signalling. One way of accomplishing this is that chondroitinase, such as chondroitinase ABC, can be applied to promote conditions permissive of neurite outgrowth. It is an advantage that chondroitinase targets a pathway distinct from the Nogo pathway. Therefore it is advantageous to combine chondroitinase with treatments or compositions of the invention in order to provide a dual targeted approach to promotion of neurite outgrowth.

It may be advantageous to combine the invention with another way of targeting the Nogo pathway. For example, it may be advantageous to combine the invention with the application of an anti-Nogo-receptor antibody, or with antibodies against ligands of the Nogo receptor. It is an advantage of these embodiments that multiple interventions are being used to target the same point in signalling pathway. Therefore, the possibility of unwanted side-effects or crossover signalling into other pathways is advantageously avoided.

It may also be advantageous to combine the invention with an anti-LINGO antibody. An exemplary anti-LINGO antibody may be as supplied by Biogen Inc. Such a combination has the advantage of targeting a different physical molecule, yet still within the same overall signalling complex. Therefore, combinations such as this offer the advantage of signalling fidelity, ie, targeting only a single pathway, combined with the advantage of targeting multiple different molecules, and thereby aiming to achieve a more robust blockade of signal.

It may also be advantageous to combine the invention with rehabilitation, which can be effective to promote proper connection of neurones. Such combination may also advantageously decrease aberrant connection.

The compositions of the invention may find application in administration during or after surgery such as neurosurgery. In this embodiment surgery is an example of injury to adult nervous tissue. Thus, the kinase(s), ATP and any necessary metal ions, may be applied during surgery.

Optionally Cethrin may also be comprised in a composition of the invention. Typically this is used at 0.3, 1, 3, 6 or 9 mg per dose.

Application of matrix, or inclusion of matrix in the composition(s) of the invention, has the advantage of helping the added reagents to remain or persist in the lesion.

Inhibitors of inflammation may be comprised in a composition of the invention, and/or may be applied as soon as possible after the injury/surgery.

Transplantation of stem cells may be carried out, suitably after inflammation has passed (otherwise transplanted cells might be killed by the host immune system). By way of example, for a mouse, cells are transplanted after 5 days from the injury, i.e. transplanting the cells after inflammation.

Thus, inflammation inhibitors, Rho inhibitors (such as C3 toxin) and/or ES cells may usefully be combined with the invention. Concerning ES cells, forced activation of Nogo signalling can inhibit neuronal differentiation but promote glial differentiation of neuronal stem cells. So, if Nogo is active in the injured area, differentiation of transplanted cells may be advantageously promoted by the inhibition of Nogo signalling.

Alleviation of Inhibition of Neurite Outgrowth

It has been a persistent problem in the art that re-growth or regeneration of neurones happens only poorly, or not at all, in damaged adult nervous tissue. In this context, damaged may infer a physical damage by injury, or may infer damage by a neurological disorder such as a degenerative disease. Clearly, in any such setting, regeneration or re-growth of the nervous tissue is desirable.

It is well established that neurite outgrowth is inhibited in healthy adult nervous tissue. It is an aim of the invention to remove or to alleviate this inhibition. The net result of this is a promotion or enhancement of regeneration such as via neurite outgrowth. This might be referred to as stimulation of neurite outgrowth. Indeed, for the majority of applications, there may be no substantial difference between stimulation of neurite outgrowth and alleviation of inhibition of neurite outgrowth. However, due to the insights and understandings gained by the inventors of this cryptic system, the invention is consistently described in terms of alleviation of inhibition of neurite outgrowth. This is because it is established that certain Nogo family ligands are inhibitors of neurite outgrowth. Thus, it is alleviation of this inhibition produced by signalling via the Nogo receptor which is the subject of the invention. If it is helpful to regard removal of this inhibition as "stimulation" of neurite outgrowth, then this may be noted or referred to from time to time. It does not detract from the overall aim of the invention being to remove or ameliorate inhibition of neurite outgrowth, thereby permitting or promoting (or indeed stimulating) neural regeneration such as via neurite outgrowth.

Moreover, the invention may advantageously be combined with one or more stimulator(s) of neurite outgrowth, thereby simultaneously provoking outgrowth as well as removing or alleviating the inhibition, and leading to a more pronounced or enhanced regrowth or regeneration.

Further Applications

In a broad aspect, the invention relates to PKA for use as a medicament.

In a broad aspect, the invention relates to CK2 for use as a medicament.

In a broad aspect, the invention relates to a new extracellular use for CK2.

It is disclosed that protein kinase A (PKA), as well as CK2, can inhibit Nogo signaling. Most suitably the kinase used in the invention is PKA.

The invention relates to alleviation of inhibition of neurite outgrowth after spinal cord injury, in particular by inhibition of Nogo signalling.

Applications of the invention are not only limited to alleviation of inhibition of neurite outgrowth. Nogo signalling is implicated in differentiation (9, 10), synapse formation (11), and migration (12) of neurons during development. It is also implicated in Alzheimer's disease, a neurodegenerative disorder causing dementia (13-15). Thus the invention may advantageously be applied in these areas as well as in especially suitable areas such as alleviation of inhibition of neurite outgrowth.

In particular, the invention may be applied to neurodegenerative disease generally, such as Alzheimer's disease and/or Parkinson's disease. This is a particularly suitable application of the invention since NogoR can bind to amyloid B and to its precursor APP.

The invention may also be applied to more acute neurological disorders such as stroke.

Inhibition of Nogo leads to increased myelination. Therefore the invention finds application in any disorder of myelination, such as multiple sclerosis. Thus the invention may be applied to multiple sclerosis. Schizophrenia is another example of a nervous disorder connected with a defect of myelination. Thus the invention may be applied to schizophrenia. Moreover, the invention relates to a method for increasing myelination in a system, said method comprising phosphorylating a Nogo receptor in said system, suitably by addition of PKA and/or CKII to said system.

The invention also relates to a method of inhibiting binding of inhibitors of neurite outgrowth such as Nogo ligand(s) to the Nogo receptor, said method comprising inducing phosphorylation of said Nogo receptor, such as at serine 281.

SH-SY5Y cells were incubated with indicated reagents. Cell images were taken with phase contrast microscopy. (B) Number of cells extending neurite-like structures of more than 40 µm and total cell number were counted from images taken in (A). More than 300 cells were examined in each sample. The proportion of cells extending neurite-like structures of more than 40 µm was indicated as a percentage of total cell number. An average of three experiments is shown. Error bars indicate S. E. between experiments. Data were analysed with student's t test. (C) Whole cell extracts were prepared from RA-treated SH-SY5Y cells after incubation with or without BDNF for 24 hours, and were analysed by SDS-PAGE. Immunoblotting was performed with the indicated antibodies. (D) Whole cell extract prepared from cells treated with both RA and BDNF was incubated with the indicated reagents for 1 hour at 37° C. Immunoblotting was performed with anti-NgR1 antibody. (E) RA-treated SH-SY5Y cells were incubated with BDNF in the presence or absence of one of the following: PKC inhibitor—500 nM Gö6983 or Gö6976; PKA inhibitor—2 µM KT5720 or a PKA inhibitor peptide 14-22; or either 500 nM or 1 µM of a casein kinase inhibitor, for 24 hours. Whole cell extracts prepared from these cells were analysed by SDS-PAGE. Immunoblotting was performed with anti-NgR1 antibody.

Figure 1:
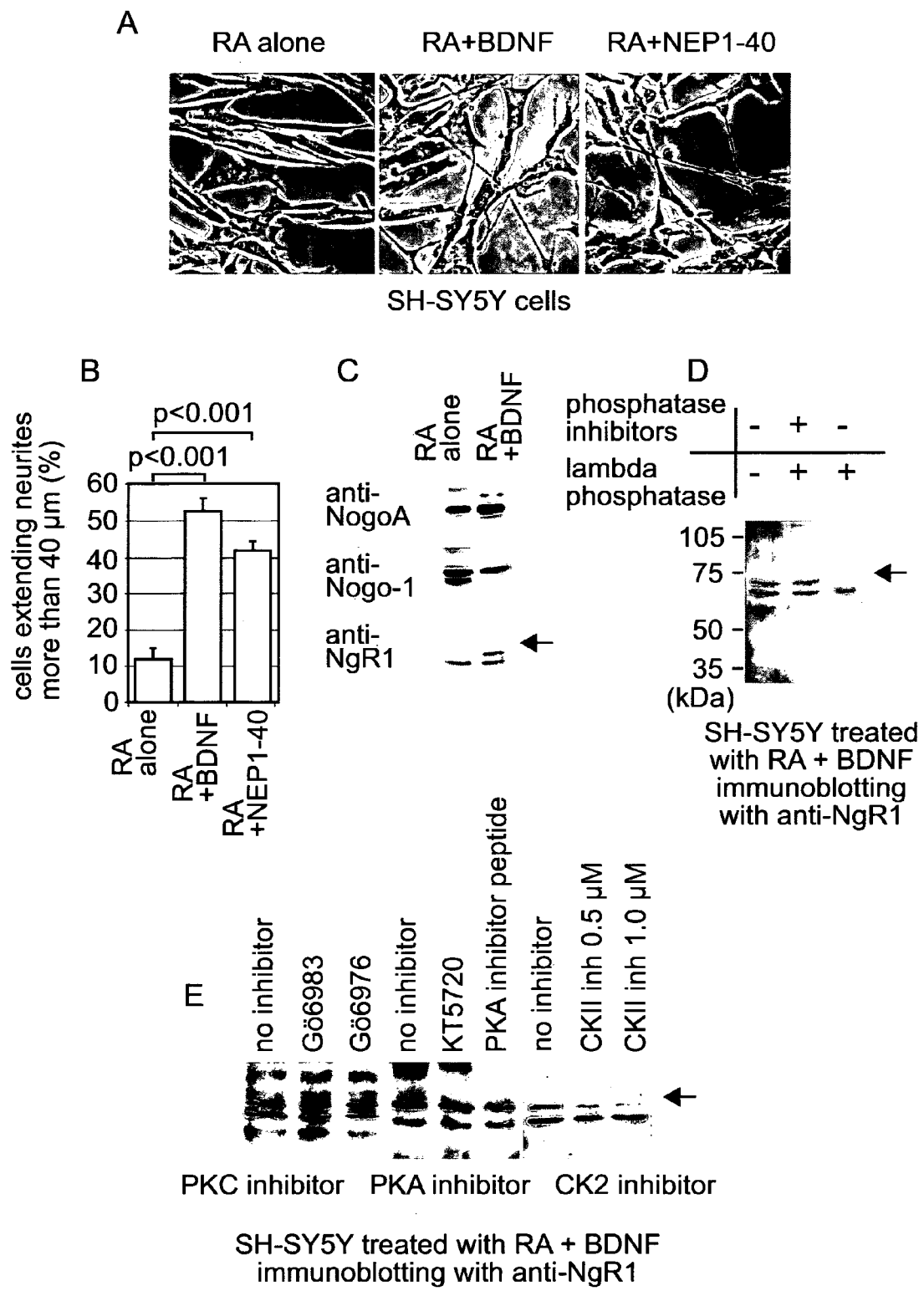
FIG. 1. BDNF promotes neurite outgrowth of RA-treated SH-SY5Y, and induces phosphorylation of NgR1. (A)
Figure 2:
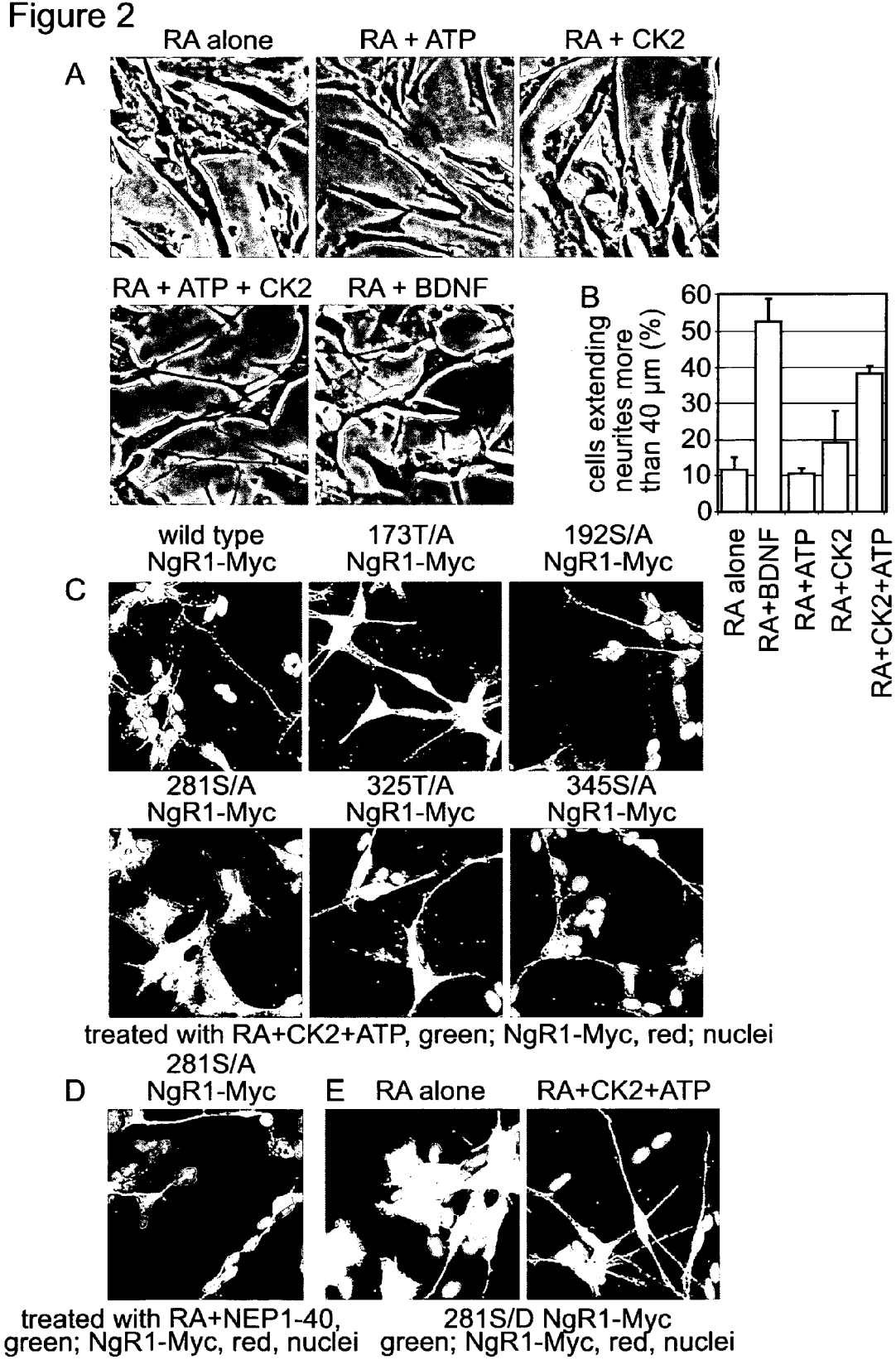

FIG. 2. CK2 promotes neurite outgrowth of RA-treated SH-SY5Y cells without BDNF. (A) RA-treated SH-SY5Y cells were incubated with the indicated reagents for 24 hours. Cell images were taken with phase contrast microscopy. (B) Number of cells extending neurite-like structures of more than 40 µm and total cell number were counted from images taken in (A). More than 300 cells were examined in each sample. Calculation was done as FIG. 1B. Result of student's t test between RA alone and RA+CK II+ATP was p=0.0014. (C) Myc-tagged wild type and mutant versions of NgR1 were over-expressed in SH-SY5Y cells. The cells were treated with RA, CK2 and ATP. Over-expressed NgR1-Myc was detected with anti-Myc antibody. (D) SH-SY5Y cells over-expressing 281S/A mutant NgR1-Myc were incubated with RA and NEP1-40. (E) SH-SY5Y cells over-expressing 281S/D mutant NgR1-Myc were treated as (C).

FIG. 3. CK2 phosphorylates NgR1, and inhibits binding of the myelin-associated proteins to NgR1. (A) Myc-tagged wild type, 281S/A or 281S/D mutant NgR1 were over-expressed in COS7 cells. The over-expressed cells were incubated with either the combination of ATP and CK2, or NEP1-40 for 30 min at 37° C. After washing with PBS, cells were incubated with Hisx6-tagged Nogo-GFP for 3 hours at 4° C. The cells were fixed and immunofluorescence was performed with anti-Myc and anti-GFP antibodies. (B) COS7 cells over-expressing Myc-tagged wild type NgR1 were treated as described in (A). Proteins were extracted and the Myc-tagged NgR1 was immunoprecipitated with anti-Myc antibody. Co-precipitated Hisx6-tagged Nogo-GFP was detected by anti-GFP antibody. (C) Cell surface proteins in NgR1-overexpressing COS7 cells were labelled with biotin. The biotinylated proteins were fractionated and analysed by SDS-PAGE. Biotinylated NgR1-Myc was detected with anti-Myc. antibody. (D) COS7 cells over-expressing either wild type NgR1-Myc or 281S/A mutant NgR1-Myc were incubated with ã-$^{32}$P-ATP in the presence or absence of CK2. Myc-tagged proteins were immunoprecipitated and analysed with SDS-PAGE. Proteins were blotted onto a PVDF membrane and the membrane was exposed to X-ray film to detect incorporated $^{32}$P. After autoradiography, the membrane was used for immunoblotting with anti-Myc antibody. (E and F) COS7 cells over-expressing Myc-tagged wild type, 281S/A or 281S/D mutant NgR1, were treated as described in (A). After washing with PBS, cells were incubated with either His-tagged OMgp (E) or HA-tagged MAG (F) for 3 hours at 4° C. The cells were fixed and immunofluorescence was performed with either anti-Myc and anti-His antibodies (E) or anti-Myc and anti-HA antibodies (F).

FIG. 4. The CK2 target motif containing serine$^{281}$ in human NgR1 is conserved in vertebrate NgR1 and NgR2. (A) Amino acid sequences of C-terminal flanking region in NgR1 of human (GenBank accession number NM 023004), mouse (NM 022982), rat (AF462390), danio (NM 203478) and chicken (XM415292) were compared. Amino acids identical to human NgR1 are indicated in red. (B) Amino acid sequences of C-terminal flanking regions in human NgR1 (GenBank accession number NM 023004), NgR2 (NM 178570) and NgR3 (NM 178568) and mouse NgR1 (NM 022982), NgR2 (NM 199223) and NgR3 (NM 177708) were compared. (C) Whole cell extract was prepared from COS7 cells over-expressing Myc-tagged NgR2 after incubation with ã$^{32}$P-ATP in the presence or absence of CK2. Myc-tagged NgR2 was immunoprecipitated from the whole cell extract and analysed by SDS-PAGE. Proteins were blotted onto a PVDF membrane and the membrane was treated as described in FIG. 3c. (D) COS7 cells over-expressing Myc-tagged human NgR2 were incubated with or without the combination of ATP and CK2 for 30 min at 37° C. After washing with PBS, cells were incubated with HA-tagged MAG for 3 hours at 4° C. The cells were fixed and immunofluorescence was performed with anti-Myc and anti-HA antibodies. (E) After incubation with CK2 and ATP, NgR2-Myc was digested with trypsin in gel and the tryptic peptides were analysed with mass spectrometry. The peptide sequence detected as a phospho-peptide is described.

Figure 5:
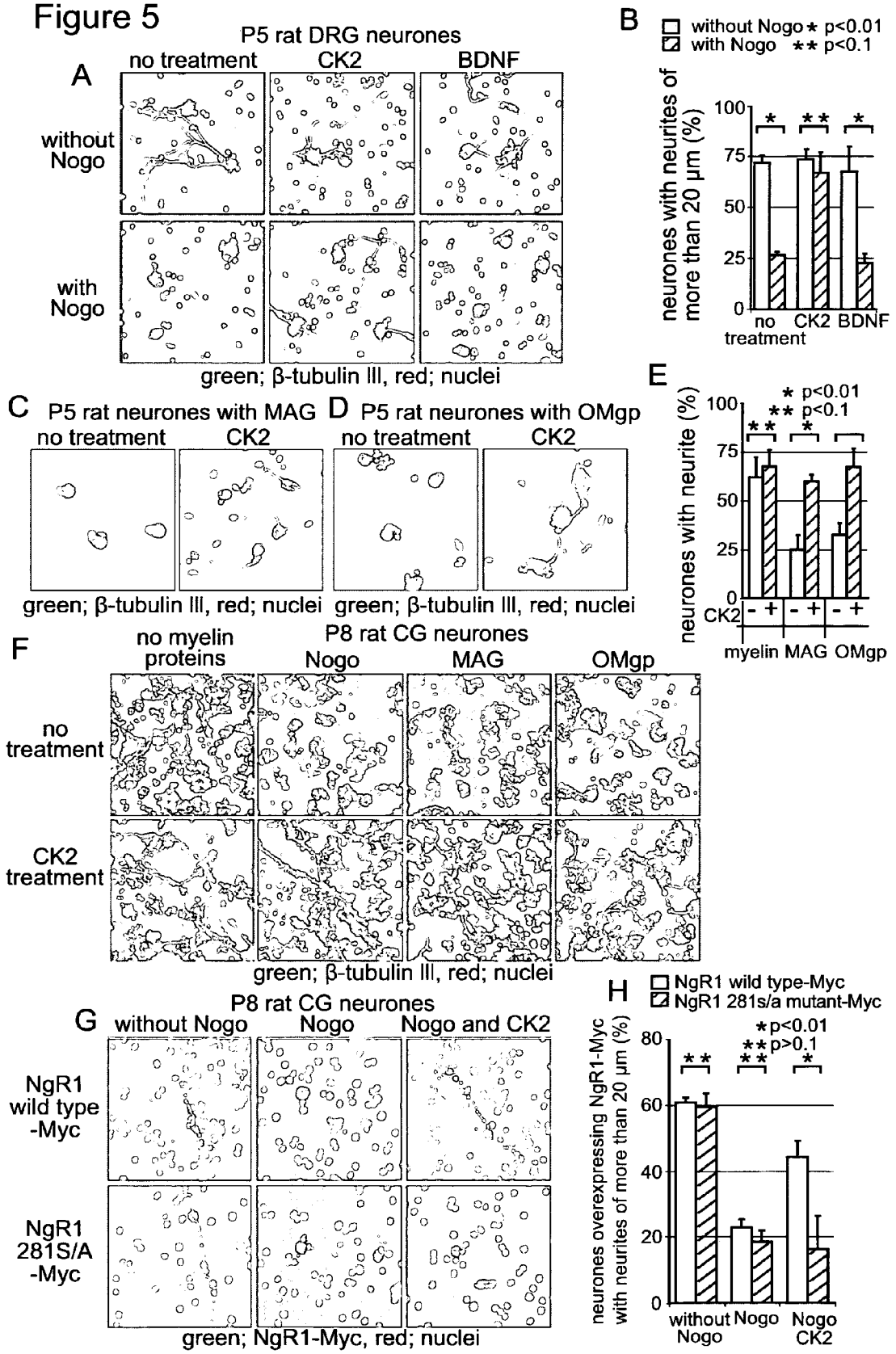

FIG. 5. CK2 rescues postnatal rat neurones from inhibition of neurite outgrowth by the myelin-associated inhibitors, Nogo, MAG and OMgp. (A) DRG neurones from postnatal day 5 rats were cultured with or without the Nogo-66 fragment in the presence of the indicated reagents. After 24 hours from addition of the indicated reagents, cells were fixed and ã-tubulin III was detected by immunofluorescence. (B) The number of cells extending neurites of more than 20 µm and total ã-tubulin III positive cell number were counted from images taken in (A). The population of cells extending neurite-like structures of more than 20 µm was indicated as a percentage of total cell number. An average of three experiments is shown. Error bars indicate S. E. between experiments. Data were analysed with student's t test. (C and D) DRG neurones from postnatal day 5 rats were seeded on an 8 well chamber slide coated with poly-D-Lysine and either MAG (C) or OMgp (D), and incubated with or without CK2 for 24 hours. Cells were fixed and immunofluorescence was performed with anti-ã tubulin III. (E) The number of cells extending neurites of more than 20 µm and total ã-tubulin III positive cell number were counted from images taken in (C and D). The population of cells extending neurite-like structures of more than 20 µm was indicated as a percentage of total cell number. Calculation was done as (B). (F) CG neurones from postnatal day 8 rats were cultured with or without the indicated myelin associated inhibitors for 24 hours in the presence or absence of CK2. Cells were fixed and ã-tubulin III was detected by immunofluorescence. (G) CG neurones over-expressing either wild type NgR1-Myc or 281S/A mutant NgR1-Myc were cultured with or without the Nogo fragment in the presence or absence of CK2 for 24 hours. Over-expressed NgR1-Myc was detected by immunofluorescence. (H) The number of Myc-positive cells extending neurites of more than 20 μm and total Myc-positive cell number were counted from images taken in (G). Calculation was done as (B).

FIG. 6 shows Amino acid sequences of vertebrate NgR1s. NCBI accession numbers of NgR1s are rat; AF 462390, human; NM 023004, mouse; NM 022982, danio; NM 203478, chicken; XM 415292. Red characters show homologous amino acids to human NgR1. Green characters show similar amino acids to human NgR1. NF; N-terminal flanking region, LRR; leucine rich repeat motif, CF; C-terminal flanking region.

Figure 7:
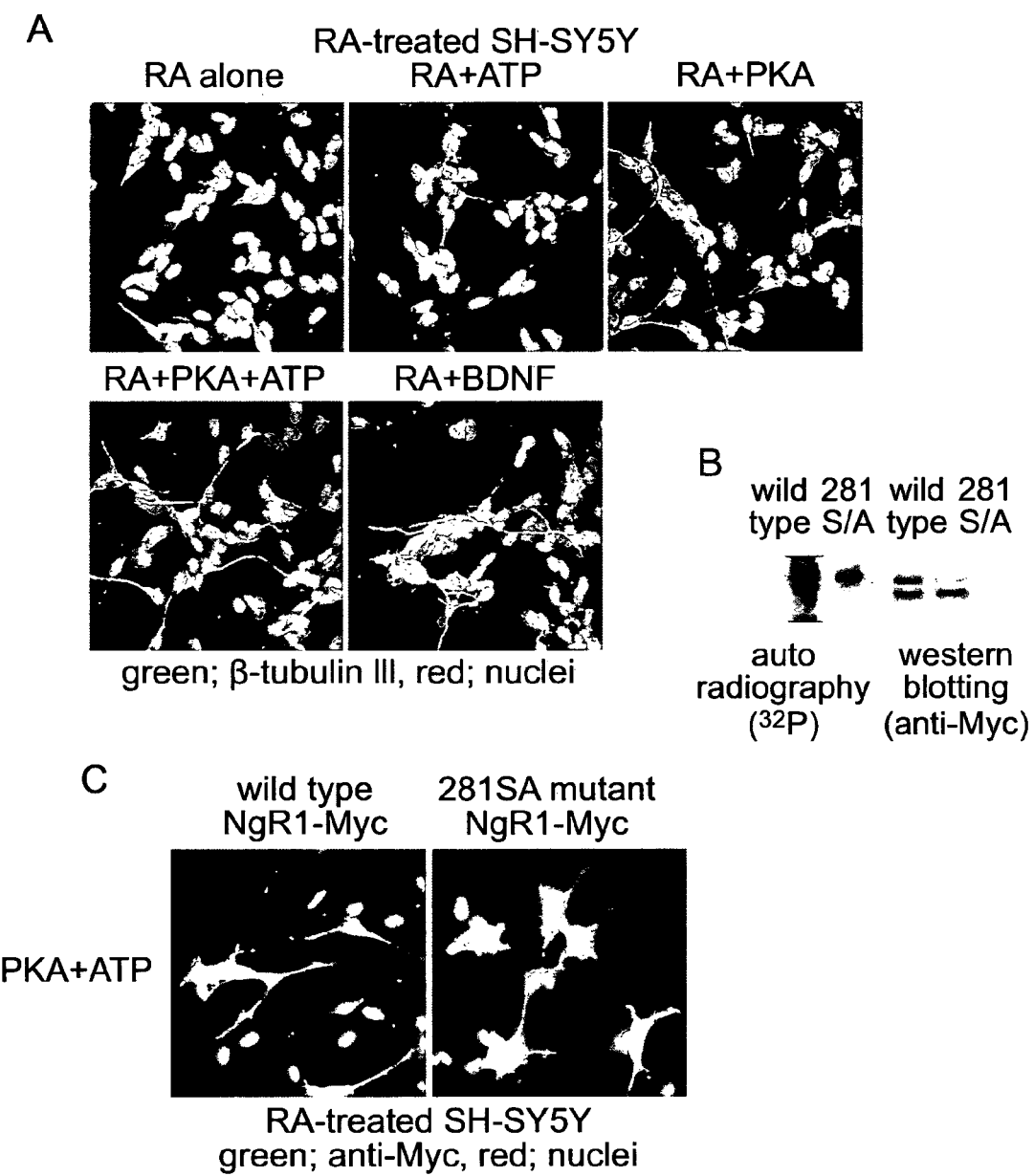

FIG. 7 shows: A, The RA-treated SH-SY5Y cells were cultured with the indicated reagents for 24 hours. After fixation, beta-tubulin III was detected with anti-beta-tubulin III antibody. B, Wild type or 281S/A mutant NgR1-Myc was over-expressed in SH-SY5Y cells. After 5 days treatment with RA, these cells were incubated with 500 U/ml PKA and 500 nM (74 kBq/ml) ATP. Then, NgR1-Myc was immunoprecipitated and analysed with SDS-PAGE. C, RA-treated SH-SY5Y cells over-expressing either wild type or 281S/A mutant NgR1-Myc were incubated with 500 U/ml PKA and 500 nM ATP for 24 hours, and were fixed. NgR1-Myc was detected with anti-Myc antibody. PKA, as well as CK2, induced neurite outgrowth from the RA-treated SH-SY5Y cells (FIG. 7A). PKA phosphorylated wild type NgR1-Myc (FIG. 7B). Mutagenesis at serine281 strongly inhibited both the phosphorylation with PKA (FIG. 7B) and neurite outgrowth after PKA treatment (FIG. 7C). Thus, both PKA and CK2 can phosphorylate NgR1 and can cancel the inhibitory effects of Nogo signalling on neurite outgrowth.

FIG. 8 shows Amino acid sequences of human NgRs. NCBI accession numbers of NgRs are as for FIG. 4B. Red characters show homologous amino acids to human NgR1. The closed triangle shows the position of serine281 in human NgR1.

Figure 9:
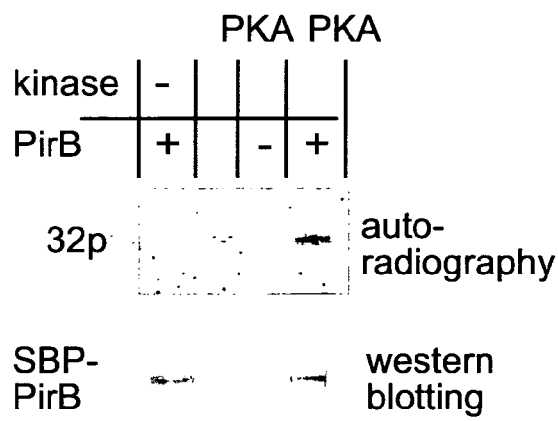

FIG. 9 shows photographs and a sequence alignment. (A) Full length of PirB was expressed in COS7 cells with streptoavidine-binding peptide (SBP) tag at the C terminal. The COS 7 cells were incubated with 2000 U/ml PKA, 5 mM MgSO4 and 100 μM 32P-ATP in OptiMEM (Invitrogen) at 37° C. for 1 hour. After the incubation, the cells were washed and proteins were extracted with 0.5% Triton X-100, 20 mM Tris HCl (pH8.0) and 150 mM NaCl. SBP-tagged PirB was precipitated from the extract with streptoavidin-magnetic beads (Invitrogen). Proteins bound to the beads were analysed by SDS-PAGE, and incorporated 32P was detected by autoradiography. (B) COS7 cells over-expressing PirB were treated as described in (A), except for cold ATP. Proteins analysed by SDS-PAGE was stained with coomassie brilliant blue G-250. The band corresponding to PirB was cut out, and analysed by mass spectrometry. Amino acid sequence of phospho-peptide detected by mass spectrometry was boxed. Closed triangle indicates the phosphorylated amino acid, serine425. Amino acid sequences around the phosphorylation site of human LILRB1, 2, 3 and 5, and rat and mouse PirB were compared. Amino acid residues homologous to mouse PirB was indicated with red characters.

Figure 10B:
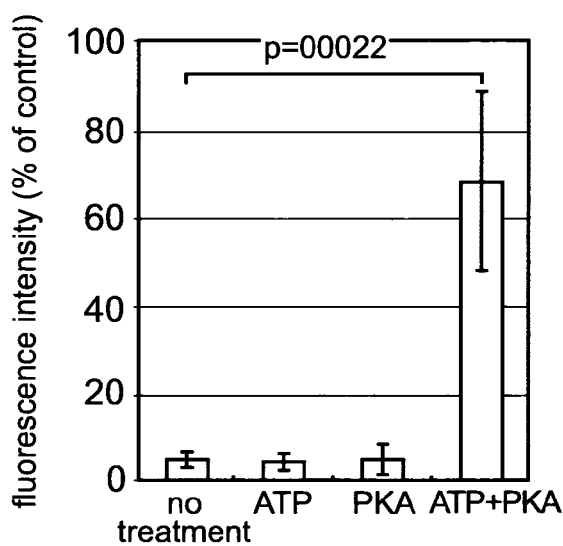
Figure 10A:
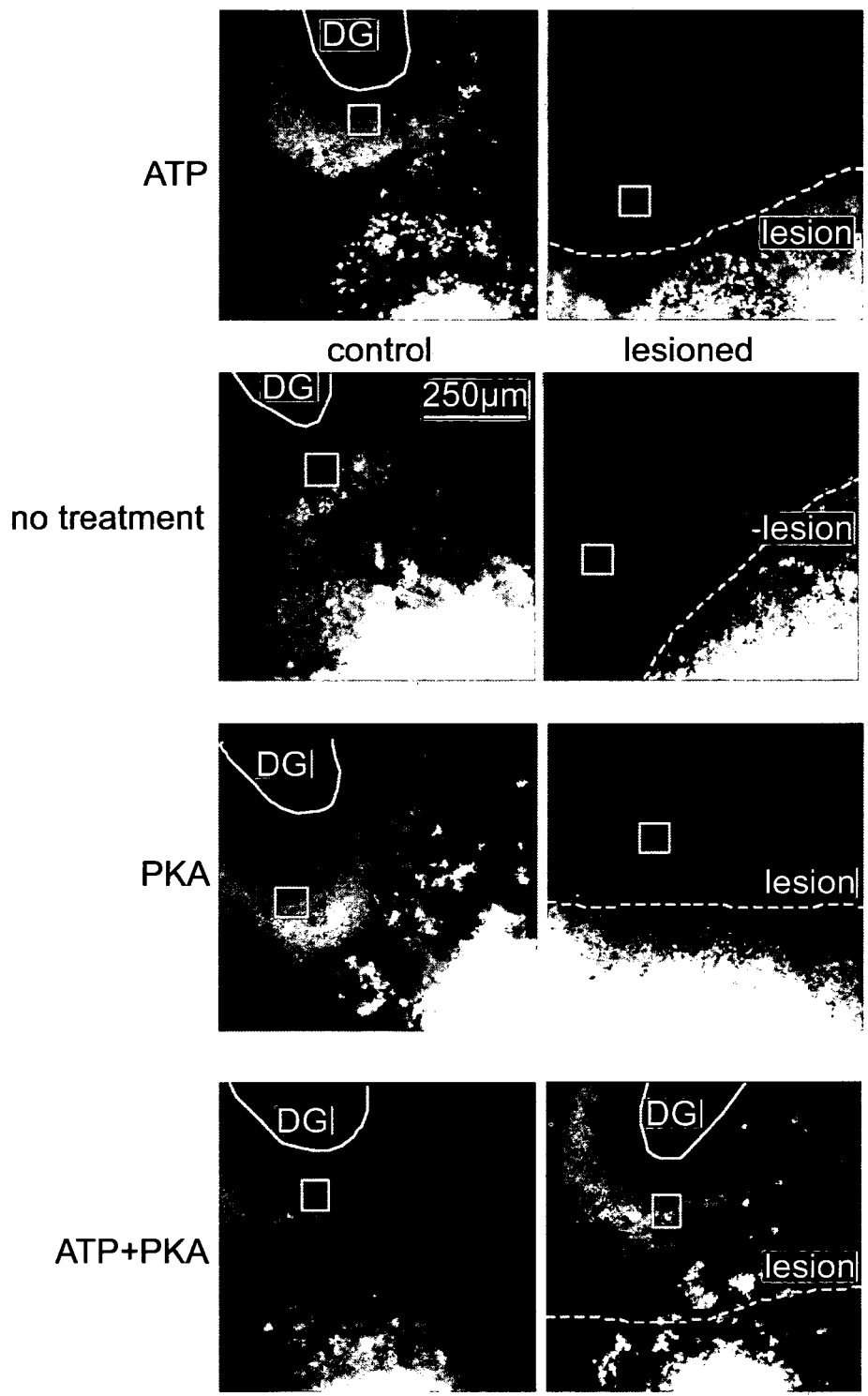

FIG. 10 shows photographs and a bar chart. (A) Organotypic culture of Entorhinal-hippocampal slices was prepared from 129X1/SvJJmsSlc (albino) mice postnatal day 5 and 6. Culture media were changed every 2 days. On the day in vitro (DIV) 10, On the day in vitro (DIV) 10, the entorhinal-hippocampal projection was transected with sterile scalpel brade. The lesioned slices were cultured for 8 days with or without 1250 U/ml PKA and 100 μM ATP. On the DIV17, a small aliquot of DiI paste (Invitrogen) was applied on the entorhinal side of the transection. On the DIV 18, the slices were observed with confocal microscopy to examine regeneration of entorhinal-hippocampal projection. Location of lesion made at DIV 10 is indicated as a white dot line. (B) Intensity of DiI signal near the dentate gyrus was measured with ImageJ (version 1.42q, National institute of health, USA). Measured area (100 μm square) was indicated in (A) as a open white square. Intensity was indicated as a percentage of DiI signal in control (not lesioned). Experiment was repeated for 5 time in triplicate. Typical images are indicated in (A), and average of the 5 independent experiments was plotted in (B). A student t-test was used to assess statistical significance.

The invention is now described by way of example. These examples are intended to be illustrative, and are not intended to limit the appended claims.

EXAMPLES

Methods and Reagents

A human neuroblastoma cell line, SH-SY5Y was purchased from ATCC. Ham's F12 medium, Neurobasal-A medium, mouse anti-GFP monoclonal antibody and B27 supplement were purchased from Invitrogen. Retinoic acid, creatine and creatine phosphokinase, mouse anti-Myc monoclonal antibody and poly-D-Lysine were purchased from Sigma. Rat neurons and NSF-1 supplement were purchased from LONZA. BDNF, Gö6983, Gö6976, the CK2 inhibitor (4,5,6,7-Tetrabromo-2-azabenzimidazole), KT 5720, myristoylated PKA inhibitor peptide 14-22 amide and NEP1-40 peptide were purchased from Merck. Anti-LINGO-1 was purchased from Millipore. Anti-Nogo A and anti-NgR were purchased from Santa Cruz. ATP was purchased from Roche. CK2 and lambda protein phosphatase were purchased from New England Biolab. Collagen IV, OMgp-His and Nogo-Fc was purchased from R&D. Rabbit anti-Myc polyclonal antibody was purchased from Cell Signaling. ã-$^{32}$P-ATP was purchased from GE healthcare.

Cell Culture

SH-SY5Y cells were cultured in Ham's F12 medium with 10% foetal bovine serum at 37° C. in 5% $CO_2$ and 95% air. Passage numbers between 15 and 21 were used in experiments described in this paper. Further passages induce spontaneous differentiation and cells tend to extend neurites without BDNF (data not shown). For RA treatment, the cells are seeded (20,000 cells/well) on collagen IV coated 4 well chamber slides. After 24 hours culture, medium was changed to Ham's F12 medium containing 10 μM RA and 10% foetal bovine serum. Medium was changed to fresh medium on day 3 and cells were used for experiments after 5 days culture. Encinas et al. (18) reported that RA-treated SH-SY5Y cells initiate apoptosis after withdrawal of serum only when the cells are cultured at low density. The cell density used in this paper was higher than that in the paper by Encinas et al. (18) and cell death due to depletion of serum or BDNF was not significant. In this paper, the SH-SY5Y cells treated with RA for 5 days are called RA-treated SH-SY5Y. For BDNF treatment, the RA-treated SH-SY5Y cells were washed with serum-free Ham's F12 medium and incubated with 25 ng/ml BDNF in serum-free Ham's F12 medium for 24 hours. As a control (RA alone), the RA-treated SH-SY5Y cells were incubated with serum-free Ham's F12 alone for 24 hours.

The DRG neurons from postnatal day 5 rats were resuspended in Neurobasal-A media containing 2 mM glutamine and 2% NSF-1 supplement, and seeded (5,000 cells/well) on poly-D-Lysine coated 8 well chamber slides. After 4 hours from seeding, medium was replaced with fresh medium.

The CG neurons from postnatal day 8 rats were resuspended in Neurobasal-A medium containing 25 mM KCl, 2 mM glutamine and 2% B27 supplement, and seeded (10,000 cells/well) on poly-D-Lysine coated 8 well chamber slides. After 4 hours from seeding, medium was replaced with fresh medium.

CK2 Treatment of Cells

For CK2 treatment of RA-treated SH-SY5Y cells, the cells were washed with serum-free Ham's F12 and incubated with either 100 nM ATP or 500 U/ml CK2 or both in serum-free Ham's F12 containing 25 mM KCl and 5 mM MgCl2 for 24 hours.

For CK2 treatment of DRG neurons from postnatal day 5 rats, medium was changed to neurobasal-A medium containing 2 mM glutamine 10 mM KCl, 5 mM $MgCl_2$ and 2% NSF-1 supplement with 500 U/ml CK2, after 4 hours incubation from seeding. As control (no treatment), medium was changed to the medium without CK2. For CG neurons from postnatal day 8 rats, neurobasal-A medium containing 2 mM glutamine, 2% B27 supplement and 25 mM KCl was used.

For CK2 treatment of COS7 cells, cells were washed with serum-free Ham's F12 medium and incubated with or without both 500 μM ATP and 1200 U/ml CK2 in serum-free Ham's F12 medium containing 25 mM KCl and 5 mM $MgCl_2$ for 30 min at 37° C.

Phosphorylation by CK2 with ã $^{32}$P-ATP

For treatment of COS7 cells over-expressing Myc-tagged NgR1 or NgR2, cells were scraped off from the culture dish. The cells were washed with PBS and resuspended in PBS containing 25 mM KCl, 5 mM $MgCl_2$ 1200 U/ml of CK2, 200 μM ATP (3.7 kBq/ml). After incubation for 30 min at 30° C., phosphorylation was terminated and proteins were extracted with 0.1% Triton X 100, 250 mM NaCl and 25 mM EDTA. Myc-tagged proteins were immunoprecipitated with anti-Myc antibody and analysed by SDS-PAGE.

Expression and Purification of Myelin-Associated Proteins

First strand DNA was synthesised from mRNA purified from human foetal brain (TAKARA) with SuperScript II reverse transcriptase (Invitrogen) and oligo dT. The cDNA of human Nogo-A was amplified by PCR with the first strand DNA as template. The amplified Nogo-A (Genbank accession number NM 020532) fragment, Nt 3444-3709, was integrated into pEGFP N2 (TAKARA). The Nogo-A fragment and EGFP region was cut out and integrated into pcDNA 3.1/His vector (Invitrogen). The Hisx6, Nogo-A and EGFP region of the vector was cut out from the vector and integrated into pBEn-SBP-SET vector (Stratagene), then transfected to ArcticExpress (DE3)RIL *E. coli* (Stratagene). Expression of Hisx6-Nogo-A fragment-EGFP protein was induced by 1 mM IPTG overnight at 18° C. Hisx6 Nogo-A fragment-GFP was purified with a TALON column (TAKARA).

For expression of human MAG (NM 002361), cDNA of MAG (Nt 198-1655) was amplified by PCR with the first strand DNA as template and a termination codon was added at the 3' end of the MAG cDNA by PCR. The MAG cDNA was integrated into pDisplay vector (Invitrogen). The plasmid was transfected into COS7 cells. The transfected cells were maintained with DMEM containing 10% serum and 600 μg/ml of geneticin (Invitrogen). For purification of MAG, the cells were cultured with VP-SFM medium (Invitrogen) with 2 mM L-glutamine for 3 days. HA-tagged MAG was purified from the conditioned medium with HA-tag protein purification kit (Sigma).

Expression of NgR1-Myc and NgR2-Myc

NgR2 cDNA was amplified by PCR with the first strand DNA as template. The PCR product was ligated into pCR Blunt vector (Invitrogen). Sequence of the NgR2 cDNA inserted in pCR Blunt was confirmed. IMAGE clone encoding full length NgR1 was purchased from Gene Service Inc. The cDNAs of NgR1 (NM 023004, Nt. 184-1543) and NgR2 (NM 17857, Nt. 1-1200), respectively, were transferred into pDisplay vector with Sal1 and Kpn1 site. The region encoding NgR, Myc tag and transmembrane domain is cut out from the vector with Kpn1 and Not1. The Kpn1-Not1 fragments were integrated into pCEP4 (Invitrogen). Electroporation with Nucleofector (amaxa) was used for transfection. The NgR/pDisplay were transfected into COS7 and NgR1-Myc-transmembrane domain/pCEP4 was transfected into SH-SY5Y cells. For transfection into rat neurons, NeuroMag kit (OZ Bioscience) was used. Neurons cultured for 24 hours on 8 well chamber slides coated with laminin and with or without the Nogo-66 fragment were used for transfection. After the transfection, neurons were cultured for another 24 hours and CK2 was added into culture media to a final concentration of 500 U/ml. Neurons were cultured with CK2 for 24 hours and fixed.

Neurite Outgrowth Assay

For inhibition of neurite outgrowth with myelin-associated inhibitors, 1 μg of Nogo-Fc, 500 ng of HA-tagged MAG or 500 ng of His-tagged OMgp were spotted on different wells of poly-D-Lysine coated 8 well chamber slides, and were left overnight on a clean bench without cover. After washing with PBS twice, neurons were seeded and treated as described in "cell culture". The neurons were cultured for 24 hours at 37° C. and were fixed with 2% paraformaldehyde and 0.1% triton X100 in PBS. Immunofluorescence was performed with anti-ã-tubulin III monoclonal antibody.

Binding Assay of Myelin-Associated Proteins

After treatment with or without CK2, COS7 cells over-expressing wild type or mutant NgR were incubated with Hisx6 tagged Nogo-GFP (10 μg/ml), HA-MAG (50 μg/ml) or Hisx6 tagged OMgp (10 μg/ml) in PBS for 3 hours at 4° C. Cells were washed twice and fixed with 2% paraformaldehyde in PBS for 20 min at 4° C. then with 2% paraformaldehyde and 0.1% Triton X 100 in PBS. To examine the expression levels of NgR1 at the cell surface, a cell surface protein isolation kit (Pierce) was used. Surface proteins of COS 7 cells over-expressing NgR1 were labelled with biotin and were extracted. Biotinylated proteins were precipitated with streptavidin beads and were analysed by SDS-PAGE. Each sample fractionated from $5 \times 10^6$ cells was analysed by SDS-PAGE.

Immunoblotting

Cells were scraped off from dishes and washed with PBS twice, and then resuspended in PBS containing 0.1% Triton X100 and phosphatase inhibitor cocktail (Roche) and EDTA-free protease inhibitor cocktail (Roche). After incubation for 15 min on ice, samples were centrifuged at 14,000×g for 20 min at 4° C. The supernatants containing 30 μg of proteins were analysed by SDS-PAGE and blotted to PVDF membrane. The PVDF membrane was incubated in blocking buffer (5% skimmed milk, 0.4% Triton X-100 in PBS) for 1 hour, first antibody diluted in the blocking buffer and appropriate secondary antibody labelled with horse radish peroxidase. Bound antibodies were visualised with ECL or ECL Plus kit (GE healthcare).

Immunofluorescence Assay

The fixed cells were washed with PBS and incubated with 3% BSA and 0.5% Triton X-100 in PBS at room temperature for 30 min and with first antibody, 3% BSA and 0.5% Triton X-100 in PBS at 37° C. for 2 hours. After washing with PBS, cells were further incubated with appropriate secondary antibody, 3% BSA and 0.5% Triton X-100 in PBS at 37° C. for 30 min. After washing with PBS 3 times, cells were mounted with VECTASHIELD mounting medium with DAPI (VECTOR) and observed with confocal laser scanning microscopy.

Immunoprecipitation

After CK2 treatment (FIG. 3C) or incubation with Nogo-GFP (FIG. 3B), proteins were extracted with 0.1% Triton X100 in PBS containing phosphatase inhibitor cocktail and EDTA-free protease inhibitor cocktail. The extracts were incubated with 25 μg of anti-Myc rabbit polyclonal antibody and protein A magnetic beads (New England Biolab) for 2 hours at 4° C. After washing 5 times with 0.1% Triton X100 in PBS, beads wee incubated with 1×SDS-PAGE loading buffer and heated for 3 min.

Mass Spectrometry

The COS7 cells over-expressing NgR2-Myc were cultured with 500 U/ml of CK2 and 500 μM ATP for 1 hour. Cell extraction and immunoprecipitation of NgR2-Myc with anti-Myc antibody were described above. Precipitated proteins were analysed by SDS-PAGE and the proteins were visualised with colloidal coomassie brilliant blue staining. The band corresponding to NgR2-Myc was cut out from the gel. Proteins in the gel piece were digested in gel with trypsin. Mass spectrometry analysis was done by Cambridge Centre for Proteomics (Cambridge, UK).

Example 1

Nogo Signalling Inhibits Neurite Outgrowth from RA-Treated SH-SY5Y Cells

SH-SY5Y cells showed limited morphological changes after RA treatment for 5 days, but efficient neurite outgrowth was observed after sequential treatment with RA for 5 days and BDNF for 1 day (FIG. 1A), as previously reported by Encinas et al. (18). We found that NEP1-40, a competitive inhibitor of Nogo-66 binding to NgR1 (28), promoted neurite outgrowth from neural cells differentiated from SH-SY5Y cells by RA, without BDNF (FIGS. 1A and B). This suggests that Nogo signalling inhibits neurite outgrowth from the SH-SY5Y-derived neural cells, and that BDNF suppresses the effects of Nogo signalling.

As shown in FIG. 1C, proteins involved in Nogo signalling, Nogo-A, NgR1 and LINGO-1 were expressed in RA-treated SH-SY5Y cells. While neither Nogo-A nor LINGO-1 showed significant changes after BDNF treatment, the upper band of NgR1 was increased by BDNF treatment (FIG. 1C, arrow). Treatment with lambda phosphatase decreased the upper band, only in the absence of phoshatase inhibitors (FIG. 1D). These results indicate that BDNF promotes phosphorylation of endogenous NgR1 in RA-treated SH-SY5Y cells, contributing to the lower mobility on SDS-PAGE. To investigate which kinase is involved in the phosphorylation of NgR1, RA-treated SH-SY5Y cells were incubated with BDNF in the presence of kinase inhibitors. Neither PKC inhibitors Gö6983 and Gö6976, nor PKA inhibitors KT 5720 and a PKA inhibitor peptide, show effects on the level of the upper band of NgR1. However, a CK2 inhibitor decreased the upper band (FIG. 1E). Consistent with this, BDNF is known to activate CK2 in neural cells (29). These results indicate that CK2-like activity is involved in the phosphorylation of NgR1. Thus, BDNF induces phosphorylation of NgR1 by CK2-like activity, which is coincident with promotion of neurite outgrowth by BDNF.

Example 2

RA-Treated SH-SY5Y Cells Extend Neurites after Extra-Cellular Treatment with CK2, without BDNF NGR1 is a glycosylphosphatidylinositol-anchored membrane protein, which does not have a cytoplasmic domain (30, 31). Thus, the phosphorylation sites in NgR1 after BDNF treatment are extra-cellular, and they could be phosphorylated by extra-cellular treatment with CK2. Neither addition of ATP alone nor CK2 alone to the culture medium induced neurite outgrowth from SH-SY5Y-derived neural cells. However, the cells showed significant neurite outgrowth after simultaneous incubation with both CK2 and ATP for 24 hours (FIGS. 2A and B). Thus, extra-cellular treatment with CK2 suppresses inhibitory effects of Nogo signalling on neurite outgrowth from the SH-SY5Y-derived neural cells, without BDNF.

Example 3

Serine$^{281}$ in Human NgR1 is a Key Target for CK2 Mediated Suppression of Nogo Signalling Human NgR1 contains 5 candidate sites for phosphorylation by CK2, threonine$^{173}$, serine$^{192}$, serine$^{281}$, threonine$^{325}$ and serine$^{345}$, and these candidate sites were substituted to alanine. The kinase used in this example is CK2. When the RA-treated SH-SY5Y cells over-expressing these NgR1 mutants were treated with ATP and CK2 for 24 hours, cells carrying the serine$^{281}$ to alanine substitution (281S/A) in NgR1 failed to show significant neurite outgrowth (FIG. 2C). However, the cells carrying the 281S/A mutant NgR1 still had the potential to extend neurites, since they showed neurite outgrowth after treatment with NEP1-40 for 24 hours (FIG. 2D). These results indicate that the 281S/A mutant NgR1 is not constitutively active and binding of Nogo is required for inhibition of neurite outgrowth from RA-treated SH-SY5Y.

Serine$^{281}$ in NgR1 was substituted to aspartic acid (281S/D) and the mutant NgR1 was over-expressed in RA-treated SH-SY5Y cells (FIG. 2E). Although, aspartic acid is negatively charged, like a phosphorylated serine residue, the cells over-expressing 281S/D mutant NgR1 did not extend neurites after RA treatment without co-treatment with CK2 and ATP (FIG. 2E). This indicates that 281S/D mutant NgR1 is not a constitutively negative mutant of NgR1.

These results indicate that serine$^{281}$ in human NgR1 is essential for CK2 to suppress the inhibitory effects of Nogo signalling, even though other membrane proteins can be phosphorylated by extra-cellular treatment with CK2 (32, 33).

Example 4

CK2 Inhibits Binding of the Myelin-Associated Inhibitors to Wild Type Ngr1, but not to the Mutant Ngr1 Carrying a Serine$^{281}$ Substitution The Nogo-66 fragment bound to COS7 cells over-expressing wild type NgR1 (FIG. 3A). However, the Nogo-66 fragment failed to bind to the cells after treatment with CK2 and ATP. When 281S/A mutant NgR1 was over-expressed, instead of wild type NgR1, CK2 treatment failed to block the binding of the Nogo-66 fragment. NEP1-40 inhibited binding of the Nogo-66 fragment to both wild type and the 281S/A mutant NgR1. When 281S/D mutant NgR1 is over-expressed, binding of the Nogo-66 fragment was not observed even without CK2 treatment (FIG. 3A right). Taken together with the results in FIG. 2E, 281S/D mutant NgR1 can neither bind to Nogo-66 nor inhibit signalling through endogenous NgR1. The interaction between the Nogo-66 fragment and over-expressed NgR1 was also observed in immunoprecipitation assays (FIG. 3B). While treatment with either ATP or CK2 alone failed to inhibit the interaction, co-treatment with ATP and CK2 inhibited binding of the Nogo-66 fragment to the over-expressed NgR1. To examine the expression levels of mutant and wild type NgR1-Myc at the cell surface, cell surface proteins were biotinylated. Comparable levels of biotinylated NgR1-Myc, wild type, 281S/A and 281S/D, were detected by western blotting (FIG. 3C).

Furthermore, over-expressed NgR1 is phosphorylated after the extra-cellular treatment with CK2. COS7 cells over-expressing either wild type or 281S/A mutant NgR1 were incubated with CK2 in the presence of ã-$^{32}$P-ATP and over-expressed NgR1s were immunoprecipitated. Although both wild type and 281S/A mutant NgR1 were phosphorylated with CK2 treatment, phosphorylation of the 281S/A mutant NgR1 was much weaker than that of wild type NgR1 (FIG. 3D). These results indicate that serine$^{281}$ of NgR1 is required for both efficient phosphorylation of NgR1 by CK2 and inhibition of interaction between Nogo-66 and NgR1.

FIGS. 3E and F show that CK2 treatment inhibited binding of both OMgp and MAG to wild type NgR1, but not to 281S/A mutant NgR1. Neither OMgp nor MAG bound to COS7 over-expressing 281S/D mutant NgR1. These results indicate that CK2 treatment can inhibit binding of Nogo-66, MAG and OMgp to NgR1 and that serine$^{281}$ in NgR1 is essential for the effect of CK2.

Example 5

Serine$^{281}$ of Human NgR1 is Conserved in Both Vertebrate NgR1 and NgR2

FIG. 4A shows that serine$^{281}$ is in the C-terminal flanking region of the leucine-rich repeats in human NgR1 (30, 31), and that the target motif for CK2 including serine$^{281}$ is conserved in human, mouse, rat, danio and chicken. NgR1 of mouse, rat and chicken has another candidate target motif for CK2 in the C-terminal flanking region, at serine$^{304}$. However, the latter serine is not conserved in human and danio NgR1.

In addition to the CK2 target motif, serine$^{281}$ is involved in the PKA target motif, and the PKA target motif is also conserved in other species (FIG. 4A). This suggests that PKA, as well as CK2, might phosphorylate NgR1, thereby abrogating inhibitory effects of Nogo signalling on neurite outgrowth. However, we could not detect a contribution of PKA to the phosphorylation of NgR1 in RA-treated SH-SY5Y cells after BDNF treatment (FIG. 1E).

Moreover, the CK2 target motif containing the serine$^{281}$ of human NgR1 is conserved in human and mouse NgR2 (FIG. 4B). Serine$^{281}$ in human NgR1 corresponds to serine$^{282}$ in human NgR2. Although NgR3 has a candidate target site for CK2 phosphorylation in the C-terminal flanking region, similar to NgR1 and NgR2, the site is 11 amino acids upstream of the serine$^{281}$ of NgR1. Conversely, the PKA target motif containing serine$^{281}$ in NgR1 is conserved in the three NgRs.

Consistent with the conserved CK2 target motif in NgR2, CK2 phosphorylates NgR2 (FIG. 4C) and CK2 treatment inhibited binding of MAG to COS7 cells over-expressing NgR2 (FIG. 4D). Although human NgR2 contains two CK2 target sites, serine$^{282}$ and threonine$^{366}$, only the CK2 target site containing serine$^{282}$ is conserved in human NgR1. Mass spectrometry detected phosphorylation of the peptide containing serine$^{282}$ of human NgR2, but not the peptide containing threonine$^{366}$, after CK2 treatment (FIG. 4E).

Example 6

CK2 Rescues Rat Neurons from Inhibition of Neurite Outgrowth by Nogo, MAG or OMgp We examined whether phosphorylation of NgRs can rescue rat neurons from inhibition of neurite outgrowth by the myelin-associated inhibitors. When postnatal rat DRG neurons were treated with CK2 for 24 hours, the neurons overcame the inhibition of neurite outgrowth by the Nogo-66 fragment (FIGS. 5A and B). ATP alone did not suppress the inhibitory effects of Nogo-66 fragment (data not shown). Although BDNF can induce neurite outgrowth from RA-treated SH-SY5Y cells (FIGS. 1A and B), BDNF fails to block the effect of the Nogo-66 fragment on DRG neurons (FIGS. 5A and B). This suggests a difference between neuroblastoma cells and normal neurons in BDNF signalling, and it is consistent with the limited effects of BDNF on neurite outgrowth in vivo (21-24, 26).

CK2 treatment can rescue neurons from inhibition of neurite outgrowth not only by the Nogo-66 fragment but also by MAG or OMgp (FIG. 5C-E). FIG. 5F shows that not only DRG neurons from postnatal day 5 rats, but also cerebellar granule (CG) neurons from postnatal day 8 rats can extend neurites in the presence of Nogo-66, MAG or OMgp, when the neurons are treated with CK2 for 24 hours.

Example 7

CK2 Falls to Rescue Neurons Expressing 281S/A Mutant NgR1 from Inhibition of Neurite Outgrowth by Nogo-66

To assess the requirement of the serine$^{281}$ in NgR1, wild type and 281S/A mutant NgR1 were over-expressed in CG neurons from postnatal day 8 rats. Both CG neurons over-expressing wild type and 281S/A mutant NgR1 extended neurites, which was blocked by the Nogo-66 fragment. After CK2 treatment for 24 hours, neurons over-expressing wild type NgR1 extended neurites in the presence of the Nogo-66 fragment. Contrary, neurons over-expressing the 281S/A mutant NgR1 failed to extend neurites even after treatment with CK2 for 24 hours (FIGS. 5G and H). These results indicate that CK2 can inhibit Nogo signalling through wild type NgR1 but not through 281S/A mutant NgR1, which is consistent with FIGS. 2 and 3. Thus, Nogo signalling through NgR1 can block neurite outgrowth from postnatal rat neurons as previously reported (3, 4), and serine$^{281}$ of NgR1 is indispensable for CK2 to suppress the inhibitory effects of Nogo signalling on neurite outgrowth.

Example 8

Method for Alleviating Inhibition of Neurite Outgrowth in a Subject

A method for alleviating the inhibition of neurite outgrowth from a neurone is demonstrated. In this example the subject is a mouse. Mouse neurones comprise a Nogo receptor.

A spinal cord injury model is used. Following induction of the experimental injury, said neurone is contacted with a composition capable of causing phosphorylation of a Nogo receptor. In this step, one of the following two compositions is applied, typically by injection or via a canula introduced at the time of the experimental injury:

A) (PKA):
10-100 µM ATP, 5-0.05 µg PKA and 1-10 mM MgCl2 or Mg-acetate.
or
B) (CKII):
10-100 µM ATP, 5-0.5 µg CK2, 1-10 mM MgCl2 or Mg-acetate and 10-50 mM KCl or K-acetate.

For human applications, higher levels of kinases are used, typically 0.05-5 mg kinase, either PKA or CK2. Concentration of ions and ATP for human use are typically as above.

Example 9

PirB/LILRB

Nogo-A, MAG and OMgp are myelin-associated proteins that can bind to NgR (Gonzenbach, R. R., and Schwab, M. E. (2008). Disinhibition of neurite growth to repair the injured adult CNS: focusing on Nogo. Cell Mol Life Sci 65, 161-176.). Recently, mouse PirB (paired-Ig-like receptor B, NM011095) and its human homologues LILRBs (leukocyte immunoglobulin-like receptor Bs) have been reported to be the second group of receptors for the myelin-associated proteins (Atwal, J. K., Pinkston-Gosse, J., Syken, J., Stawicki, S., Wu, Y., Shatz, C., and Tessier-Lavigne, M. (2008).

PirB is a functional receptor for myelin inhibitors of axonal regeneration. Science 322, 967-970.). Although expression of PirB/LILRB appears to be limited in some specific regions of the brain, it can cooperate with NgRs to inhibit neurite outgrowth (Atwal et al., ibid).

In FIG. 9, PirB was over-expressed in COS7 cells, and the cells were incubated with catalytic subunit of protein kinase A (PKA) and ATP. PirB on the cell surface can be a substrate of PKA (FIG. 9A).

Mass spectrometry indicates that the phosphorylation site is serine$^{425}$ in the extracellular domain of PirB.

The PKA target site is conserved in human, rat and mouse (FIG. 9B). These results suggest that extracellular treatment with PKA could have advantageous effects on signalling from PirB/LILRB, in addition to signalling from NgRs.

Thus in one embodiment the invention relates to a method for alleviating the inhibition of neurite outgrowth from a neurone, wherein said neurone comprises a PirB/LILRB receptor, said method comprising contacting said neurone with a composition capable of causing phosphorylation of PirB/LILRB, wherein said composition comprises protein kinase A or casein kinase II. Suitably said composition comprises protein kinase A and casein kinase II. Suitably said phosphorylation is phosphorylation of an amino acid residue corresponding to serine 425 of said PirB/LILRB.

It may be advantageous to target both Nogo and PirB/LILRB; in this embodiment the invention provides a method for alleviating the inhibition of neurite outgrowth from a neurone, wherein said neurone comprises a Nogo receptor and a PirB/LILRB receptor, said method comprising contacting said neurone with a composition capable of causing phosphorylation of a Nogo receptor and a PirB/LILRB receptor, wherein said composition comprises protein kinase A or casein kinase II. Suitably said composition comprises protein kinase A and casein kinase II. Suitably said phosphorylation is phosphorylation of an amino acid residue corresponding to serine 281 of said Nogo receptor and phosphorylation of an amino acid residue corresponding to serine 425 of said PirB/LILRB.

Example 10

Regeneration of Mammalian CNS According to the Present Invention

In this example we demonstrate the action of the invention on mammalian CNS.

Neurones in the entorhinal cortex form a strong projection to the dentate gyrus of the hippocampus during postnatal period. The entorhinal cortex-hippocampus system is one of the first regions to be affected in Alzheimer's disease, and problems in the system is thought to be result in both impaired sense of direction and disorder of memory.

Organotypic slice culture of the brain preserves many features of the in vivo system, and it is widely used as a model of intact brain.

Entorhinal-hippocampal projection in the intact brain can be conserved in the organotypic slice culture in vitro. Entorhinal-hippocampal slices prepared from mice postnatal day 5-7 show poor regeneration from lesion, after 6 days culture in vitro (Kluge, A., Hailer, N. P., Horvath, T. L., Bechmann, I., and Nitsch, R. (1998). Tracing of the entorhinal-hippocampal pathway in vitro. Hippocampus 8, 57-68. Prang, P., Del Turco, D., and Kapfhammer, J. P. (2001). Regeneration of entorhinal fibers in mouse slice cultures is age dependent and can be stimulated by NT-4, GDNF, and modulators of G-proteins and protein kinase C. Exp Neurol 169, 135-147.).

Chondroitin sulfate proteoglycans and myelin associated proteins are known to be the major inhibitors of the regeneration (Mingorance, A., Sole, M., Muneton, V., Martinez, A., Nieto-Sampedro, M., Soriano, E., and del Rio, J. A. (2006). Regeneration of lesioned entorhino-hippocampal axons in vitro by combined degradation of inhibitory proteoglycans and blockade of Nogo-66/NgR signaling. FASEB J 20, 491-493.).

Migration of microglia, which is resident macrophage in the central nervous system (CNS), can be observed, and glial scar-like structures can be formed by glial cells in the organotypic culture after lesion (Mingorance et al., ibid). All these responses of entorhinal-hippocampal slice culture to lesion is similar to that of normal brain in vivo. Thus the validity of demonstrating the invention in this model system as an illustration of its applicability in mammals generally is well established.

In FIG. 10, entorhinal-hippocampal slices from mice postnatal day 5 or 6 were transected on day in vitro (DIV) 10, and they were incubated with or without PKA and ATP for 8 days.

DiI (1,1'-dioctadecyl-3,3,3'3,-tetramethlindocarbocyanine perchlorate) is a lipophilic membrane stain that diffuses laterally to stain the entire cell, but it cannot move through cell-to-cell interaction. Therefore, projection of neurones can be traced with DiI.

In slices without treatment or slices treated with either PKA or ATP, location of DiI was limited in the entorhinal side of the transection (FIG. 10), indicating that the brain slices can regenerate the neural network, as poor as that in the brain in vivo. Only when the slices were incubated with both ATP and PKA, DiI was observed in the hippocampal side beyond the transection (FIG. 10).

These results indicate that treatment with combination of PKA and ATP can overcome endogenous inhibitors for CNS regeneration, promoting regeneration of the neuronal network according to the present invention.

However, DiI was not detected beyond the dentate gyrus of the hippocampus, even after treatment with PKA and ATP. This indicates that the treatment does not change the intrinsic layer structures in the normal hippocampus (FIG. 10). This is an important feature for promotion of CNS regeneration, to avoid unexpected regeneration that can result in disorders.

Thus, exogenous addition of PKA according to the present invention is demonstrated to be a useful method to promote regeneration of the CNS, which is strictly inhibited under normal conditions.

Summary of Examples Section

We disclose that Nogo signalling can be suppressed by phosphorylation of Nogo receptors. The phosphorylation sites in Nogo receptors are extra-cellular (FIGS. 3 and 4). BDNF induces the ecto-domain phosphorylation of NgR1 in neural cells differentiated from SH-SY5Y cells by RA (FIG. 1). Ecto-domain phosphorylation of NgRs inhibits binding of myelin-associated inhibitors of neurite outgrowth, Nogo-66, MAG and OMgp (FIGS. 3 and 4).

Ecto-domain phosphorylation has been reported in many types of cells, including neurons, immune cells, epithelial cells and endothelial cells (34). Ecto-domain phosphorylation can be catalysed by both ecto-protein kinases after substrate proteins are sorted to the plasma membrane, and intracellular kinases before the sorting (33, 35). While intracellular kinases use intracellular ATP as a source of phosphate group, ecto-protein kinases use extra-cellular ATP. The concentration of extra-cellular ATP under physiological conditions has been estimated at micro-molar level (36). When tissues are damaged, ATP can be released from dying or injured cells through damaged plasma membranes. Inflammation, which can be induced by tissue damage, can also induce release of ATP from a variety of cell types including neurons (37). Thus, the concentration of extra-cellular ATP could be increased by tissue damage. Although in vitro function of ecto-domain phosphorylation has been reported (34), its in vivo function is still unclear.

Recently it was shown that ecto-domain phosphorylation of collagen XVII can inhibit its shedding by metalloproteinases (38). Ecto-domain phosphorylation of collagen XVII is catalysed by CK2, and its phosphorylation site is located in the target site for metalloproteinases (38). While NgRs are also known to be shed by metalloproteinases (39, 40) and they can be phosphorylated by CK2 (FIG. 1-4), the phosphorylation site is not included in the shedding site. The shedding site in NgR1 is amino acid 358 (39), and the phosphorylation site is 281 (FIGS. 3 and 4). We could not detect digested fragments of NgR1 when RA-treated SH-SY5Y cells were analysed by western blotting (FIG. 1). Ecto-domain phosphorylation of NgR1 appears not to regulate its shedding. Instead, we indicate that ecto-domain phosphorylation of NgRs blocks binding of myelin-associated inhibitors of neurite outgrowth, Nogo, MAG and OMgp (FIGS. 3 and 4).

Although BDNF can induce phosphoryaltion of NgR1 and overcome Nogo signalling in RA-treated SH-SY5Y cells (FIG. 1), it fails to attenuate effects of Nogo signalling on neurite outgrowth from rat primary neurons (FIG. 5). Furthermore, although endogenous ecto-CK2 activity has been reported to be associated with neural cells (34), incubation of neural cells with ATP alone failed to inhibit Nogo signalling (FIG. 2). Thus, endogenous ecto-CK2 activity appears to be insufficient to inhibit Nogo signalling. These results suggest that phosphorylation of NgRs could not occur naturally in the CNS, which is consistent with the fact that Nogo signalling can inhibit neurite outgrowth in the CNS (3, 4).

We indicate that extra-cellular treatment with exogenous CK2, instead of BDNF, rescues neurons from inhibition of neurite outgrowth by Nogo signalling (FIG. 5). Extra-cellular treatment with exogenous CK2 phosphorylates serine$^{281}$ in NgR1, which can inhibit binding of Nogo, MAG and OMgp to NgR1 (FIG. 3). The CK2 phosphorylation site in NgR1, serine$^{281}$, is conserved in NgR2, and phosphorylation of NgR2 inhibits binding of MAG (FIG. 4). Although signalling through NgRs is thought to be a main pathway of Nogo signalling, a recent paper indicates that neurons from NgR1$^{-/-}$ mice are still sensitive to inhibition of neurite outgrowth by Nogo signalling (8). This suggests that Nogo signalling could inhibit neurite outgrowth from neurons not only through NgRs but also through unknown Nogo receptors. While depletion of NgR1 fails to rescue neurons from the inhibitory effects of the Nogo-66 fragment (8), extra-cellular treatment with CK2 can (FIG. 5). Therefore, it appears that CK2 treatment must block both NgR-dependent and any independent unknown pathways for inhibition of neurite outgrowth by the myelin-associated inhibitors, Nogo-66, MAG and OMgp. Since the target site for CK2; serine$^{281}$, is also a target site for PKA (FIG. 4), extra-cellular treatment with PKA, as well as CK2, is useful in blocking Nogo signalling.

In summary, we find that BDNF induces phosphorylation of NgR1 in RA-treated SH-SY5Y cells by a CK2-like activity, which overcomes inhibition of neurite outgrowth by Nogo signalling. However, this inhibition of Nogo signalling by BDNF does not occur in rat neurons. Instead of BDNF, extra-cellular treatment with exogenous CK2 rescues neurons from inhibition of neurite outgrowth by Nogo signalling. CK2 phosphorylates ecto-domains of both NgR1 and NgR2, which blocks binding of both MAG to NgR2, and Nogo, MAG and OMgp to NgR1. These results indicate that phosphorylation of Nogo receptors can suppress Nogo signalling. Thus, phosphorylaton of Nogo receptors is demonstrated as a novel target for manipulation of Nogo signalling.

REFERENCES

1. M. E. Schwab, P. Caroni, Oligodendrocytes and CNS myelin are nonpermissive substrates for neurite growth and fibroblast spreading in vitro. *J Neurosci* 8, 2381-2393 (1988).
2. M. E. Schwab, Repairing the injured spinal cord. *Science* 295, 1029-1031 (2002).
3. .
5. T. Oertle, M. E. van der Haar, C. E. Bandtlow, A. Robeva, P. Burfeind, A. Buss, A. B. Huber, M. Simonen, L. Schnell, C. Brosamle, K. Kaupmann, R. Vallon, M. E. Schwab, Nogo-A inhibits neurite outgrowth and cell spreading with three discrete regions. *J Neurosci* 23, 5393-5406 (2003).
6. K. Venkatesh, O. Chivatakarn, H. Lee, P. S. Joshi, D. B. Kantor, B. A. Newman, R. Mage, C. Rader, R. J. Giger, The Nogo-66 receptor homolog NgR2 is a sialic acid-dependent receptor selective for myelin-associated glycoprotein. *J Neurosci* 25, 808-822 (2005).
7. N. R. Mehta, P. H. Lopez, A. A. Vyas, R. L. Schnaar, Gangliosides and Nogo receptors independently mediate myelin-associated glycoprotein inhibition of neurite outgrowth in different nerve cells. *J Biol Chem* 282, 27875-27886 (2007).
8. O. Chivatakarn, S. Kaneko, Z. He, M. Tessier-Lavigne, R. J. Giger, The Nogo-66 receptor NgR1 is required only for the acute growth cone-collapsing but not the chronic growth-inhibitory actions of myelin inhibitors. *J Neurosci* 27, 7117-7124 (2007).
9. B. Wang, Z. Xiao, B. Chen, J. Han, Y. Gao, J. Zhang, W. Zhao, X. Wang, J. Dai, Nogo-66 promotes the differentiation of neural progenitors into astroglial lineage cells through mTOR-STAT3 pathway. *PLoS ONE* 3, e1856 (2008).
10. F. Wang, Y. Zhu, The interaction of Nogo-66 receptor with Nogo-p4 inhibits the neuronal differentiation of neural stem cells. *Neuroscience* 151, 74-81 (2008).
11. E. M. Aloy, O. Weinmann, C. Pot, H. Kasper, D. A. Dodd, T. Rulicke, F. Rossi, M. E. Schwab, Synaptic destabilization by neuronal Nogo-A. *Brain Cell Biol* 35, 137-156 (2006).
12. Z. Su, L. Cao, Y. Zhu, X. Liu, Z. Huang, A. Huang, C. He, Nogo enhances the adhesion of olfactory ensheathing cells and inhibits their migration. *J Cell Sci* 120, 1877-1887 (2007).

13. J. H. Park, D. A. Gimbel, T. GrandPre, J. K. Lee, J. E. Kim, W. Li, D. H. Lee, S. M. Strittmatter, Alzheimer precursor protein interaction with the Nogo-66 receptor reduces amyloid-beta plaque deposition. *J Neurosci* 26, 1386-1395 (2006).
14. V. Gil, O, Nicolas, A. Mingorance, J. M. Urena, B. L. Tang, T. Hirata, J. Saez-Valero, I. Ferrer, E. Soriano, J. A. del Rio, Nogo-A expression in the human hippocampus in normal aging and in Alzheimer disease. *J Neuropathol Exp Neurol* 65, 433-444 (2006).
15. H. Y. Zhu, H. F. Guo, H. L. Hou, Y. J. Liu, S. L. Sheng, J. N. Zhou, Increased expression of the Nogo receptor in the hippocampus and its relation to the neuropathology in Alzheimer's disease. *Hum Pathol* 38, 426-434 (2007).
16. S. S. Hannila, M. T. Filbin, The role of cyclic AMP signaling in promoting axonal regeneration after spinal cord injury. *Exp Neurol* 209, 321-332 (2008).
17. R. H. Fryer, D. R. Kaplan, L. F. Kromer, Truncated trkB receptors on nonneuronal cells inhibit BDNF-induced neurite outgrowth in vitro. *Exp Neurol* 148, 616-627 (1997).
18. M. Encinas, M. Iglesias, Y. Liu, H. Wang, A. Muhaisen, V. Cena, C. Gallego, J. X. Comella, Sequential treatment of SH-SY5Y cells with retinoic acid and brain-derived neurotrophic factor gives rise to fully differentiated, neurotrophic factor-dependent, human neuron-like cells. *J Neurochem* 75, 991-1003 (2000).
19. R. Salie, J. D. Steeves, IGF-1 and BDNF promote chick bulbospinal neurite outgrowth in vitro. *Int J Dev Neurosci* 23, 587-598 (2005).
20. E. Pastrana, M. T. Moreno-Flores, J. Avila, F. Wandosell, L. Minichiello, J. Diaz-Nido, BDNF production by olfactory ensheathing cells contributes to axonal regeneration of cultured adult CNS neurons. *Neurochem Int* 50, 491-498 (2007).
21. B. S. Bregman, M. McAtee, H. N. Dai, P. L. Kuhn, Neurotrophic factors increase axonal growth after spinal cord injury and transplantation in the adult rat. *Exp Neurol* 148, 475-494 (1997).
22. L. B. Jakeman, P. Wei, Z. Guan, B. T. Stokes, Brain-derived neurotrophic factor stimulates hindlimb stepping and sprouting of cholinergic fibers after spinal cord injury. *Exp Neurol* 154, 170-184 (1998).
23. Y. Jin, I. Fischer, A. Tessler, J. D. Houle, Transplants of fibroblasts genetically modified to express BDNF promote axonal regeneration from supraspinal neurons following chronic spinal cord injury. *Exp Neurol* 177, 265-275 (2002).
24. P. Lu, A. Blesch, M. H. Tuszynski, Neurotrophism without neurotropism: BDNF promotes survival but not growth of lesioned corticospinal neurons. *J Comp Neurol* 436, 456-470 (2001).
25. D. Cai, Y. Shen, M. De Bellard, S. Tang, M. T. Filbin, Prior exposure to neurotrophins blocks inhibition of axonal regeneration by MAG and myelin via a cAMP-dependent mechanism. *Neuron* 22, 89-101 (1999).
26. C. Dinocourt, S. E. Gallagher, S. M. Thompson, Injury-induced axonal sprouting in the hippocampus is initiated by activation of trkB receptors. *Eur J Neurosci* 24, 1857-1866 (2006).
27. S. Pahlman, A. I. Ruusala, L. Abrahamsson, M. E. Mattsson, T. Esscher, Retinoic acid-induced differentiation of cultured human neuroblastoma cells: a comparison with phorbolester-induced differentiation. *Cell Differ* 14, 135-144 (1984).
28. T. GrandPre, S. Li, S. M. Strittmatter, Nogo-66 receptor antagonist peptide promotes axonal regeneration. *Nature* 417, 547-551 (2002).
29. P. R. Blanquet, Neurotrophin-induced activation of casein kinase 2 in rat hippocampal slices. *Neuroscience* 86, 739-749 (1998).
30. W. A. Barton, B. P. Liu, D. Tzvetkova, P. D. Jeffrey, A. E. Fournier, D. Sah, R. Cate, S. M. Strittmatter, D. B. Nikolov, Structure and axon outgrowth inhibitor binding of the Nogo-66 receptor and related proteins. *Embo J* 22, 3291-3302 (2003).
31. X. L. He, J. F. Bazan, G. McDermott, J. B. Park, K. Wang, M. Tessier-Lavigne, Z. He, K. C. Garcia, Structure of the Nogo receptor ectodomain: a recognition module implicated in myelin inhibition. *Neuron* 38, 177-185 (2003).
32. J. Walter, A. Schindzielorz, B. Hartung, C. Haass, Phosphorylation of the beta-amyloid precursor protein at the cell surface by ectocasein kinases 1 and 2. *J Biol Chem* 275, 23523-23529 (2000).
33. S. Yamauchi, Y. Tokita, S. Aono, F. Matsui, T. Shuo, H. Ito, K. Kato, K. Kasahara, A. Oohira, Phosphorylation of neuroglycan C, a brain-specific transmembrane chondroitin sulfate proteoglycan, and its localization in the lipid rafts. *J Biol Chem* 277, 20583-20590 (2002).
34. F. A. Redegeld, C. C. Caldwell, M. V. Sitkovsky, Ecto-protein kinases: ecto-domain phosphorylation as a novel target for pharmacological manipulation? *Trends Pharmacol Sci* 20, 453-459 (1999).
35. J. Walter, A. Capell, A. Y. Hung, H. Langen, M. Schnolzer, G. Thinakaran, S. S. Sisodia, D. J. Selkoe, C. Haass, Ectodomain phosphorylation of beta-amyloid precursor protein at two distinct cellular locations. *J Biol Chem* 272, 1896-1903 (1997).
36. E. M. Schwiebert, Extracellular ATP-mediated propagation of Ca(2+) waves. Focus on "mechanical strain-induced Ca(2+) waves are propagated via ATP release and purinergic receptor activation". *Am J Physiol Cell Physiol* 279, C281-3 (2000).
37. J. Sawynok, X. J. Liu, Adenosine in the spinal cord and periphery: release and regulation of pain. *Prog Neurobiol* 69, 313-340 (2003).
38. E. P. Zimina, A. Fritsch, B. Schermer, A. Y. Bakulina, M. Bashkurov, T. Benzing, L. Bruckner-Tuderman, Extracellular phosphorylation of collagen XVII by ecto-casein kinase 2 inhibits ectodomain shedding. *J Biol Chem* 282, 22737-22746 (2007).
39. A. R. Walmsley, G. McCombie, U. Neumann, D. Marcellin, R. Hillenbrand, A. K. Mir, S. Frentzel, Zinc metalloproteinase-mediated cleavage of the human Nogo-66 receptor. *J Cell Sci* 117, 4591-4602 (2004).
40. A. R. Walmsley, A. K. Mir, S. Frentzel, Ectodomain shedding of human Nogo-66 receptor homologue-1 by zinc metalloproteinases. *Biochem Biophys Res Common* 327, 112-116 (2005).

All publications mentioned in the above specification are herein incorporated by reference. Various modifications and variations of the described aspects and embodiments of the present invention will be apparent to those skilled in the art without departing from the scope of the present invention. Although the present invention has been described in connection with specific preferred embodiments, it should be understood that the invention as claimed should not be unduly limited to such specific embodiments. Indeed, various modifications of the described modes for carrying out the invention which are apparent to those skilled in the art are intended to be within the scope of the following claims.

The invention claimed is:

1. A method for alleviating the inhibition of neurite outgrowth from a neurone, wherein said neurone comprises a Nogo receptor localized to its membrane, said method comprising the step of exogenously applying locally to said neurone membrane a composition capable of causing phosphorylation of said membrane-localized Nogo receptor, wherein said composition comprises protein kinase A or casein kinase II.

2. The method according to claim 1 wherein said composition comprises protein kinase A and casein kinase II.

3. The method according to claim 1 wherein said phosphorylation is phosphorylation of an amino acid residue corresponding to serine 281 of said Nogo receptor.

4. The method according to claim 1 wherein said Nogo receptor is human NgR1.

5. The method according to claim 2 wherein said phosphorylation is phosphorylation of an amino acid residue corresponding to serine 281 of said Nogo receptor.

6. The method according to claim 2 wherein said Nogo receptor is human NgR1.

7. The method according to claim 3 wherein said Nogo receptor is human NgR1.

8. The method according to claim 1 wherein said Nogo receptor is human NgR1.

9. A method for alleviating the inhibition of neurite outgrowth from a neurone, wherein said neurone comprises a Nogo receptor localized to its membrane, said method comprising the step of exogenously administering locally to said neurone membrane a composition capable of causing phosphorylation of said membrane-localized Nogo receptor, wherein said composition comprises protein kinase A or casein kinase II.

10. The method according to claim 9, wherein said composition is administered by direct injection.

11. The method according to claim 9, wherein said administration is localized to a site of nervous tissue injury.

12. The method according to claim 9, wherein said administration is localized to a nervous tissue surgical site.

13. The method according to claim 12, wherein said administration step is performed during or after neurosurgery.

* * * * *

SEQUENCE LISTING

<160> NUMBER OF SEQ ID NOS: 26

<210> SEQ ID NO 1
<211> LENGTH: 473
<212> TYPE: PRT
<213> ORGANISM: Homo sapiens

<400> SEQUENCE: 1

```
Met Lys Arg Ala Ser Ala Gly Gly Ser Arg Leu Leu Ala Trp Val Leu
 1               5                  10                  15

Trp Leu Gln Ala Trp Gln Val Ala Ala Pro Cys Pro Gly Ala Cys Val
            20                  25                  30

Cys Tyr Asn Glu Pro Lys Val Thr Thr Ser Cys Pro Gln Gln Gly Leu
        35                  40                  45

Gln Ala Val Pro Val Gly Ile Pro Ala Ala Ser Gln Arg Ile Phe Leu
    50                  55                  60

His Gly Asn Arg Ile Ser His Val Pro Ala Ala Ser Phe Arg Ala Cys
65                  70                  75                  80

Arg Asn Leu Thr Ile Leu Trp Leu His Ser Asn Val Leu Ala Arg Ile
                85                  90                  95

Asp Ala Ala Ala Phe Thr Gly Leu Ala Leu Leu Glu Gln Leu Asp Leu
            100                 105                 110

Ser Asp Asn Ala Gln Leu Arg Ser Val Asp Pro Ala Thr Phe His Gly
        115                 120                 125

Leu Gly Arg Leu His Thr Leu His Leu Asp Arg Cys Gly Leu Gln Glu
    130                 135                 140

Leu Gly Pro Gly Leu Phe Arg Gly Leu Ala Ala Leu Gln Tyr Leu Tyr
145                 150                 155                 160

Leu Gln Asp Asn Ala Leu Gln Ala Leu Pro Asp Asp Thr Phe Arg Asp
                165                 170                 175

Leu Gly Asn Leu Thr His Leu Phe Leu His Gly Asn Arg Ile Ser Ser
            180                 185                 190

Val Pro Glu Arg Ala Phe Arg Gly Leu His Ser Leu Asp Arg Leu Leu
        195                 200                 205

Leu His Gln Asn Arg Val Ala His Val His Pro His Ala Phe Arg Asp
    210                 215                 220

Leu Gly Arg Leu Met Thr Leu Tyr Leu Phe Ala Asn Asn Leu Ser Ala
225                 230                 235                 240

Leu Pro Thr Glu Ala Leu Ala Pro Leu Arg Ala Leu Gln Tyr Leu Arg
                245                 250                 255

Leu Asn Asp Asn Pro Trp Val Cys Asp Cys Arg Ala Arg Pro Leu Trp
            260                 265                 270

Ala Trp Leu Gln Lys Phe Arg Gly Ser Ser Ser Glu Val Pro Cys Ser
        275                 280                 285

Leu Pro Gln Arg Leu Ala Gly Arg Asp Leu Lys Arg Leu Ala Ala Asn
    290                 295                 300

Asp Leu Gln Gly Cys Ala Val Ala Thr Gly Pro Tyr His Pro Ile Trp
305                 310                 315                 320

Thr Gly Arg Ala Thr Asp Glu Glu Pro Leu Gly Leu Pro Lys Cys Cys
                325                 330                 335

Gln Pro Asp Ala Ala Asp Lys Ala Ser Val Leu Glu Pro Gly Arg Pro
            340                 345                 350

Ala Ser Ala Gly Asn Ala Leu Lys Gly Arg Val Pro Pro Gly Asp Ser
        355                 360                 365
```

```
Pro Pro Gly Asn Gly Ser Gly Pro Arg His Ile Asn Asp Ser Pro Phe
    370             375                 380

Gly Thr Leu Pro Gly Ser Ala Glu Pro Leu Thr Ala Val Arg Pro
385             390                 395                 400

Glu Gly Ser Glu Pro Pro Gly Phe Pro Thr Ser Gly Pro Arg Arg Arg
                405                 410                 415

Pro Gly Cys Ser Arg Lys Asn Arg Thr Arg Ser His Cys Arg Leu Gly
            420                 425                 430

Gln Ala Gly Ser Gly Gly Gly Thr Gly Asp Ser Glu Gly Ser Gly
            435                 440                 445

Ala Leu Pro Ser Leu Thr Cys Ser Leu Thr Pro Leu Gly Leu Ala Leu
450                 455                 460

Val Leu Trp Thr Val Leu Gly Pro Cys
465             470

<210> SEQ ID NO 2
<211> LENGTH: 391
<212> TYPE: PRT
<213> ORGANISM: Homo sapiens

<400> SEQUENCE: 2

Met Ser Gly Pro Val Pro Ser Arg Ala Arg Val Tyr Thr Asp Val Asn
1               5                   10                  15

Thr His Arg Pro Arg Glu Tyr Trp Asp Tyr Glu Ser His Val Val Glu
                20                  25                  30

Trp Gly Asn Gln Asp Asp Tyr Gln Leu Val Arg Lys Leu Gly Arg Gly
            35                  40                  45

Lys Tyr Ser Glu Val Phe Glu Ala Ile Asn Ile Thr Asn Asn Glu Lys
50                  55                  60

Val Val Val Lys Ile Leu Lys Pro Val Lys Lys Lys Ile Lys Arg
65                  70                  75                  80

Glu Ile Lys Ile Leu Glu Asn Leu Arg Gly Gly Pro Asn Ile Ile Thr
                85                  90                  95

Leu Ala Asp Ile Val Lys Asp Pro Val Ser Arg Thr Pro Ala Leu Val
                100                 105                 110

Phe Glu His Val Asn Asn Thr Asp Phe Lys Gln Leu Tyr Gln Thr Leu
            115                 120                 125

Thr Asp Tyr Asp Ile Arg Phe Tyr Met Tyr Glu Ile Leu Lys Ala Leu
            130                 135                 140

Asp Tyr Cys His Ser Met Gly Ile Met His Arg Asp Val Lys Pro His
145                 150                 155                 160

Asn Val Met Ile Asp His Glu His Arg Lys Leu Arg Leu Ile Asp Trp
                165                 170                 175

Gly Leu Ala Glu Phe Tyr His Pro Gly Gln Glu Tyr Asn Val Arg Val
            180                 185                 190

Ala Ser Arg Tyr Phe Lys Gly Pro Glu Leu Leu Val Asp Tyr Gln Met
            195                 200                 205

Tyr Asp Tyr Ser Leu Asp Met Trp Ser Leu Gly Cys Met Leu Ala Ser
            210                 215                 220

Met Ile Phe Arg Lys Glu Pro Phe Phe His Gly His Asp Asn Tyr Asp
225                 230                 235                 240

Gln Leu Val Arg Ile Ala Lys Val Leu Gly Thr Glu Asp Leu Tyr Asp
                245                 250                 255

Tyr Ile Asp Lys Tyr Asn Ile Glu Leu Asp Pro Arg Phe Asn Asp Ile
            260                 265                 270
```

```
Leu Gly Arg His Ser Arg Lys Arg Trp Glu Arg Phe Val His Ser Glu
            275                 280                 285

Asn Gln His Leu Val Ser Pro Glu Ala Leu Asp Phe Leu Asp Lys Leu
        290                 295                 300

Leu Arg Tyr Asp His Gln Ser Arg Leu Thr Ala Arg Glu Ala Met Glu
305                 310                 315                 320

His Pro Tyr Phe Tyr Thr Val Val Lys Asp Gln Ala Arg Met Gly Ser
                325                 330                 335

Ser Ser Met Pro Gly Gly Ser Thr Pro Val Ser Ser Ala Asn Met Met
            340                 345                 350

Ser Gly Ile Ser Ser Val Pro Thr Pro Ser Pro Leu Gly Pro Leu Ala
        355                 360                 365

Gly Ser Pro Val Ile Ala Ala Ala Asn Pro Leu Gly Met Pro Val Pro
370                 375                 380

Ala Ala Ala Gly Ala Gln Gln
385                 390

<210> SEQ ID NO 3
<211> LENGTH: 350
<212> TYPE: PRT
<213> ORGANISM: Homo sapiens

<400> SEQUENCE: 3

Met Pro Gly Pro Ala Ala Gly Ser Arg Ala Arg Val Tyr Ala Glu Val
1               5                   10                  15

Asn Ser Leu Arg Ser Arg Glu Tyr Trp Asp Tyr Glu Ala His Val Pro
            20                  25                  30

Ser Trp Gly Asn Gln Asp Asp Tyr Gln Leu Val Arg Lys Leu Gly Arg
        35                  40                  45

Gly Lys Tyr Ser Glu Val Phe Glu Ala Ile Asn Ile Thr Asn Asn Glu
    50                  55                  60

Arg Val Val Val Lys Ile Leu Lys Pro Val Lys Lys Lys Lys Ile Lys
65                  70                  75                  80

Arg Glu Val Lys Ile Leu Glu Asn Leu Arg Gly Gly Thr Asn Ile Ile
                85                  90                  95

Lys Leu Ile Asp Thr Val Lys Asp Pro Val Ser Lys Thr Pro Ala Leu
            100                 105                 110

Val Phe Glu Tyr Ile Asn Asn Thr Asp Phe Lys Gln Leu Tyr Gln Ile
        115                 120                 125

Leu Thr Asp Phe Asp Ile Arg Phe Tyr Met Tyr Glu Leu Leu Lys Ala
    130                 135                 140

Leu Asp Tyr Cys His Ser Lys Gly Ile Met His Arg Asp Val Lys Pro
145                 150                 155                 160

His Asn Val Met Ile Asp His Gln Gln Lys Lys Leu Arg Leu Ile Asp
                165                 170                 175

Trp Gly Leu Ala Glu Phe Tyr His Pro Ala Gln Glu Tyr Asn Val Arg
            180                 185                 190

Val Ala Ser Arg Tyr Phe Lys Gly Pro Glu Leu Leu Val Asp Tyr Gln
        195                 200                 205

Met Tyr Asp Tyr Ser Leu Asp Met Trp Ser Leu Gly Cys Met Leu Ala
    210                 215                 220

Ser Met Ile Phe Arg Arg Glu Pro Phe Phe His Gly Gln Asp Asn Tyr
225                 230                 235                 240

Asp Gln Leu Val Arg Ile Ala Lys Val Leu Gly Thr Glu Glu Leu Tyr
```

-continued

```
                 245                 250                 255
Gly Tyr Leu Lys Lys Tyr His Ile Asp Leu Asp Pro His Phe Asn Asp
             260                 265                 270
Ile Leu Gly Gln His Ser Arg Lys Arg Trp Glu Asn Phe Ile His Ser
         275                 280                 285
Glu Asn Arg His Leu Val Ser Pro Glu Ala Leu Asp Leu Leu Asp Lys
     290                 295                 300
Leu Leu Arg Tyr Asp His Gln Gln Arg Leu Thr Ala Lys Glu Ala Met
305                 310                 315                 320
Glu His Pro Tyr Phe Tyr Pro Val Val Lys Glu Gln Ser Gln Pro Cys
             325                 330                 335
Ala Asp Asn Ala Val Leu Ser Ser Gly Leu Thr Ala Ala Arg
             340                 345                 350

<210> SEQ ID NO 4
<211> LENGTH: 351
<212> TYPE: PRT
<213> ORGANISM: Homo sapiens

<400> SEQUENCE: 4

Met Gly Asn Ala Ala Ala Ala Lys Lys Gly Ser Glu Gln Glu Ser Val
1               5                   10                  15
Lys Glu Phe Leu Ala Lys Ala Lys Glu Asp Phe Leu Lys Lys Trp Glu
             20                  25                  30
Ser Pro Ala Gln Asn Thr Ala His Leu Asp Gln Phe Glu Arg Ile Lys
         35                  40                  45
Thr Leu Gly Thr Gly Ser Phe Gly Arg Val Met Leu Val Lys His Lys
     50                  55                  60
Glu Thr Gly Asn His Tyr Ala Met Lys Ile Leu Asp Lys Gln Lys Val
65                  70                  75                  80
Val Lys Leu Lys Gln Ile Glu His Thr Leu Asn Glu Lys Arg Ile Leu
                 85                  90                  95
Gln Ala Val Asn Phe Pro Phe Leu Val Lys Leu Glu Phe Ser Phe Lys
             100                 105                 110
Asp Asn Ser Asn Leu Tyr Met Val Met Glu Tyr Val Pro Gly Gly Glu
         115                 120                 125
Met Phe Ser His Leu Arg Arg Ile Gly Arg Phe Ser Glu Pro His Ala
     130                 135                 140
Arg Phe Tyr Ala Ala Gln Ile Val Leu Thr Phe Glu Tyr Leu His Ser
145                 150                 155                 160
Leu Asp Leu Ile Tyr Arg Asp Leu Lys Pro Glu Asn Leu Leu Ile Asp
                 165                 170                 175
Gln Gln Gly Tyr Ile Gln Val Thr Asp Phe Gly Phe Ala Lys Arg Val
             180                 185                 190
Lys Gly Arg Thr Trp Thr Leu Cys Gly Thr Pro Glu Tyr Leu Ala Pro
         195                 200                 205
Glu Ile Ile Leu Ser Lys Gly Tyr Asn Lys Ala Val Asp Trp Trp Ala
     210                 215                 220
Leu Gly Val Leu Ile Tyr Glu Met Ala Ala Gly Tyr Pro Pro Phe Phe
225                 230                 235                 240
Ala Asp Gln Pro Ile Gln Ile Tyr Glu Lys Ile Val Ser Gly Lys Val
                 245                 250                 255
Arg Phe Pro Ser His Phe Ser Ser Asp Leu Lys Asp Leu Leu Arg Asn
             260                 265                 270
```

Leu Leu Gln Val Asp Leu Thr Lys Arg Phe Gly Asn Leu Lys Asn Gly
            275                 280                 285

Val Asn Asp Ile Lys Asn His Lys Trp Phe Ala Thr Thr Asp Trp Ile
290                 295                 300

Ala Ile Tyr Gln Arg Lys Val Glu Ala Pro Phe Ile Pro Lys Phe Lys
305                 310                 315                 320

Gly Pro Gly Asp Thr Ser Asn Phe Asp Asp Tyr Glu Glu Glu Glu Ile
                325                 330                 335

Arg Val Ser Ile Asn Glu Lys Cys Gly Lys Glu Phe Ser Glu Phe
            340                 345                 350

<210> SEQ ID NO 5
<211> LENGTH: 63
<212> TYPE: PRT
<213> ORGANISM: Homo sapiens

<400> SEQUENCE: 5

Gln Tyr Leu Arg Leu Asn Asp Asn Pro Trp Val Cys Asp Cys Arg Ala
1               5                   10                  15

Arg Pro Leu Trp Ala Trp Leu Gln Lys Phe Arg Gly Ser Ser Ser Glu
            20                  25                  30

Val Pro Cys Ser Leu Pro Gln Arg Leu Ala Gly Arg Asp Leu Lys Arg
        35                  40                  45

Leu Ala Ala Asn Asp Leu Gln Gly Cys Ala Val Ala Thr Gly Pro
    50                  55                  60

<210> SEQ ID NO 6
<211> LENGTH: 63
<212> TYPE: PRT
<213> ORGANISM: Mus musculus

<400> SEQUENCE: 6

Gln Tyr Leu Arg Leu Asn Asp Asn Pro Trp Val Cys Asp Cys Arg Ala
1               5                   10                  15

Arg Pro Leu Trp Ala Trp Leu Gln Lys Phe Arg Gly Ser Ser Ser Glu
            20                  25                  30

Val Pro Cys Asn Leu Pro Gln Arg Leu Ala Asp Arg Asp Leu Lys Arg
        35                  40                  45

Leu Ala Ala Ser Asp Leu Glu Gly Cys Ala Val Ala Ser Gly Pro
    50                  55                  60

<210> SEQ ID NO 7
<211> LENGTH: 63
<212> TYPE: PRT
<213> ORGANISM: Rattus norvegicus

<400> SEQUENCE: 7

Gln Tyr Leu Arg Leu Asn Asp Asn Pro Trp Val Cys Asp Cys Arg Ala
1               5                   10                  15

Arg Pro Leu Trp Ala Trp Leu Gln Lys Phe Arg Gly Ser Ser Ser Glu
            20                  25                  30

Val Pro Cys Asn Leu Pro Gln Arg Leu Ala Gly Arg Asp Leu Lys Arg
        35                  40                  45

Leu Ala Ala Ser Asp Leu Glu Gly Cys Ala Val Ala Ser Gly Pro
    50                  55                  60

<210> SEQ ID NO 8
<211> LENGTH: 62
<212> TYPE: PRT

<213> ORGANISM: Danio rerio

<400> SEQUENCE: 8

```
Gln Tyr Leu Arg Leu Asn Gly Asn Gln Trp Ile Cys Asp Cys Arg Ala
 1               5                  10                  15
Arg Pro Leu Trp Asp Trp Phe Lys Arg Phe Lys Gly Ser Ser Ser Asp
            20                  25                  30
Leu Glu Cys His Leu Pro Ala Ser Leu Asn Gly Lys Asp Leu Lys Arg
        35                  40                  45
Leu Lys Ser Asp Asp Leu Glu Gly Cys Val Asp Ser Pro Ser
    50                  55                  60
```

<210> SEQ ID NO 9
<211> LENGTH: 62
<212> TYPE: PRT
<213> ORGANISM: gallus gallus

<400> SEQUENCE: 9

```
Gln Tyr Leu Arg Leu Asn Gly Asn Gln Trp Ile Cys Asp Cys Gln Ala
 1               5                  10                  15
Arg Ser Leu Trp Asn Trp Phe Lys Gln Phe Lys Gly Ser Ser Ser Glu
            20                  25                  30
Leu Glu Cys His Leu Pro Pro His Leu Ala Gly Arg Asp Leu Lys Arg
        35                  40                  45
Leu Gln Ser Asp Asp Leu Glu Gly Cys Ile Asp Ser Phe Asn
    50                  55                  60
```

<210> SEQ ID NO 10
<211> LENGTH: 62
<212> TYPE: PRT
<213> ORGANISM: Homo sapiens

<400> SEQUENCE: 10

```
Glu Phe Leu Arg Leu Asn Ala Asn Pro Trp Ala Cys Asp Cys Arg Ala
 1               5                  10                  15
Arg Pro Leu Trp Ala Trp Phe Gln Arg Ala Arg Val Ser Ser Ser Asp
            20                  25                  30
Val Thr Cys Ala Thr Pro Pro Glu Arg Gln Gly Arg Asp Leu Arg Ala
        35                  40                  45
Leu Arg Glu Ala Asp Phe Gln Ala Cys Pro Pro Ala Ala Pro
    50                  55                  60
```

<210> SEQ ID NO 11
<211> LENGTH: 62
<212> TYPE: PRT
<213> ORGANISM: Mus musculus

<400> SEQUENCE: 11

```
Glu Phe Leu Arg Leu Asn Ala Asn Pro Trp Ala Cys Asp Cys Arg Ala
 1               5                  10                  15
Arg Pro Leu Trp Ala Trp Phe Gln Ala Arg Val Ser Ser Ser Asp
            20                  25                  30
Val Thr Cys Ala Thr Pro Pro Glu Arg Gln Gly Arg Asp Leu Arg Ala
        35                  40                  45
Leu Arg Asp Ser Asp Phe Gln Ala Cys Pro Pro Thr Pro
    50                  55                  60
```

<210> SEQ ID NO 12
<211> LENGTH: 63

```
<212> TYPE: PRT
<213> ORGANISM: Homo sapiens

<400> SEQUENCE: 12

Glu Phe Leu Arg Leu Asn Gly Asn Pro Trp Asp Cys Gly Cys Arg Ala
1               5                   10                  15

Arg Ser Leu Trp Glu Trp Leu Gln Arg Phe Arg Gly Ser Ser Ser Ala
            20                  25                  30

Val Pro Cys Val Ser Pro Gly Leu Arg His Gly Gln Asp Leu Lys Leu
        35                  40                  45

Leu Arg Ala Glu Asp Phe Arg Asn Cys Thr Gly Pro Ala Ser Pro
    50                  55                  60

<210> SEQ ID NO 13
<211> LENGTH: 63
<212> TYPE: PRT
<213> ORGANISM: Mus musculus

<400> SEQUENCE: 13

Glu Phe Leu Arg Leu Asn Gly Asn Ala Trp Asp Cys Gly Cys Arg Ala
1               5                   10                  15

Arg Ser Leu Trp Glu Trp Leu Gln Arg Phe Arg Gly Ser Ser Ser Ala
            20                  25                  30

Val Pro Cys Ala Thr Pro Glu Leu Arg Gln Gly Gln Asp Leu Lys Leu
        35                  40                  45

Leu Arg Val Glu Asp Phe Arg Asn Cys Thr Gly Pro Val Ser Pro
    50                  55                  60

<210> SEQ ID NO 14
<211> LENGTH: 13
<212> TYPE: PRT
<213> ORGANISM: Homo sapiens

<400> SEQUENCE: 14

Val Ser Ser Ser Asp Val Thr Cys Ala Thr Pro Pro Glu
1               5                   10

<210> SEQ ID NO 15
<211> LENGTH: 473
<212> TYPE: PRT
<213> ORGANISM: Mus musculus

<400> SEQUENCE: 15

Met Lys Arg Ala Ser Ser Gly Gly Ser Arg Leu Leu Ala Trp Val Leu
1               5                   10                  15

Trp Leu Gln Ala Trp Arg Val Ala Thr Pro Cys Pro Gly Ala Cys Val
            20                  25                  30

Cys Tyr Asn Glu Pro Lys Val Thr Thr Ser Cys Pro Gln Gln Gly Leu
        35                  40                  45

Gln Ala Val Pro Thr Gly Ile Pro Ala Ser Ser Gln Arg Ile Phe Leu
    50                  55                  60

His Gly Asn Arg Ile Ser His Val Pro Ala Ala Ser Phe Gln Ser Cys
65                  70                  75                  80

Arg Asn Leu Thr Ile Leu Trp Leu His Ser Asn Ala Leu Ala Arg Ile
                85                  90                  95

Asp Ala Ala Ala Phe Thr Gly Leu Thr Leu Leu Glu Gln Leu Asp Leu
            100                 105                 110

Ser Asp Asn Ala Gln Leu His Val Val Asp Pro Thr Thr Phe His Gly
        115                 120                 125
```

```
Leu Gly His Leu His Thr Leu His Leu Asp Arg Cys Gly Leu Arg Glu
        130                 135                 140

Leu Gly Pro Gly Leu Phe Arg Gly Leu Ala Ala Leu Gln Tyr Leu Tyr
145                 150                 155                 160

Leu Gln Asp Asn Asn Leu Gln Ala Leu Pro Asp Asn Thr Phe Arg Asp
                165                 170                 175

Leu Gly Asn Leu Thr His Leu Phe Leu His Gly Asn Arg Ile Pro Ser
                180                 185                 190

Val Pro Glu His Ala Phe Arg Gly Leu His Ser Leu Asp Arg Leu Leu
            195                 200                 205

Leu His Gln Asn His Val Ala Arg Val His Pro His Ala Phe Arg Asp
        210                 215                 220

Leu Gly Arg Leu Met Thr Leu Tyr Leu Phe Ala Asn Asn Leu Ser Met
225                 230                 235                 240

Leu Pro Ala Glu Val Leu Met Pro Leu Arg Ser Leu Gln Tyr Leu Arg
                245                 250                 255

Leu Asn Asp Asn Pro Trp Val Cys Asp Cys Arg Ala Arg Pro Leu Trp
                260                 265                 270

Ala Trp Leu Gln Lys Phe Arg Gly Ser Ser Ser Glu Val Pro Cys Asn
            275                 280                 285

Leu Pro Gln Arg Leu Ala Asp Arg Asp Leu Lys Arg Leu Ala Ala Ser
        290                 295                 300

Asp Leu Glu Gly Cys Ala Val Ala Ser Gly Pro Phe Arg Pro Ile Gln
305                 310                 315                 320

Thr Ser Gln Leu Thr Asp Glu Glu Leu Leu Ser Leu Pro Lys Cys Cys
                325                 330                 335

Gln Pro Asp Ala Ala Asp Lys Ala Ser Val Leu Glu Pro Gly Arg Pro
            340                 345                 350

Ala Ser Ala Gly Asn Ala Leu Lys Gly Arg Val Pro Pro Gly Asp Thr
        355                 360                 365

Pro Pro Gly Asn Gly Ser Gly Pro Arg His Ile Asn Asp Ser Pro Phe
370                 375                 380

Gly Thr Leu Pro Ser Ser Ala Glu Pro Leu Thr Ala Leu Arg Pro
385                 390                 395                 400

Gly Gly Ser Glu Pro Pro Gly Leu Pro Thr Thr Gly Pro Arg Arg
                405                 410                 415

Pro Gly Cys Ser Arg Lys Asn Arg Thr Arg Ser His Cys Arg Leu Gly
            420                 425                 430

Gln Ala Gly Ser Gly Ala Ser Gly Thr Gly Asp Ala Glu Gly Ser Gly
        435                 440                 445

Ala Leu Pro Ala Leu Ala Cys Ser Leu Ala Pro Leu Gly Leu Ala Leu
        450                 455                 460

Val Leu Trp Thr Val Leu Gly Pro Cys
465                 470

<210> SEQ ID NO 16
<211> LENGTH: 473
<212> TYPE: PRT
<213> ORGANISM: Rattus norvegicus

<400> SEQUENCE: 16

Met Lys Arg Ala Ser Ser Gly Gly Ser Arg Leu Pro Thr Trp Val Leu
1               5                   10                  15

Trp Leu Gln Ala Trp Arg Val Ala Thr Pro Cys Pro Gly Ala Cys Val
```

```
                20                  25                  30
Cys Tyr Asn Glu Pro Lys Val Thr Thr Ser Arg Pro Gln Gln Gly Leu
            35                  40                  45

Gln Ala Val Pro Ala Gly Ile Pro Ala Ser Ser Gln Arg Ile Phe Leu
        50                  55                  60

His Gly Asn Arg Ile Ser Tyr Val Pro Ala Ala Ser Phe Gln Ser Cys
65                  70                  75                  80

Arg Asn Leu Thr Ile Leu Trp Leu His Ser Asn Ala Leu Ala Gly Ile
                85                  90                  95

Asp Ala Ala Phe Thr Gly Leu Thr Leu Leu Glu Gln Leu Asp Leu
            100                 105                 110

Ser Asp Asn Ala Gln Leu Arg Val Val Asp Pro Thr Thr Phe Arg Gly
        115                 120                 125

Leu Gly His Leu His Thr Leu His Leu Asp Arg Cys Gly Leu Gln Glu
        130                 135                 140

Leu Gly Pro Gly Leu Phe Arg Gly Leu Ala Ala Leu Gln Tyr Leu Tyr
145                 150                 155                 160

Leu Gln Asp Asn Asn Leu Gln Ala Leu Pro Asp Asn Thr Phe Arg Asp
                165                 170                 175

Leu Gly Asn Leu Thr His Leu Phe Leu His Gly Asn Arg Ile Pro Ser
            180                 185                 190

Val Pro Glu His Ala Phe Arg Gly Leu His Ser Leu Asp Arg Leu Leu
        195                 200                 205

Leu His Gln Asn His Val Ala Arg Val His Pro His Ala Phe Arg Asp
        210                 215                 220

Leu Gly Arg Leu Met Thr Leu Tyr Leu Phe Ala Asn Asn Leu Ser Met
225                 230                 235                 240

Leu Pro Ala Glu Val Leu Val Pro Leu Arg Ser Leu Gln Tyr Leu Arg
                245                 250                 255

Leu Asn Asp Asn Pro Trp Val Cys Asp Cys Arg Ala Arg Pro Leu Trp
            260                 265                 270

Ala Trp Leu Gln Lys Phe Arg Gly Ser Ser Ser Gly Val Pro Ser Asn
        275                 280                 285

Leu Pro Gln Arg Leu Ala Gly Arg Asp Leu Lys Arg Leu Ala Thr Ser
        290                 295                 300

Asp Leu Glu Gly Cys Ala Val Ala Ser Gly Pro Phe Arg Pro Phe Gln
305                 310                 315                 320

Thr Asn Gln Leu Thr Asp Glu Glu Leu Leu Gly Leu Pro Lys Cys Cys
                325                 330                 335

Gln Pro Asp Ala Ala Asp Lys Ala Ser Val Leu Glu Pro Gly Arg Pro
            340                 345                 350

Ala Ser Val Gly Asn Ala Leu Lys Gly Arg Val Pro Pro Gly Asp Thr
        355                 360                 365

Pro Pro Gly Asn Gly Ser Gly Pro Arg His Ile Asn Asp Ser Pro Phe
        370                 375                 380

Gly Thr Leu Pro Gly Ser Ala Glu Pro Pro Leu Thr Ala Leu Arg Pro
385                 390                 395                 400

Gly Gly Ser Glu Pro Pro Gly Leu Pro Thr Thr Gly Pro Arg Arg Arg
                405                 410                 415

Pro Gly Cys Ser Arg Lys Asn Arg Thr Arg Ser His Cys Arg Leu Gly
            420                 425                 430

Gln Ala Gly Ser Gly Ser Ser Gly Thr Gly Asp Ala Glu Gly Ser Gly
        435                 440                 445
```

```
Ala Leu Pro Ala Leu Ala Cys Ser Leu Ala Pro Leu Gly Leu Ala Leu
    450                 455                 460

Val Leu Trp Thr Val Leu Gly Pro Cys
465                 470
```

<210> SEQ ID NO 17
<211> LENGTH: 479
<212> TYPE: PRT
<213> ORGANISM: Danio rerio

<400> SEQUENCE: 17

```
Met Lys Thr Leu Ile Val Glu Gly Gly Arg Leu Leu Cys Leu Met Phe
1               5                  10                  15

Trp Leu Asn Leu Val Pro Val Ile Asn Ser Cys Pro Ala Lys Cys Val
            20                  25                  30

Cys Tyr Ser Glu Pro Lys Ala Thr Val Ala Cys Gln Gln Gln Gly Leu
        35                  40                  45

Phe Ser Ile Pro Thr Glu Ile Pro Val Arg Ser Gln Arg Ile Phe Leu
    50                  55                  60

Gln Ser Asn Lys Leu Thr Val Val Arg Ser Thr Ser Phe Ser Ser Val
65                  70                  75                  80

His Asn Leu Thr Val Leu Trp Met Tyr Ser Asn Asn Ile Ser His Ile
                85                  90                  95

Glu Ala Gly Ala Phe Tyr Gly Leu Glu Arg Leu Glu Glu Leu Asp Ile
            100                 105                 110

Gly Asp Asn Ser Asn Leu Arg Ile Ile Ser Pro Thr Ala Phe Arg Gly
        115                 120                 125

Leu Thr Lys Leu His Thr Leu His Leu His Arg Cys Gly Leu Ser Glu
    130                 135                 140

Leu Pro Val Gly Val Phe Arg Gly Leu Phe Ser Leu Gln Tyr Leu Tyr
145                 150                 155                 160

Leu Gln Asp Asn Asn Leu Leu Ala Leu His Glu Asp Thr Phe Leu Asp
                165                 170                 175

Leu Ala Asn Leu Thr Tyr Leu Phe Leu His Asn Asn Lys Ile Lys Val
            180                 185                 190

Val Thr Asp His Met Leu Arg Gly Leu Val Asn Leu Asp Arg Leu Leu
        195                 200                 205

Leu His Gln Asn Arg Ile Val His Val Gln Gln Ala Phe Asn Asp
    210                 215                 220

Leu Ser Lys Leu Thr Thr Leu Phe Leu Phe Asn Asn Leu Thr Met
225                 230                 235                 240

Leu Thr Gly Glu Ser Met Asn Pro Leu Val Ser Leu Gln Tyr Leu Arg
                245                 250                 255

Leu Asn Gly Asn Gln Trp Ile Cys Asp Cys Arg Ala Arg Pro Leu Trp
            260                 265                 270

Asp Trp Phe Lys Arg Phe Lys Gly Ser Ser Asp Leu Glu Cys His
        275                 280                 285

Leu Pro Ala Ser Leu Asn Gly Lys Asp Leu Arg Leu Lys Ser Asp
    290                 295                 300

Asp Leu Glu Gly Cys Val Asp Ser Pro Ser Gln Val Gln Thr Ser Ile
305                 310                 315                 320

Phe Asn Ser Lys Val His Ser Gly Lys Phe Leu Ser Leu Asp Asp Pro
                325                 330                 335

Leu Val Glu Ser Ile Pro Arg Cys Cys Leu Ser Asp Asn Asp Lys Ser
```

```
                    340                 345                 350
Ser Ile Ile Ser Ser Lys Ser Ile Pro Asp Pro Ser Ser Tyr Asn Ser
            355                 360                 365

Arg Gln Ile Thr Asn Asn Pro Leu Lys Glu Lys Glu Asn Ile Ser Lys
        370                 375                 380

Thr Lys Phe Arg Glu Val Glu Arg Thr Lys Asn Glu Thr Arg Asn Lys
385                 390                 395                 400

Gln Ser Leu Asn Asp Gly Pro Leu Gly Thr Met Ser Asn Asn Leu Asp
                405                 410                 415

Gln Ser Leu Asp Arg Ile Asp Pro Glu Leu Leu Gly Asn Leu Glu Pro
            420                 425                 430

Ser Thr Ala Pro Thr Lys Lys Lys Lys Cys Ser Lys Lys Pro Lys
        435                 440                 445

Ser Asp Gln Asn Cys Leu Lys Gly His Gly Ser Thr Ile Gln Val Leu
    450                 455                 460

Ala Val Ile Phe Leu Pro Leu Phe Trp Leu Ser Leu Ala Leu Ser
465                 470                 475

<210> SEQ ID NO 18
<211> LENGTH: 483
<212> TYPE: PRT
<213> ORGANISM: Gallus gallus

<400> SEQUENCE: 18

Ser Ala Arg Ser Leu Pro Glu Gly Ser Lys Leu Leu Ile Leu Val Leu
1               5                   10                  15

Cys Leu Asn Ile Gln Ser Glu Val Glu Ser Cys Pro Gly Ala Cys Val
            20                  25                  30

Cys Tyr Ser Glu Pro Lys Ile Thr Ile Ser Cys Gln Gln Gln Gly Leu
        35                  40                  45

Thr Ala Ile Pro Thr Glu Ile Pro Ile Gln Ser Gln Arg Ile Phe Leu
    50                  55                  60

His Asn Asn Lys Ile Thr Leu Val Arg Ser Thr Ser Phe Thr Ser Cys
65                  70                  75                  80

Arg Asn Met Thr Ile Leu Trp Ile His Ser Asn Asn Ile Ser Leu Ile
                85                  90                  95

Glu Pro Gly Ala Phe Tyr Gly Leu Asn Lys Leu Glu Glu Leu Asp Leu
            100                 105                 110

Ser Asp Asn Thr Asn Leu Lys Ser Ile Asn Pro Val Thr Phe Arg Gly
        115                 120                 125

Leu Val His Leu His Thr Leu His Leu Asp Arg Cys Gly Leu Met Glu
    130                 135                 140

Leu Ser Thr Gly Leu Phe Arg Gly Leu Phe Ser Leu Gln Tyr Leu Tyr
145                 150                 155                 160

Leu Gln Asp Asn Asn Leu Gln Asn Leu Leu Asp Asp Thr Phe Ile Asp
                165                 170                 175

Leu Ala Asn Leu Thr Tyr Leu Phe Leu His Gly Asn Lys Ile Lys Ser
            180                 185                 190

Leu Ser Glu Asn Val Phe Arg Gly Leu Ile Asn Leu Asp Arg Leu Leu
        195                 200                 205

Leu His Gln Asn Arg Val Ser Leu Val His Arg Arg Ser Phe His Asp
    210                 215                 220

Leu Gly Lys Val Met Thr Leu Tyr Leu Phe Asn Asn Asn Leu Thr Val
225                 230                 235                 240
```

Leu Thr Gly Glu Thr Met Ala Pro Leu Val Ser Leu Gln Tyr Leu Arg
                245                 250                 255

Leu Asn Gly Asn Gln Trp Ile Cys Asp Cys Gln Ala Arg Ser Leu Trp
            260                 265                 270

Asn Trp Phe Lys Gln Phe Lys Gly Ser Ser Ser Glu Leu Glu Cys His
        275                 280                 285

Leu Pro Pro His Leu Ala Gly Arg Asp Leu Lys Arg Leu Gln Ser Ser
    290                 295                 300

Asp Leu Glu Gly Cys Ile Asp Ser Phe Asn Gln Ile Arg Thr Ser Val
305                 310                 315                 320

Phe Ser Thr Lys Thr Arg Ser Gly Lys Leu Ala Thr Gly Ser Pro Pro
                325                 330                 335

Leu Ser Ser His Asp Gly Ser Met Lys Cys Cys Gln Pro Glu Met Asp
            340                 345                 350

Lys Ser Phe Ile Tyr Glu Ala Lys Gly Lys Ala Gly Pro Ser Ser His
        355                 360                 365

Ser Ser Arg Pro Ser Ser Asn Asn Pro Leu Lys Asp Lys Glu Asn Met
    370                 375                 380

Ser Lys Thr Lys Tyr Val Glu Thr Asp Pro Ser Lys Asn Gly Ser Asn
385                 390                 395                 400

Lys Gln Ile Asn Asp Ser Pro Phe Gly Thr Phe Pro Ser Ile Val Asp
                405                 410                 415

Pro Pro Leu Thr Lys Leu Arg Pro Glu Phe Leu Glu Pro Ile Glu Pro
            420                 425                 430

Ser Thr Val Pro Thr Lys Lys Arg Gln Gly Cys Ser Lys Lys Asn Lys
        435                 440                 445

Ser Lys Ala Gln Cys Arg Leu Thr Gln Gln Gly Asn Ser Ser Thr Leu
    450                 455                 460

Gln Leu Ser Leu Ser Leu Leu Ile Pro Pro Leu Val Trp Ser Leu Leu
465                 470                 475                 480

Leu Leu Cys

<210> SEQ ID NO 19
<211> LENGTH: 420
<212> TYPE: PRT
<213> ORGANISM: Homo sapiens

<400> SEQUENCE: 19

Met Leu Pro Gly Leu Arg Arg Leu Leu Gln Ala Pro Ala Ser Ala Cys
1               5                   10                  15

Leu Leu Leu Met Leu Leu Ala Leu Pro Leu Ala Ala Pro Ser Cys Pro
            20                  25                  30

Met Leu Cys Thr Cys Tyr Ser Ser Pro Pro Thr Val Ser Cys Gln Ala
        35                  40                  45

Asn Asn Phe Ser Ser Val Pro Leu Ser Leu Pro Pro Ser Thr Gln Arg
    50                  55                  60

Leu Phe Leu Gln Asn Asn Leu Ile Arg Thr Leu Arg Pro Gly Thr Phe
65                  70                  75                  80

Gly Ser Asn Leu Leu Thr Leu Trp Leu Phe Ser Asn Asn Leu Ser Thr
                85                  90                  95

Ile Tyr Pro Gly Thr Phe Arg His Leu Gln Ala Leu Glu Glu Leu Asp
            100                 105                 110

Leu Gly Asp Asn Arg His Leu Arg Ser Leu Glu Pro Asp Thr Phe Gln
        115                 120                 125

Gly Leu Glu Arg Leu Gln Ser Leu His Leu Tyr Arg Cys Gln Leu Ser
130                 135                 140

Ser Leu Pro Gly Asn Ile Phe Arg Gly Leu Val Ser Leu Gln Tyr Leu
145                 150                 155                 160

Tyr Leu Gln Glu Asn Ser Leu Leu His Leu Gln Asp Asp Leu Phe Ala
                165                 170                 175

Asp Leu Ala Asn Leu Ser His Leu Phe Leu His Gly Asn Arg Leu Arg
            180                 185                 190

Leu Leu Thr Glu His Val Phe Arg Gly Leu Gly Ser Leu Asp Arg Leu
        195                 200                 205

Leu Leu His Gly Asn Arg Leu Gln Gly Val His Arg Ala Ala Phe Arg
    210                 215                 220

Gly Leu Ser Arg Leu Thr Ile Leu Tyr Leu Phe Asn Asn Ser Leu Ala
225                 230                 235                 240

Ser Leu Pro Gly Glu Ala Leu Ala Asp Leu Pro Ser Leu Glu Phe Leu
                245                 250                 255

Arg Leu Asn Ala Asn Pro Trp Ala Cys Asp Cys Arg Ala Arg Pro Leu
            260                 265                 270

Trp Ala Trp Phe Gln Arg Ala Arg Val Ser Ser Ser Asp Val Thr Cys
        275                 280                 285

Ala Thr Pro Pro Glu Arg Gln Gly Arg Asp Leu Arg Ala Leu Arg Glu
    290                 295                 300

Ala Asp Phe Gln Ala Cys Pro Pro Ala Ala Pro Thr Arg Pro Gly Ser
305                 310                 315                 320

Arg Ala Arg Gly Asn Ser Ser Asn His Leu Tyr Gly Val Ala Glu
                325                 330                 335

Ala Gly Ala Pro Pro Ala Asp Pro Ser Thr Leu Tyr Arg Asp Leu Pro
            340                 345                 350

Ala Glu Asp Ser Arg Gly Arg Gln Gly Gly Asp Ala Pro Thr Glu Asp
        355                 360                 365

Asp Tyr Trp Gly Gly Tyr Gly Gly Glu Asp Gln Arg Gly Glu Gln Met
    370                 375                 380

Cys Pro Gly Ala Ala Cys Gln Ala Pro Pro Asp Ser Arg Gly Pro Ala
385                 390                 395                 400

Leu Ser Ala Gly Leu Pro Ser Pro Leu Leu Cys Leu Leu Leu Val
                405                 410                 415

Pro His His Leu
        420

<210> SEQ ID NO 20
<211> LENGTH: 441
<212> TYPE: PRT
<213> ORGANISM: Homo sapiens

<400> SEQUENCE: 20

Met Leu Arg Lys Gly Cys Cys Val Glu Leu Leu Leu Leu Leu Val Ala
1               5                   10                  15

Ala Glu Leu Pro Leu Gly Gly Gly Cys Pro Arg Asp Cys Val Cys Tyr
            20                  25                  30

Pro Ala Pro Met Thr Val Ser Cys Gln Ala His Asn Phe Ala Ala Ile
        35                  40                  45

Pro Glu Gly Ile Pro Val Asp Ser Glu Arg Val Phe Leu Gln Asn Asn
    50                  55                  60

Arg Ile Gly Leu Leu Gln Pro Gly His Phe Ser Pro Ala Met Val Thr
65                  70                  75                  80

Leu Trp Ile Tyr Ser Asn Asn Ile Thr Tyr Ile His Pro Ser Thr Phe
                85                  90                  95

Glu Gly Phe Val His Leu Glu Glu Leu Asp Leu Gly Asp Asn Arg Gln
            100                 105                 110

Leu Arg Thr Leu Ala Pro Glu Thr Phe Gln Gly Leu Val Lys Leu His
        115                 120                 125

Ala Leu Tyr Leu Tyr Lys Cys Gly Leu Ser Ala Leu Pro Ala Gly Val
130                 135                 140

Phe Gly Gly Leu His Ser Leu Gln Tyr Leu Tyr Leu Gln Asp Asn His
145                 150                 155                 160

Ile Glu Tyr Leu Gln Asp Asp Ile Phe Val Asp Leu Val Asn Leu Ser
                165                 170                 175

His Leu Phe Leu His Gly Asn Lys Leu Trp Ser Leu Gly Pro Gly Thr
            180                 185                 190

Phe Arg Gly Leu Val Asn Leu Asp Arg Leu Leu Leu His Glu Asn Gln
        195                 200                 205

Leu Gln Trp Val His His Lys Ala Phe His Asp Leu Arg Arg Leu Thr
210                 215                 220

Thr Leu Phe Leu Phe Asn Asn Ser Leu Ser Glu Leu Gln Gly Glu Cys
225                 230                 235                 240

Leu Ala Pro Leu Gly Ala Leu Glu Phe Leu Arg Leu Asn Gly Asn Pro
                245                 250                 255

Trp Asp Cys Gly Cys Arg Ala Arg Ser Leu Trp Glu Trp Leu Gln Arg
            260                 265                 270

Phe Arg Gly Ser Ser Ala Val Pro Cys Val Ser Pro Gly Leu Arg
        275                 280                 285

His Gly Gln Asp Leu Lys Leu Leu Arg Ala Glu Asp Phe Arg Asn Cys
290                 295                 300

Thr Gly Pro Ala Ser Pro His Gln Ile Lys Ser His Thr Leu Thr Thr
305                 310                 315                 320

Thr Asp Arg Ala Ala Arg Lys Glu His His Ser Pro His Gly Pro Thr
                325                 330                 335

Arg Ser Lys Gly His Pro His Gly Pro Arg Pro Gly His Arg Lys Pro
            340                 345                 350

Gly Lys Asn Cys Thr Asn Pro Arg Asn Arg Asn Gln Ile Ser Lys Ala
        355                 360                 365

Gly Ala Gly Lys Gln Ala Pro Glu Leu Pro Asp Tyr Ala Pro Asp Tyr
370                 375                 380

Gln His Lys Phe Ser Phe Asp Ile Met Pro Thr Ala Arg Pro Lys Arg
385                 390                 395                 400

Lys Gly Lys Cys Ala Arg Arg Thr Pro Ile Arg Ala Pro Ser Gly Val
                405                 410                 415

Gln Gln Ala Ser Ser Ala Ser Ser Leu Gly Ala Ser Leu Leu Ala Trp
            420                 425                 430

Thr Leu Gly Leu Ala Val Thr Leu Arg
        435                 440

<210> SEQ ID NO 21
<211> LENGTH: 28
<212> TYPE: PRT
<213> ORGANISM: Mus musculus

<400> SEQUENCE: 21

Ser Gly Leu Ser Lys Lys Pro Ser Leu Leu Thr His Gln Gly His Ile

```
1               5                   10                  15
Leu Asp Pro Gly Met Thr Leu Thr Leu Gln Cys Phe
                20                  25

<210> SEQ ID NO 22
<211> LENGTH: 28
<212> TYPE: PRT
<213> ORGANISM: Homo sapiens

<400> SEQUENCE: 22

Leu Gly Val Ser Lys Lys Pro Ser Leu Ser Val Gln Pro Gly Pro Ile
1               5                   10                  15

Val Ala Pro Glu Glu Thr Leu Thr Leu Gln Cys Gly
                20                  25

<210> SEQ ID NO 23
<211> LENGTH: 28
<212> TYPE: PRT
<213> ORGANISM: Homo sapiens

<400> SEQUENCE: 23

Pro Gly Val Ser Lys Lys Pro Ser Leu Ser Val Gln Pro Gly Pro Val
1               5                   10                  15

Val Ala Pro Gly Glu Ser Leu Thr Leu Gln Cys Val
                20                  25

<210> SEQ ID NO 24
<211> LENGTH: 28
<212> TYPE: PRT
<213> ORGANISM: Homo sapiens

<400> SEQUENCE: 24

Ser Gly Val Ser Arg Lys Pro Ser Leu Leu Thr Leu Gln Gly Pro Val
1               5                   10                  15

Leu Ala Pro Gly Gln Ser Leu Thr Leu Gln Cys Gly
                20                  25

<210> SEQ ID NO 25
<211> LENGTH: 28
<212> TYPE: PRT
<213> ORGANISM: Homo sapiens

<400> SEQUENCE: 25

Pro Gly Val Ser Arg Lys Pro Ser Leu Leu Ile Pro Gln Gly Ser Val
1               5                   10                  15

Val Ala Arg Gly Gly Ser Leu Thr Leu Gln Cys Arg
                20                  25

<210> SEQ ID NO 26
<211> LENGTH: 28
<212> TYPE: PRT
<213> ORGANISM: Rattus norvegicus

<400> SEQUENCE: 26

Ser Gly Pro Ser Arg Lys Pro Ser Leu Leu Ser His Gln Gly His Ile
1               5                   10                  15

Leu Glu Pro Gly Met Ser Leu Thr Leu Gln Cys Tyr
                20                  25
```